United States Patent [19]
Elder et al.

[11] Patent Number: 5,736,378
[45] Date of Patent: Apr. 7, 1998

[54] MOLECULAR CLONING AND CHARACTERIZATION OF THE FELINE IMMUNODEFICIENCY VIRUS ISOLATE PPR

[75] Inventors: John H. Elder, Encinitas; Randy L. Talbott, San Diego, both of Calif.

[73] Assignee: The Scripps Research Institute, La Jolla, Calif.

[21] Appl. No.: 325,547

[22] Filed: Oct. 18, 1994

Related U.S. Application Data

[63] Continuation of Ser. No. 759,570, Sep. 12, 1991, abandoned.
[51] Int. Cl.$^6$ .............................. C12N 7/00; C12N 7/01; C12N 1/20; C12P 19/34
[52] U.S. Cl. ........................... 435/235.1; 435/91.33; 435/252.3; 424/187.1; 424/207.1; 536/23.72
[58] Field of Search ..................... 536/23.72, 24.1; 424/187.1, 188.1; 435/69.1, 71.1, 91.4, 172.3, 252.3

[56] References Cited

U.S. PATENT DOCUMENTS

| | | |
|---|---|---|
| 4,556,556 | 12/1985 | Wiesehahn et al. |
| 4,652,629 | 3/1987 | Patrick et al. |
| 4,701,416 | 10/1987 | Nunberg . |
| 4,861,588 | 8/1989 | Neurath et al. |
| 4,861,720 | 8/1989 | Pedersen et al. |
| 5,017,487 | 5/1991 | Stunnenberg et al. |
| 5,017,687 | 5/1991 | Vahlne et al. |
| 5,017,688 | 5/1991 | Gilbert et al. |
| 5,019,386 | 5/1991 | Machida et al. |
| 5,037,753 | 8/1991 | Pedersen et al. ........... 435/235.1 |
| 5,275,813 | 1/1994 | Yamamoto et al. ........... 424/89 |

FOREIGN PATENT DOCUMENTS 9013573  11/1990  WIPO ................. C07K 13/00

OTHER PUBLICATIONS

Olmstead et al., 1989 Proc. Natl. Acad. Sci. USA 86:8088–8092.
Olmstead et al., 1989 Proc. Natl. Acad. Sci. USA 86:2448–2452.
Phillips et al., 1990 J. Virol. 64:4650–4613.
Young, R.A. et al. (1983) Proc. Natl. Acad. Sci USA 80: 1194–1198.
Helfman, D.M. et al. (1987) Meth. Enzym. 152: 451–457.
Wood, W.I. (1987) Meth. Enzym. 152:443–447.
Miyazawa, T. et al. (91) J. Virol. 65:1572–1577.
Olmsted, R.A. et al. (89) Proc. Natl. Acad. Sci USA 86:2448–2452.
Morikawa, S. et al. (91) Virus Res. 21:53–63.
Mierendorf, R.L. et al. (87) Meth. Enzym. 152:458–469.
Phillips, et al., Comparison of Two Host Cell Range Variants of Feline Immunodeficiency Virus, Journal of Virology, Oct. 1990, pp. 4605–4613.

Yamamoto, et al., Pathogenesis of experimenta–ly induced feline immunodeficiency virus infection in cats, Am J. Vet Res, vol. 49, No. 8, Aug. 1988.

Talbott, et al., Nucleotide sequence and genomic organization of feline immunodeficiency virus, Proc. Natl. Acad. Sci. USA, vol. 86, pp. 5743–5747, Aug. 1989.

Tochikura, et al., In Vitro Replication and Cytopathogenicity of the Feline Immunodeficiency Virus . . . , Virology 179, 492–497 (1990).

Pedersen, et al., Isolation of a T–Lymphotropic Virus from Domestic Cats with an Immunodeficiency–Like Syndrome, Science, vol. 235, pp. 790–793.

Borman, Recombinant TB Vaccines: Use against other diseases sought, C&EN 69:4 (1991).

Pedersen, et al., Feline Leukemia Virus Infection as a Potentiating Cofactor for the Primary and Secondary Stages . . . , Journal of Virology, Feb. 1990, pp. 598–606.

Olmsted, et al., Nucleotide sequence analysis of feline immunodeficiency virus: Genome organization . . . , Proc. Natl.Acad.Sci.USA, vol. 86, pp. 8088–8092, Oct. 1989.

(1991) Chemical and Engineering News, 69:24 (1991).

Dow, et al., Feline Immunodeficiency Virus: A Neurotropic Lentivirus, Journal of Acquired Immune Deficiency Syndromes, 3:658–668, 1990.

Pedersen, et al., Feline Immunodeficiency Virus Infection, Proceedings, 7th Feline Medicine Symposium 1989, pp. 6–21.

Connaughton, What you need to know about the feline immunodeficiency virus, JAVMA, vol. 194, No. 2, Jan. 15, 1989, pp. 169–173.

Chalmers, et al., Demodicosis in two cats seropositive for feline immunodeficiency virus, JAVMA, vol. 194, No. 2, Jan. 15, 1989, pp. 256–257.

*Primary Examiner*—Christine M. Nucker
*Assistant Examiner*—Jeffrey S. Parkin
*Attorney, Agent, or Firm*—Fish & Richardson P.C.

[57] ABSTRACT

Molecular clones of the feline immunodeficiency virus isolate PPR ($FIV_{PPR}$) were obtained from a genomic library prepared from infected feline peripheral blood lymphocytes (PBLs). $FIV_{PPR}$ infected and replicated efficiently in feline PBLs but not Crandall feline kidney (CRFK) or G355-5 cells. In contrast, a clone designated 34TF10 of the prototypical FIV Petaluma isolate ($FIV_{Pet}$) replicated inefficiently on feline PBLs while readily infecting and replicating in CRFK and G355-5 cells. The 34TF10 and PPR clones have an overall nucleic acid sequence identity of 91% while the env genes display only 85% conservation at the amino acid level. The long terminal repeats (LTRs) were 7% divergent between the two clones, with a lack of conservation in putative NF-κB, LBP-1, and CCAAT enhancer promoter sites. Full-length proviral clones will provide important biochemic, immunologic, and diagnostic reagents.

5 Claims, 23 Drawing Sheets

FIG.6A

```
PPR    EYIVVPTEVMTYKYKQKRAAIHIMLALATVLSIAGAGTGATAIGMVTQYQQVLATHQEALDKITEALKINNLRLVTLEHQMLVIGLKVEAIEKFLYTAFA  698
       :.:!:.!!!.!!.. :.!!!    !!!!!!!!!!!!!!!!!!!!!!!!!!!!!!!!!!!!!! !!!!!!.:.!!!!!!!!!!!!!!!!!!!!!!!!!!!!!!
34TF10 DYLLVPEEVMEYKPRRKRAAIHVMLALATVLSIAGAGTGATAIGMVTQYHQVLATHQEAIEKVTGALKINNLRLVTLEHQVLVIGLKVEAMEKFLYTAFA  700
                            ──TM──→ ──Trans Mem Reg(1)──                           ──Trans Mem Reg(2)──

PPR    MQELGCNQNQFFCEIPKELWLRYNMTLNQTWNHGNITLGEWYNQTKYLQQKFYEIIMDIEQNNVQGKQGLQKLQNWQDMWGWIGKIPQYLKGLLGGILG  798
       !!!!!!!!!!!!!.!!!:!!!.:!!!!!!!!!!!!!!!!!!!!!!!!!!!.!!!!!!!!!!!!!!!!!!!!!!.!:!!!:!!!!!:!!::!!!!!!!!!
34TF10 MQELGCNQNQFFCKIPLELWTRYNMTINQTWNHGNITLGEWYNQTKDLQQKFYEIIMDIEQNNVQGKTGIQQLQKWEDWVRWIGNIPQYLKGLLGGILG  800

PPR    IGLGILLLILCLPTLVDCIRNCISKVLGYTVIAMPEIDDEEETVQMELRKNGRQCGMSEKEEE  861
       !!!!!!!!!!!!!!!!!!!!!!:!!!!!!!!!!!!!!!  !: !!!!!!!!!!!!!!!!!!!
34TF10 IGLGVLLLILCLPTLVDCIRNCIHKILGYTVIAMPEVEGEEIQPQMELRRNGRQCGMSEKEEE  863
```

FIG. 6B

```
                    ORF2 →
                                                                          60
34TF    MetGluGluIleIleValLeuPheAsnArgValThrGluLysLeuGluLysGluLeuAla
34TF    ATGGAAGAAATAATAGTATTATTCAATAGGGTCACTGAGAAACTAGAAAAAGAATTAGCT
             X   XXXXXXX    X     X      X   XXX    X  X  XX    X
PPR     ATGGAAGTAATACGG---ATATTTAATAAGGTCGCTGAAAGATTAGACAAGGAAGCAGCC
PPR     MetGluValIleArg---IlePheAsnLysValAlaGluArgLeuAspLysGluAlaAla 120
34TF    IleArgIlePheValLeuAlaHisGlnLeuGluArgAspLysAlaIleArgLeuLeuGln
34TF    ATCAGAATATTTGTATTAGCACATCAATTAGAAAGGGACAAAGCTATTAGATTACTACAA
           X                                X      X   XXX     X X  X
PPR     ATCAGGATATTTGTATTAGCACATCAATTAGAGAGGGATAAAATTGATTAGACTTCTGCAA
PPR     IleArgIlePheValLeuAlaHisGlnLeuGluArgAspLysLeuIleArgLeuLeuGln

34TF10 STOP
              ▼                                                          240
34TF    GlyLeuPhe•••----------------------------------------------
34TF    GGATTATTTTGAAGATATAGATTTAAGAAACCCCGAGCAGATTATTGTTTATGTTGGTGG
          X  X     X   XXX        XX        XXX  X  X  XX         XX
PPR     GGACTACTTTGGAGACTGAGATTTAGAAAACCTAAATCAAAAGATTGTTTATGTTGGTTT
PPR     GlyLeuLeuTrpArgLeuArgPheArgLysProLysSerLysAspCysLeuCysTrpPhe
                                                    *       *

360
34TF    ------------------------------------------------------------
34TF    TGTTGCAGATTCTATTATTGGCAGTTGCAATCTACATTATCAATAACTACTGCTTAG
            X          X                  X        X  XX
PPR     TGCTGCAGATTATATTATTGGCAGTTGCAGTCTACATTATCCATAGATACTGCTTAG
PPR     CysCysArgLeuTyrTyrTrpGlnLeuGlnSerThrLeuSerIleAspThrAla•••
          *  *                                                 ▲
                                                          PPR STOP
```

FIG. 7

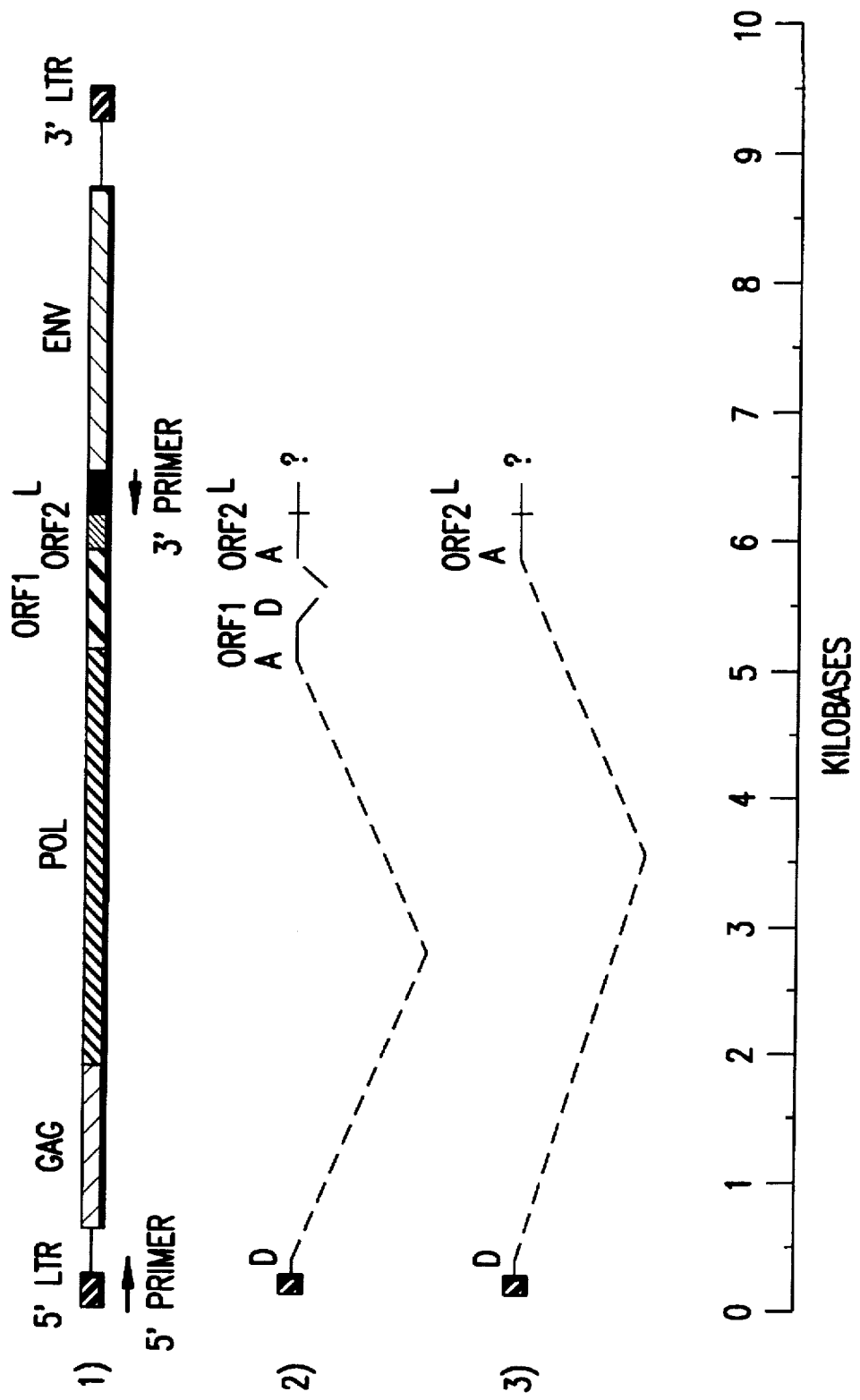

U3 →
CTGGATGAGTACTGGAACCCTGAAGAAATAGCTTATGGACTAGGACTGTTTACGAACAACAATGATAAAGGAAATAGCTGAGCTGACTCATAGTTAAAGCGCTAGCAGCT
                                50                                                100      R

GCTTAACCGCCAAACCACATCCTATGTAAAGCTTGCTCTAATGACGTATAAGTTGTTCCATTGTAAGAGTATATAACCAGTGCTTTGTGAAACTTCGAGGAGTCTCTTGTTGAGGACTTTT
                                150                                               200                              U5 →
                        R → U5

GAGTTCTCCCTGAGGCTCCCACCAGATACAATAAATATTTGAGATTGAACCCTGTCGAGTATCTGTGTAATCTTTTTTACCTGTGAGGTCTCGGAATCCGGGCCGAGAACTTCGCAGTTG
250                                           300                                 350

GCGCCCGAACAGGACTTGATTGAGAGTGAAGCTAGAAGCTAGAACCTGTTAAGCACAACAATAGAAAGCTGTTAAGCACAACTCCTCGCTGACCTAAATAGGGAAGCAGTAGCACACGCTAACACAGTG
                                400                                               450

AGTATCTCTAGTGAAGCAGCATCGAGCTCATAATCAAGTCATTGTTTAAAGCCCCAGATAATTACATCTGGTGACTCTTCCGCGACCTTCAAGCCAGGAGATTCGCCGAGGACACTCA
                                500                                               550                              600
                        GAG →
                                                                    METGlyAsnGlyGlnGlyArgAspTrpLysMetAlaIleLysArgCysSerAsnValAlaValGlyValGlyLysLysPheGly
ACAAGGTAGGAGAGATTCTACAGCAACATGGGGAATGGCAGGGCCGAGATTGGAAAATGGCCATTAAGAGATGTAGTAATGTTGCTGTAGGAGTAGGGGGAAGAGTAAAAATTTGGA
                                650                                               700

GluGlyAsnPheArgTrpAlaIleArgMetAlaAsnValSerThrGlyArgGluProGlyAspIleProGluThrLeuArgLeuValArgCysAspLeuGlnLeuLysLysPheArg
CAACGGAATTTCAGATGGGCCATTAGAATGGCTAATGTATCTACAGGAGACGGAGACCTGTGTATATACCAGAGACTTAGATAACTAAGGTTGGTTATTTGCCATTTACAAGAAACAAGAAGA
                                750                                               800

```
ENV→  METAlaGluGlyPheAlaAlaAsnArgGlnTrpIleGlyProGluGlyAlaGluLeuLeuAspPheAspIleAlaThrGlnMetSerGluGlu
TAATTTCATTTGCAACAATAAGAATGGCAGAAGGATTTGCAGCCAATAGACAAGAGCAAGCTGAAGAGTTATTAGATTTTGATATAGCAACACAAATGAGTGAAGAA
     6250                                                                    6350
GlyProLeuAsnProGlyValAsnProPheArgValProGlyIleThrGluLysLeuThrGluLysGluLysGlnAsnLeuArgAsnIleLeuGlnAspLeuArgAsnIleLeuGlnGlu
GGACCACTAAATCCAGGAGTAAACCCATTTAGGGTACCTGGAATAACACAGAAAAAGAAAGAACAAAACTAAGAAATATACAACTACAAGATCTAAGGAACAAATTCAAGAG
     6400                                                                    6450
GlyProLeuAsnProGlyValAsnProPheArgValProGlyIleThrGlnLysLysLysLysGlnAsnTyrCysAsnIleLeuGlnAspLeuArgAsnIleLeuGlnGlu
GGACCACTAAATCCAGGAGTAAACCCATTTAGGGTACCTGGAATAACACAGAAAAAGAAAGCAAAACTAAGAAATATACAACTACAAGATCTAAGAAATATATTACAAGAG
ValLysLeuGluGluGlyAsnAlaGlyLysPheArgArgAlaArgPheLeuArgSerArgAspArgPheIleGlyTyrCysIleTyrLeuGlyLysAsn
GTAAAACTGGAAGAAGGAAATGCAGGTAAGTTCAGAAGAGCAAGATTTCTGATGAACGTGTATTGTCCCTGGTTCATGCGTTCATAGGATATTGTATATATTTAGGTAAT
     6500                                                                    6550                                                                6600
ArgAsnLysLeuGlySerIleArgHisAspIleAspIleGluAlaProGlnGluGluLysGlyThrThrAspAsnIleLysThrIleLysAsnIleAsnIleLysAsn
CGAAATAAGTTAGGATCTAGAACATCGATGACATAGAAGCACCCCAAGAAGAAAAAGGAACTACAGATAATATAAAAATATGGCTAGACGATGCCTA
                                                   6650                                                                   6700
AsnGlyAspPheValSerArgAspPheIleLeuLeuTyrSerAsnSerIleValIleTyrSerGlnIleTyrArgLeuProIleArgArgSerGlySerMetGluThrSerSerProSerArgArgIleArgAsnA
GGAACGGTGACTTTGTATCTCGATTTTATTCTGATTTTATTCTGATTACATGGGATATGAACATAAAGACAGGAGCGCCCAGTAGTCCCAGTAGTCCCATTAGTCCCAGCAGTCCCATTGTAGAGTCCAGAAGAATCAGAAATA
                                                   6750                                                                                                   6800
snPheLeuGlyLeuLeuGlyThrArgArgThrAlaProGluGluAspProAlaCysGlnAspPheLeuGlySerTrpGlyAsnAspThrSerLysSer***
ATTTTTGGGATTGTTGGGCACCAGAAGAACCCGTCAGGACTTTCTTGGGTCAATGATACATCTAAAAAGCTAAGACAACAAATATAAGTATACGAGAGGAGGACTACCTTGGGAATTGG
     6850                                                                                                      6950
```

AlaArgGluIleTrpAlaThrLeuPheLysLysAlaAlaThrArgGlnCysArgArgGlyProSerGlyCysAlaAsnAsnThrCys
GCTAGAGAAATATGGGCAACATTATTCAAAAAGGCTACTAGACAATGTAGAAGAGGCAGAATGGAAAAGATGAGACTATAACAGGACCTCAGGATGCTAATAACACATGT
                    7000                                                    7050

TyrAsnValSerValIleValProAspTyrGlnCysTyrLeuAspThrTrpAsnGlyLysIleAsnIleSerLueCysLeuThrGlyLysMetLeuTyrAsnLys
TATAATGTTTCAGTAATAGTACCTGATTATCAGTGTTATTTAGATACATGGAATGGGAAATAAATATCATTATGTCTAACAGGAGGAAAAATGTGTACAATAAA
                    7100                                                    7150                    7200

ValThrLysGlnLeuSerTyrTyrCysThrAspProLeuIleAsnTyrThrCysPheGlyProAsnGlnThrCysMetTrpAsnArgThrGlnIleGlySerTrpPheArgAlaIleSerProGlyIlePro
GTTACAAAACAATTAAGCTATTACTGTACAGACCCATTAATAAACTACACTTGTTTTGGACCTAATCAACATGTAGTGGAATACATGTGGAATAGAACACAGATTAGGGAGCTGGTTTAGAGCAATCTCG
                                                            7250                                                    7300

LysCysGlyGlyTrpTrpAsnArgGlnTrpGluTrpArgProAspPheLysSerLysLysValLysIleSerGlnThrLysAsnSerThrLysAsnSerLysLysIleSerGlyGlnTrpPheArgAlaIleSer
AAATGTGGATGGTGGAATCAAAGATGGGAGTGGAGACCAGATTTTAAAAGTAAAAAGGTAAAAATATCTCAAACAAAGAACAGCAGTTCATTGTCAAAGAACACAGAGTCAATGAGAAGTTCAGGAGAT
                    7450                                                    7400                                                    7550

SerTrpLysAsnArgTrpGluTrpArgProAspPheLysSerLysLysValLysIleSerGlnThrLysAsnSerThrLysAsnSerLysLysIleSerAspThrSerLeu
TCATGGAAAAACAGAAATAGAATGGGAGTGGAGACCAGATTTTAAAAGTAAAAAGGTAAAAATATCTCAAACAAASAACCTAACCTTTGCAATGAGAAGTTCAGGAGAT
                                                            7550

TyrGlyGluValThrGlyAlaTrpIleGluPheGlyCysHisArgAsnLysHisThrGluAlaArgPheArgIleArgCysArgArgPheThrLysValAspAspSerLeu
TATGGAGAAGTAACGGGAGCTTGGATAGAGTTTGGATGTCATAGAAATAAGCATACTGAAGCAAGGTTTAGAATTAGATGTAGATGGAATGAGGAGTGATACCTGCTC
                    7600                                                    7650

IleAspThrCysGlyLysAsnThrProAsnValSerGlyAlaAsnProValAspCysSerThrMetTyrAsnCysSerLeuGlnAsnGlyPheThrMetLysValAspAsp
ATTGATACATGTGGAAACACTCCAAATGTTTCAGGTGCGAATCCTGTAGATTGTAGCACTATGTACAATTGTTCTTTACAAAACGGGTTTACTATGAAGGTAGATGAC
                                                            7750                                                    7800

FIG.9G

```
IleGluGlnAsnAsnValGlnGlyIleGlyLysThrGlyIleGluGlnLeuGlnTyrLeuLysGlyIleAsnIleProGlnTyrLeuLysGlyGlyIleLeu
ATAGAACAAAATAATGTACAAGGGATAGGAAAACAGGAATAGAACAATTACAAAAGTGGGAAGATGGAAGATTAAAAAGTATTCCACAATATTTAAAGGACTATTGGGAGGTATCTTG
                          8550                                          8600
GlyIleGlyLeuGlyValLeuLeuLeuIleLeuLysLeuProThrLeuValAspCysIleArgAsnCysIleHisLysIleLeuGlyIleTyrThrValIleAlaMetProGluValGlyIleGly
GGAATAGGATTAGGAGTGTTATTATTGATTTTATGTTACCTACATTGGTTGATTGTATTAGAAACTGTATCCACAAGATACACAGTAATTCCAATGCCTGAAGTAGAAGGA
                          8650                                          8700                                8750
GluGluIleGlnProGlnMetGluLeuArgAsnGlyArgAsnGlyGlyMetSerGluLysGluGlu***                     ***GlyLysArgGlnArgArgArgLysLysGluLeuSerLeuGln
                                                                                         ***LysGluLysThrLysLysLysGluLeuSerLeuGln
GAAGAAATACAACCACAAATGGAATTGAGGAGAAATGGTAGGCAATGTCGAAGAAATGAAGTATCTCAGACTTATTTTATAACGGAGATACTGTCCTGAGT
                          8800                                          8850                                9000
                                                                                                                 ***GlyLysArgGlnArgArgArgLysLysGluAlaPheLy
                                                                                                                 ***LysGluLysThrLysLysLysGluLeuSerLeuGln
TCTTCCCTTTGAGGAAGTATGTCATATGAATCCATTTCGAATCAAATCAAACTAAACTAAAGTATGTATTCTAAGGTAAAAGCAAAAGAAGAAGAAGAAAGCCTTCAA
                          8900                                          8950
sArgMetMetThrGluLeuAspArgPheArgLysLeuPheGlyAspArgPheArgLysLeuGlnGluLeuAlaIleTrpHisAspPheTyrAsnGlyArgGlnPheAsnGlyArgPhe***
GluAspAspAspAspArgValArgArgAspAspArgSerLeuGlnGluLeuAlaIleTrpHisAspPheTyrAsnGlyArgGlnPheAsnGlyArgPhe***
GAGGATGATGACAGAGAGTTAGAAGATCGCTTCAGGAAGCTATTTGGCACGACGACTTCTACAACCGGACGACAGCACCAGTAGATTCTGAAGATGAACCTCCTAAAAAAAGAAAAGAAAAGGGTGGACTG
                          9050                                          9100
pAspGluTyrTrpAsnProGluGluIleGluArgMetLeuMetAsp***
GGATGAGTACTGGAACCCTGAAGAAATAGAAAGAATGCTTATGGACTAGGGACTGTTTACGAACAACAAATGATAAAAGGAAATAGCTGACGCATGACTCATAGTTAAAGCCCTAGCCAGCTGCT
                          9150                                          9200
```

FIG.9H

```
TAACCCCAAAACCACATCCTATGTAAAGCTTGCTAATGACGTATAAGTTGTTCCATTGTAAGAGTATATAACCAGTGCTTGTGAAACTTCGAGGAGTCTCTTTGTTGAGGACTTTTGAG
          9250                                                  9300                                                  9350

TTCTCCCTTGAGGCTCCCACAGATACAATAAATATTTGAGATTGAACCCTGTCGAGTATCTGTGTAATCTTTTTTACCTGTGAGGTCTCGGAATCCGGGCCGAGAACTTCGCAG
          9400                                                  9450
```

FIG. 9I

```
   1 TGGGATGAGT ATTGGGACCC TGAAGAAATA GAAAGAATGC TTATGGACTA AGAACTGTCA
  61 CAAACAAATG ATAAATGGAA ACAGCTGAAC ATGACTCATA GTTAAAGCGC TAGCAGCTGC
 121 TTAACCGCAA AACCACATCC TATGTAAAGC TTGCCAATGA CGTATAATTT GCTCCACTGT
 181 AAGAGTATAT AATCAGTGCT TTGTGAAGCT TCGAAGAGTC TCTCTGCTGA GGACTTTCGA
 241 GTTCTCCCTT GAGGCTCCCA CAGATACAAT AAATATTTGA GATTGAACCC TGTCAAGTAT
 301 CTGTGTAGTC TTTTCTACCT GTGAGGTCTC GGAATCCGGG CCGAGAACTT CGCAGTTGGC
 361 GCCCGAACAG GGACTTGAGA AAGAGTGATT GAGGAAGTGA AGCTAGAGCA GTAGAAAGCT
 421 GTTAAGCAGA ACTCCTGTTG ACCTAAATAG GGAAGCAGTA GCAGACGCTG CTAAACAGTG
 481 AGTATCTCTA GTGAAGCAGA CTCGAGCTCA TAATCAAGTC ACTGTTTAAA GGCCCAGATA
 541 AATTACATTT GGTGACTCTT CGCGGACCTT CAAGCCAGGA GATTCGCCGA GGGACAGCTA
 601 ACAAGGTAGG AGAGACTCTA CAGCAACATG GGGAATGGAC AGGGGCGAGA TTGGAAAATG
 661 GCCATTAAGA GATGTAGTAA TGTTGCTGTA GGAGTAGGGG GGAAGAGTAA AAAATTTGGA
 721 GAGGGGAATT TTAGGTGGGC CATAAGAATG GCTAATGTAT CTACAGGACG AGAACCTGGT
 781 GATATACCAG AGACTTTAGA TCAACTAAGG TTGGTTATTT GCGATTTACA AGAAAGAAGA
 841 GAAAAATTTG GATCTAGCAA AGAAATTGAC ATGGCAATTA CAACATTAAA AGTCTTTGCA
 901 GTAGTGGGAC TTTTAAATAT GACAGTGTCT ACTGCTGCTG CAGCTGAAAA TATGTATACT
 961 CAGATGGGAT TAGACACTAG ACCGTCTACA AAAGAAGCGG GAGGAAAAGA TATGTATACT
1021 CCACAGGCAT ATCCTATTCA AACAGTAAAT GGAGCACCAC AATATGTAGC ACTTGACCCA
1081 AAAATGGTGT CCATTTTTAT GGAAAAGGCA AGAGAGGGAT TAGGAGGTGA GGAAGTTCAA
1141 CTATGGTTTA CAGCCTTCTC TGCAAATTTA ACACCTACTG ACATGGCCAC ATTAATAATG
1201 GCCGCACCCG GGTGCGCTGC AGATAAAGAA ATATTGGATG AAAGCTTAAA GCAATTGACA
1261 GCAGAATATG ATCGGACAAA TCCCCCTGAT GGTCCTAGAC CATTACCCTA TTTTACTGCA
1321 GCAGAAATTA TGGGTATAGG ATTAACTCAA GAACAACAAG CAGAAGCAAG ATTTGCACCA
1381 GCTAGGATGC AATGTAGAGC ATGGTATCTT GAGGCATTAG GAAAATTAGC CGCCATAAAG
1441 GCTAAATCTC CTCGAGCTGT GCAGTTAAGA CAAGGAGCTA AGGAAGATTA TTCATCCTTT
1501 ATAGACAGAT TGTTTGCCCA AATAGATCAA GAACAAAATA CAGCTGAAGT TAAGTTATAT
1561 CTAAAACAGT CATTAAGCAT AGCTAATGCT AATGCAGAAT GCAAAAGGC AATGAGTCAT
1621 CTTAAGCCAG AAAGTACCCT AGAAGAAAAG TTGAGAGCTT GTCAAGAGAT AGGATCCCCA
1681 GGATATAAAA TGCAACTCTT GGCAGAAGCT CTTACAAAAG TTCAAGTAGT GCAATCAAAA
1741 GGATCAGGAC CAGTGTGTTT TAATTGTAAA AAACCAGGGC ATCTAGCAAG ACAGTGTAGA
1801 GATGTGAAAA AATGTAATAA ATGTGGAAAA CCTGGTCATT TAGCTGCCAA ATGTTGGCAA
1861 GGTGGTAAAA GAAATTCGGG AAACTGGAAG GCGGGGCGAG CTGCAGCCCC AGTGAATCAA
1921 GTGCAGCAAA GACTAATGCC ATCTGCACCT CCAATGGAGG AAAAATTATT GGATTTATAA
1981 ATTACAATAA AGTAGGTACT ACTACATCAT TAGAAAAGAG GCCAGAAATA CTTATATTTG
2041 TGAATGGGTA CCCTATAAAA TTTTTATTAG ATACAGGAGC AGATATAACA ATTTTAAATA
2101 GGAGAGATTT TCAAGTAAAA AACTCTATAG AAAATGGAAG ACAAAATATG ATTGGAGTAG
2161 GGGGAGGAAA GAGAGGAACA AATTATATCA ATGTGCATTT AGAGATTAGA GATGAAAATT
2221 ACAAGACACA ATGTATATTT GGCAATGTTT GTGTCTTAGA AGATAACTCA TTAATACAAC
2281 CATTATTAGG GAGAGATAAT ATGATTAAAT TTAATATCAG GTTAGTAATG GCTCAAATTT
2341 CTGATAAGAT TCCAATAGTA AAAGTAAAGA TGAAGGATCC TAATAAAGGA CCTCAAATAA
2401 AACAATGGCC ATTATCAAAT GAAAAAATTG AAGCTTTAAC AGAAATAGTA GAAAGACTAG
2461 AAAGGGAAGG GAAAGTAAAA AGAGCAGATC CAAATAATCC ATGGAATACA CCAGTATTTG
2521 CTATAAAAAA GAAAAGTGGA AAATGGAGGA TGCTCATAGA TTTTAGAGAA TTGAACAAAT
2581 TAACTGAGAA AGGAGCAGAA GTCCAGTTGG GACTACCTCA CCCTGCTGGT TTACAAATGA
```

FIG. 10A

```
2641  AAAAACAAAT AACAGTATTA GATATAGGGG ATGCATATTT CACCAATCCC CTTGACCCAG
2701  ATTATGCTCC TTATACAGCA TTTACTTTAC CTAGGAAGAA TAATGCGGGA CCAGGAAGAA
2761  GATTTGTGTG GTGTAGTCTA CCACAAGGCT GGATTTTAAG TCCATTGATA TATCAAAGTA
2821  CATTAGATAA TATAATACAA CCTTTTATTA GACAAAATCC TCAATTAGAT ATTTATCAAT
2881  ATATGGATGA CATTTATATA GGATCAAACT TAAGTAAAAA GGAGCATAAA GAAAAAGTAG
2941  AAGAATTAAG AAAATTACTA TTATGGTGGG GATTTGAAAC TCCAGAGGAT AAATTACAGG
3001  AAGAACCCCC ATATAAATGG ATGGGTTATG AATTACATCC ATTAACATGG ACAATACAAC
3061  AGAAACAGTT AGAAATTCCA GAAAAGCCTA CATTAAATGA ATTACAAAAA TTAGCAGGAA
3121  AAATTAATTG GGCTAGCCAA ACTATTCCAG AATTAAGTAT AAAATCATTA ACTAACATGA
3181  CGAGAGGAAA TCAAAACCTA AATTCAACAA GAGAGTGGAC TGAGGAAGCT AGACTAGAAG
3241  TACAGAAGGC CAAAAGGGCT ATTGAAGAAC AAGTACAACT AGGATATTAT GACCCTAGTA
3301  AAGAATTGTA TGCTAAATTA AGCTTAGTGG GACCACATCA AATAAGTTAT CAAGTATATC
3361  AGAAGTGTCC AGAAAAGATC TTATGGTATG GAAAAATGAG TAGGCAAAAG AAAAAGGCAG
3421  AAAATACGTG TGATATAGCG TTAAGAGCAT GCTACAAAAT AAGGGAAGAA TCCATTATAA
3481  GAATAGGAAA AGAACCAAGA TATGAAATAC CTACTTCTAG AGAAGCCTGG GAATCAAATT
3541  TAATTAATTC ACCATATCTT AAAGCCCCAC CTCCAGAAGT AGACTATATC CATGCTGCTT
3601  TAAACATAAA AAGAGCACTA AGTATGATAA AAGATCCTCC AATATCAGGA GCAGAAACGT
3661  GGTATATAGA TGGAGGTAGA AAGCTAGGAA AAGCAGCAAA AGCAGCCTAT TGGACAGATA
3721  CAGGAAAGTG GCAAGTAATG GAATTAGAAG GTAGTAATCA GAAGGCGGAA ATACAAGCAT
3781  TATTATTGGC ATTAAAGGCA GGACCAGAGG AAATGAATAT TATAACAGAT TCTCAGTATA
3841  TGATAAATAT TCTTAGTCAA CAACCAGATA AGATGGAAGG AATCTGGCAA GAAGTTTTAG
3901  AAGAATTGGA AAAGAAAACA GCAATATTTA TAGATTGGGT CCCAGGACAT AAAGGTATTC
3961  CAGGAAATGA GGAAGTAGAT AAGCTTTGTC AAACAATGAT GATAATAGAA GGGGATGGGA
4021  TATTAGATAA AAGAACAGAA GATGCAGGAT ATGATTTATT AGCTGCAAAA GAAATACATC
4081  TATTACCAGG AGAGGTAAAA GTAATACCAA CGGGAGTAAA ACTAATGTTG CCTAAAGGAC
4141  ATTGGGGATT AATAATGGGA AAAAGCTCGA TAGGGAGTAA AGGATTGGAT GTATTAGGAG
4201  GGGTAATAGA TGAAGGATAT CGAGGTGAAA TTGGAGTAAT AATGATTAAT TTATCAAAAA
4261  AATCAATCAC TTTGTTGGAA CAACAGAAGA TAGCACAATT AATAATATTG CCTCATAAAC
4321  ATGAAGCATT AGAACAGGGG AAAGTAGTAA TGGATTCAGA GAGAGGAGAA AAAGGTTATG
4381  GGTCAACAGG AGTATTCTCC TCTTGGGTTG ACAGAATTGA GGAAGCAGAA ACAAATCATG
4441  AAAAATTTCA CTCAGATCCG CAATACTTAA GGACTGAATT TAATTTACCC AAGATGGTGG
4501  CAGAAGAGAT AAGACGAAAA TGCCCTGTAT GTAGGATTAG AGGAGAACAA GTGGGAGGGC
4561  AATTGAAGAT AGGGCCTGGT ATCTGGCAAA TGGATTGCAC ACACTTTGAT GGCAAAATAA
4621  TTCTTGTGGC TATACATGTG GAATCAGGAT ATATATGGGC ACAAATAATC TCTCAAGAAA
4681  CTGCTGATTG TACAGTTAAA GCTGTCTTAC AATTATTGAG TGCTCATATT GTTACGGAGT
4741  TACAAACAGA TAATGGACCA AATTTTAAAA ATCAAAAGAT GGAAGGAGTA CTCAATTATA
4801  TGGGTGTGAA ACATAAGTTT GGTATCCCAG GAAACCCACA ATCACAAGCA TTAGTTGAAA
4861  ATGTAAATCA GACATTAAAA GTCTGGGTTC ACAAATTTTT GCCTGAAACA ACCTCCTTGG
4921  ATAATGCATT AGCTCTCGCT GTGCATTGTC TCAATTTTAA ACAAAGGGGT AGAATAGGAG
4981  GGATGGCCCC TTATGAATTA TTAGCACAAC AAGAATCCTT AAGAATACAA GATTATTTCT
5041  CTGCAATACC ACAAAAATTG CAAGCACAAT GGATTTATTA TAAAGATCAA AAAGATAAGA
5101  AATGGAAAGG GCCAATGAGA GTAGAATACT GGGGACAAGG ATCAGTGTTA TTAAAGGATG
5161  AAGAGAAGGG ATATTTTCTT ATACCTAGGA GACACGTAAA GAGAGTCCCA GAACCCTGCG
5221  CTCTTCCTGA AGGGGATGAG TGACGAAGAT TGGCAGGTAA GTAGAAGACT CTTTGCAGTG
```

FIG. 10B

```
5281  CTCCAAGGAG GGGTATATAA CGCTATGCTA TATATATCTA GACTACCTCA GGACGAAAGA
5341  GAAAAATATA AAAAGGATTT CAAGAAAAGA CTTTTAGATA CAGAAACAGG ATTTATAAAA
5401  AGACTAAGGA AAGCTGAAGG AATAAAATGG AGCTTTCATA CTAGAGATTA TCATGTAGGA
5461  TATGTTAGAG AAATGGTAGC AGGACCCACT ACACCACATA GTCTAAGGCT GTATGTGTAT
5521  ATAAGTAATC CACTATGGCA TTCTCAGTAT GCTCCAGGCT TGGTAAATTT TAATAAGGAA
5581  TGGCCTTTTG TAAATCTATG GATAAAAACA GGATTTATGT GGGATGATAT TGAAAAACAA
5641  AATATTTGTA TAGGAGGAGA AGTTTCACCA GGATGGGGAC CTGGGATGAT AGGTATAGCG
5701  ATAAAAGCTT TTAGTTGTGG CGAAAGAAAG ATTGAGGCTA CTCCTGTAAT GATTATAAGA
5761  GGAGAAATAA ATCCAAAAAA ATGGTGTGGA GACTGTTGGA ATTTGATGTG TCTTAGAAAC
5821  TCACCTCCAG AGACTTTACA AAGGCTCGCT ATGTTGGCAT GTGGAGTACA GGCTAAGAGC
5881  TGGCGAGGAT GCTGTAATCA ACGTTTTGTT TCTCCTTACA GAACACCTGC TGATTTAGAG
5941  GTTATTCAAT CCAAACCCGG CTGGTGCATG TTATGGCGAG AAGCAGCCAT CAGGATATTT
6001  ATACGGATAT TTAATAAGGT CGCTGAAAGA TTAGACAAGG AAGCAGCCAT CAGGATATTT
6061  GTATTAGCAC ATCAATTAGA GAGGGATAAA TTGATTAGAC TTCTGCAAGG ACTACTTTGG
6121  AGACTGAGAT TTAGAAAACC TAAATCAAAA GATTGTTTAT GTTGGTTTTG CTGCAGATTA
6181  TATTATTGGC AGTTGCAGTC TACATTATCC ATAGATACTG CTTAGAAATA TTTATAATAA
6241  TATTTCATTT GCAACAATAA TTATGGCAGA AGGGTTTGCA GCCAATAGAC AATGGATAGG
6301  GCCAGAAGAA GCTGAAGAGC TATTAGATTT TGATAAAGCA ACACAAATGA ATGAAGAAGG
6361  GCCACTAAAT CCAGGAGTAA ACCCATTTAG AGTACCTGCA GTAACAGAAG CAGACAAGCA
6421  AGAATATTGT AAGATATTAC AACCCCGATT ACAAGAGATA AGGAATGAAA TTCAAGAAGT
6481  AAAACTAGAA GAAGGAAATG CAGGTAAGTT TAGAAGAGCA AGATTCTTGA GATATTCTGA
6541  TGAAAGTATA TTATCCTTAA TTCATTTGTT CATAGGGTAT TGTACATACT TAGTAAATAG
6601  AAGGAGGTTA GGATCTTTAA GGCATGACAT AAATATAGAA GCGCCTCAAG AAGAGCAGTA
6661  TAGCAGTAGA GAGCAGGGCA CAACTGAGAA TATAAAATAT GGTAGACGAT GCTTGATAGG
6721  AACAGCAAGT CTGTACTTGT TGCTTTTTAT TGCTTTTTAT AGGAGTGGCA ATATATTTAG
6781  TGCTCAGATA GTATGGAGAC TTCCACCATT AGTAGTCCCA GTAGAAGAAT CAGAAATAAT
6841  TTTTTGGGAT TGTTGGGCAC CAGAGGAGCC CGCCTGTCAA GACTTTCTTG GGCAATGAT
6901  ACATCTAAAA GCTAGTACAA ATATAAGTAT ACAAGAAGGA CCTACCTTGG GGAATTGGGC
6961  TAGAGAAATA TGGGGAACAT TATTCAAAAA AGCTACTAGA CATTGTAGGA GAAATAAAAT
7021  ATGGAAAAGG TGGAATGAAA CTATAACAGG ACCAGTAGGA TGTGCTAATA ATACATGTTA
7081  TAATATCTCT GTAATAATAC CTGATTATCA ATGTTATCTA GATAGAGTAG ATACTTGGTT
7141  ACAAGGGAAA GTAAATATAT CATTATGCCT AACAGGAGGA AAAATGTTGT ATAATAGAGA
7201  TACAAAACAA TTAAGCTATT GTACAGACCC ATTACAAATC CCACTGATCA ATTATACATT
7261  TGGGCCTAAT CAAACATGTA TGTGGAACAC TTCACAGATT CAAGACCCGG AGATACCAAA
7321  ATGTGGATGG TGGAATCAAA TAGCCTATTA TAACAGTTGT AGATGGGAAA GCACAAATGT
7381  AAAGTTTTAT TGTCAAAGAA CACAGAGTCA GCCTGGAACA TGGATTAGAA CAATCTCATC
7441  ATGGAGACAA AAGAATAGAT GGGAATGGAG ACCAGACTTT GAAAGCGAAA AAGTTAAAAT
7501  ATCATTACAA TGTAATAGTA CACATAATTT AACTTTTGCA ATGAGAAGTT CAGGAGATTA
7561  TGGAGAAGTA ATGGGAGCTT GGATAGAATT TGGATGTCAT AGGAACAAAT CAAGATTCCA
7621  TACTGAAGCA AGGTTTAGAA TTAGATGTAG ATGGAATGTA GGGGATAATA CCTCACTCAT
7681  TGATACATGT GGAAAAAATC TAAATGTTTC AGGTGCCAAT CCTGTAGATT GTACCATGTA
7741  TGCAAATAAA ATGTATAACT GTTCCTTACA AAACGGGTTT ACTATGAAGG TAGATGACCT
7801  TATTATGCAT TTCAATATGA CAAAAGCAGT AGAAATGTAT AACATTGCTG GGAATTGGTC
7861  TTGTAAATCT GATTTACCAC AAAATTGGGG ATATATGAAT TGTAATTGTA CGAATGGTAC
```

FIG. 10C

```
7921  GAGTAATGAC AATAAAATGG CATGTCCTGA AGATAAGGGT ATCTTTAAGA ATTGGTATAA
7981  TCCAGTAGCA GGATTAAGAC AAGCATTAGA AAAATATCAA GTGGTAAAAC AGCCAGAATA
8041  TATAGTAGTA CCAACAGAAG TTATGACCTA TAAATACAAA CAGAAAAGAG CAGCAATTCA
8101  TATTATGTTA GCTCTTGCAA CAGTATTGTC TATAGCTGGG GCAGGAACAG GTGCTACAGC
8161  AATTGGGATG GTGACTCAAT ATCAGCAAGT TTTAGCTACT CATCAAGAAG CATTGGATAA
8221  AATAACTGAA GCATTGAAAA TAAATAATTT AAGGTTAGTT ACTTTAGAGC ATCAAATGTT
8281  AGTCATAGGA TTGAAAGTAG AAGCTATAGA AAAATTTTTA TATACTGCTT TTGCTATGCA
8341  AGAACTAGGA TGTAATCAAA ATCAATTCTT TTGTGAAATT CCCAAAGAGC TATGGCTAAG
8401  GTATAATATG ACATTAAATC AAACAATTTG GAATCATGGA AATATAACTT TAGGGGAATG
8461  GTACAATCAG ACAAAATATT TACAACAAAA ATTTTATGAA ATAATTATGG ATATAGAACA
8521  AAATAATGTA CAAGGAAAAC AAGGATTACA AAAATTACAA AATTGGCAAG ATTGGATGGG
8581  ATGGATAGGA AAAATACCTC AATACTTAAA GGGACTCTTG GGAGGCATTT TGGGAATAGG
8641  TTTGGGAATT CTATTATTGA TTTTATGTTT ACCCACTTTA GTTGATTGTA TTAGAAATTG
8701  TATTAGTAAA GTTCTAGGAT ATACAGTAAT CGCAATGCCT GAGATAGATG ATGAAGAAGA
8761  AACGGTACAA ATGGAATTGA GGAAAAATGG CAGGCAATGT GGCATGTCTG AAAAAGAGGA
8821  GGAATGATGG AGTGCCTCAG AACTGCTTAA TGCAGGAGAG GTGCTGAGCT GATTTCTTCC
8881  CTTTGAGGAA GATATGTCAT ATGAATCCAT TTTGAATCAA ATAATAAGT ATTTGTATTA
8941  TAAGGTAAAA TGAAAAAGAA AAGACAAAGA AGAAGAAGAA AGAAGAAGGC CTTTAAGAAA
9001  ATGATGACAG ATTTAGAAGA CCGCTTCAGA AAACTATTCG GCTCACCCTC TAAAGATGAA
9061  TACACAGAAA TTGAGATAGA AGAAGACCCT CCTAAAAAAG AAAAAAGGGT GGACTGGGAT
9121  GAGTATTGGG ACCCTGAAGA AATAGAAAGA ATGCTTATGG ACTAAGAACT GTCACAAACA
9181  AATGATAAAT GGAAACAGCT GAACATGACT CATAGTTAAA GCGCTAGCAG CTGCTTAACC
9241  GCAAAACCAC ATCCTATGTA AAGCTTGCCA ATGACGTATA ATTTGCTCCA CTGTAAGAGT
9301  ATATAATCAG TGCTTTGTGA AGCTTCGAAG AGTCTCTCTG CTGAGGACTT TCGAGTTCTC
9361  CCTTGAGGCT CCCACAGATA CAATAAATAT TTGAGATTGA ACCCTGTCAA GTATCTGTGT
9421  AGTCTTTTCT ACCTGTGAGG TCTCGGAATC CGGGCCGAGA ACTTCGCA
```

MOLECULAR CLONING AND CHARACTERIZATION OF THE FELINE IMMUNODEFICIENCY VIRUS ISOLATE PPR

This is a continuation of application Ser. No. 07/759,570 filed on Sep. 12, 1991, now abandoned.

This invention was made in part with government support under Public Health Service grants No. RO1 AI25825 and RO1 A28580 from the National Institutes of Health. The government may have certain rights in this invention.

FIELD OF THE INVENTION

The present invention relates generally to the protection from, and detection and treatment of, viral infection. More particularly, the invention relates to compositions and methods useful for the prevention, diagnosis, and treatment of infection by feline immunodeficiency virus (FIV).

BACKGROUND OF THE INVENTION

Domestic cats may become infected with several retroviruses, including feline immunodeficiency virus (FIV), feline leukemia/sarcoma virus (FeLV/FeSV), endogenous type C oncornavirus (RD-114), and feline syncytium-forming virus (FeSFV). Of these, FIV is a significant pathogen, causing diverse symptoms including lymphoreticular and myeloid neoplasms, anemias, immune-mediated disorders, and an immunodeficiency syndrome that is similar to human acquired immunodeficiency syndrome (AIDS).

Only recently isolated, FIV is present in 1.2% of low-risk cats and in 14% of high-risk cats. Cats that remain indoors have a low risk of FIV infection, while cats that roam outdoors have a much greater risk (Yamamoto, J. K. et al., J. Am. Vet. Med. Assoc., 194:213–220 (1989). Although FIV is not known to infect people, it is closely related to another retrovirus in the lentivirus subfamily, human immunodeficiency virus (HIV), the causative agent of AIDS. Since primates are difficult to obtain, the naturally occurring FIV in cats may serve as an attractive model for the study of human acquired immunodeficiency syndrome.

Since a long latency period may proceed natural FIV-induced immunosuppression, there is a need for diagnostic reagents that allow the identification of infected individuals in the absence of easily observed disease symptoms. Methods for treating and vaccinating against FIV infection are also needed.

A significant problem in developing treatments, vaccines, and diagnostics for many viral infections is that the outer surfaces of the virus particles change relatively rapidly. The components of the outer surface, being the portion of the virus particles that are exposed to an organism's immune system, are usually the antigenic targets of the immune response. Thus, changes in these outer surface components, most notably envelope proteins, often cause immunoglobulins that recognized the original virus particles to no longer recognize the particles having the changed outer surface. This provides a means for the virus to avoid being neutralized by antibodies that are present in the organism due to earlier infection by the original virus.

It is thus desirable to identify regions of the outer surfaces of viral particles that do not change rapidly, but rather remain similar among different isolates of a virus. As these conserved regions change much more slowly than other parts of the viral surface, the conserved regions are likely to be useful as targets for reagents useful for detecting, treating and vaccinating against a virus. The present invention fulfills these and other needs.

SUMMARY OF THE INVENTION

The present invention provides novel reagents for the detection and treatment of, and vaccination against, feline immunodeficiency virus (FIV) infection. One aspect of the invention is the identification of conserved regions of the FIV envelope protein, the amino acid sequences of such regions being quite similar among different isolates of FIV.

The invention includes substantially purified polypeptides that have amino acid sequences substantially identical to: a) a polypeptide of the PPR clone of feline immunodeficiency virus (FIV), the polypeptide having at least one antigenic determinant recognized by immunoglobulins specific for the PPR clone of FIV polypeptide; or b) polypeptide fragments from either a conserved or variable region of an FIV envelope protein. Immunoglobulins that specifically recognize the polypeptides or portions of the polypeptides described above are also within the scope of the invention, as are methods for using these immunoglobulins to detect the presence of FIV or related viruses in physiological samples, and methods to treat or vaccinate animals infected with FIV or related viruses.

Nucleic acids that have sequences substantially identical to, or substantially complementary to, nucleic acids that code for the above polypeptides, polypeptide fragments, or immunoglobulins are also within the scope of the invention. The invention also includes cell lines that contain these nucleic acids, such cell lines being useful for producing partial or complete viral polypeptides, or virus particles. The nucleic acids included in the invention are also useful as probes to detect the presence of viral nucleic acids in physiological samples.

Vaccines against FIV and related viruses, as well as methods of producing such vaccines, are also included in the invention. The vaccines may be compositions that include virus particles of the PPR isolate of FIV, or polypeptides or immunoglobulins described above, and a pharmaceutically acceptable carrier. Vaccines also include virus particles or bacterial or other host cells that contain nucleic acids or polypeptides which are included in the invention. The vaccines may be administered to animals at risk of infection by FIV or related viruses such as HIV.

A further aspect of the present invention includes kits for detecting FIV infection. Diagnostic kits may include polypeptides, oligonucleotides, or immunoglobulins, of the present invention that are useful as probes to detect the presence of FIV or related viruses. The kits may also include labels to aid detection of the viral particles or components.

BRIEF DESCRIPTION OF THE FIGURES

FIGS. 6A and 6B. Comparison of the deduced amino acid sequence of the env gene products from the 34TF10 and PPR clones of FIV. The vertical lines between amino acids indicate identity, two dots indicate a high degree of similarity, one dot shows a moderate degree of similarity, and a space represents dissimilar amino acids. Cysteines are indicated by small vertical arrows, while the brackets show potential glycosylation sites. The vertical arrowhead denotes the putative proteolytic cleavage site. SU, Major surface protein; TM, transmembrane protein. Horizontal lines are placed above the putative leader and the two presumed transmembrane regions (Trans Mem Reg 1 and 2).

FIG. 7. Comparison of nucleotide sequence and deduced amino acid sequence of ORF 2 from the 34TF10 and PPR clones of FIV. X's indicate nucleotide changes between the two clones. The amino acid changes between the two clones are underlined. Cysteine residues are represented by *, and stop codons are shown as three black dots.

FIG. 8. Identification of the splice donor and splice acceptor sites of the 34TF10 isolate of FIV. The major ORFs of FIV are represented in line 1. Locations of plus- and minus-strand PCR primers are indicated by arrows. Line 2 represents a subgenomic mRNA of the 34TF10 clone, with splice donor sites (D) at bases 604 and 5255 and splice acceptor sites (A) at bases 5188 and 5921. Line 3 represents another subgenomic mRNA species of the 34TF10 clone of FIV with a single splice donor site at base 604 and splice acceptor site at base 5921.

Figure 9C:
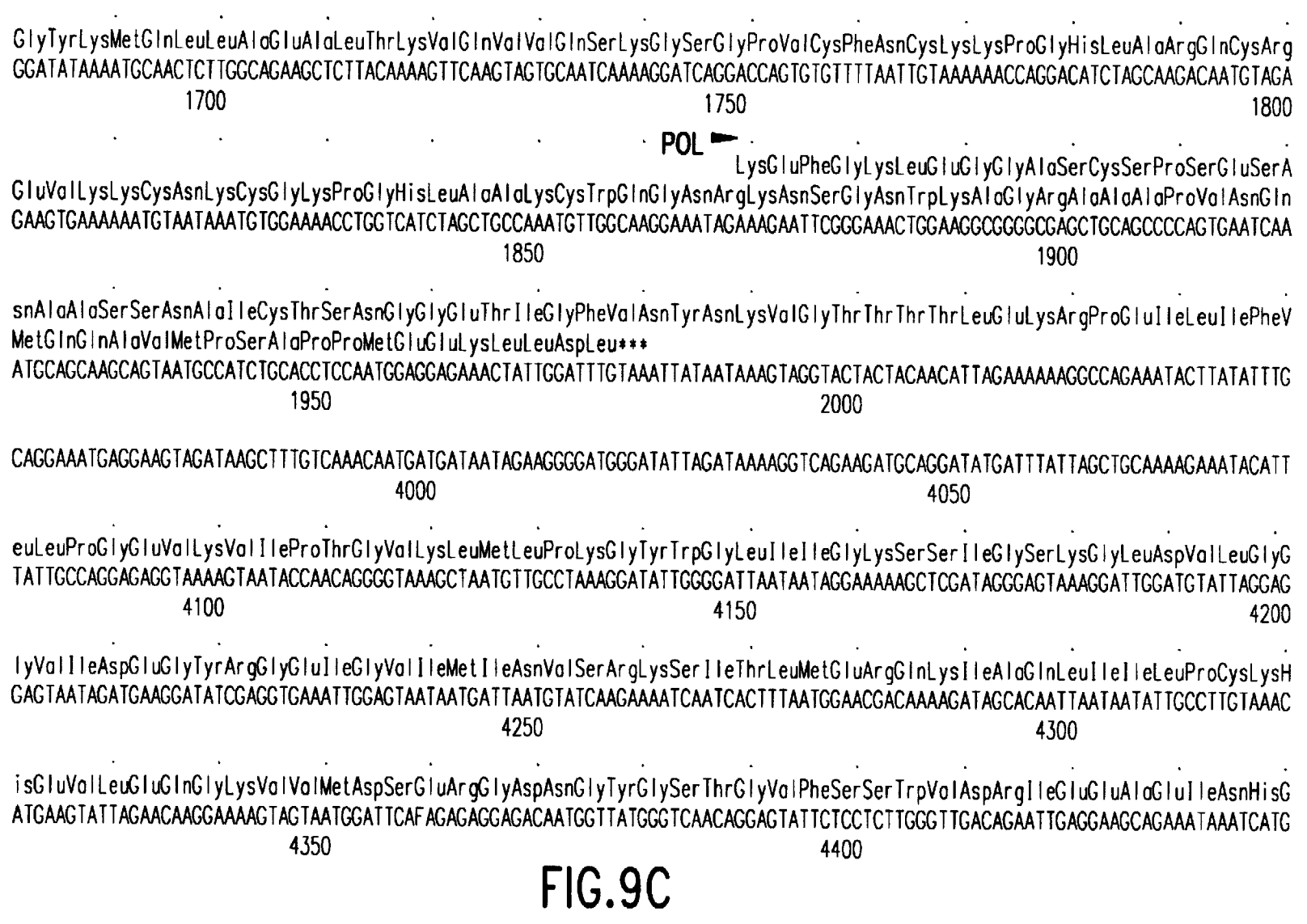

FIGS. 9A–L Nucleotide sequence of the PPR isolate of FIV, and deduced amino acid sequences of the major open reading frames. Arrows indicate the boundaries of the U3, R, and U5 regions of the LTR, and the translation start sites for the gag, pol and env open reading frames. The putative open reading frame for the vif is also indicated. Stop codons are indicated by "***". Deduced amino acid sequences for additional open reading frames are also shown.

FIGS. 10A–D. Nucleotide sequence of the PPR isolate of FIV.

DESCRIPTION OF THE SPECIFIC EMBODIMENTS

A. Definitions

A1. Proteins

Figure 1A:
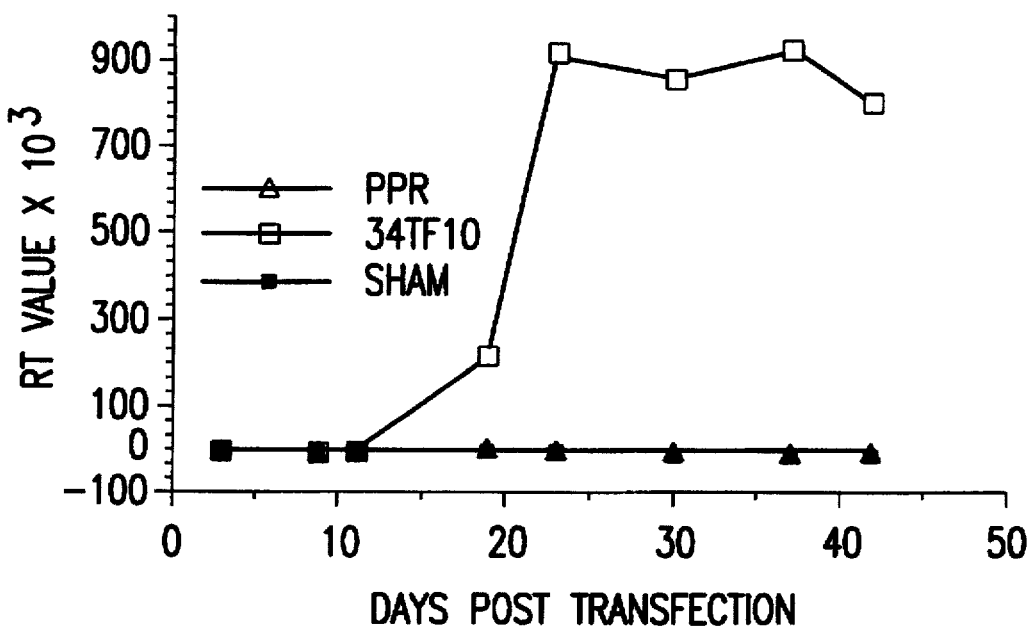
FIGS. 1A and B. Reverse transcriptase (RT) activity in culture supernatant after transfection with the molecular clones of FIV. The 34TF10 and PPR clones were separately transfected into noninfected G355-5 cells (D. Haapala et al., J. Virol. 53:827–833 (1985), incorporated herein by reference) by the calcium phosphate precipitation method (R. Sanchez-Pescador et al., Science 227:484–492 (1985), incorporated herein by reference). At 24 h posttransfection, noninfected PBLs were cocultivated with the transfected G355-5 cells for 24 h and then removed and cultured separately. The tissue culture supernatants from G355-5 cells FIG. 1A and PBLs FIG. 1B were monitored for $Mg^{2+}$-dependent reverse transcriptase activity (N. Pederson et al., Science 235:790–793 (1987), incorporated herein by reference). Expression of the PPR clone in G355-5 cells resulted in productive infection of PBLs during cocultivation. However, the PPR clone did not produce a detectable increase in RT activity in the G355-5 cells. In contrast, the 34TF10 clone established a productive infection in G355-5 cells after transfection. However, the amount of 34TF10 virus produced was insufficient to establish an infection in the cocultivated PBLs. Infection of PBLs by 34TF10 did occur but required a high multiplicity of infection.

The terms "peptide", "polypeptide" or "protein" are used interchangeably herein. The term "substantial identity", when referring to polypeptides, indicates that the polypeptide or protein in question is at least about 30% identical to an entire naturally occurring protein or a portion thereof, usually at least about 70% identical, and preferably at least about 95% identical.

As used herein, the terms "isolated", "substantially pure" and "substantially homogenous" are used interchangeably and describe a protein that has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially purified protein will typically comprise over about 85 to 90% of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized.

A polypeptide is substantially free of naturally-associated components when it is separated from the native contaminants which accompany it in its natural state. Thus, a polypeptide which is chemically synthesized or synthesized in a cellular system different from the cell from which it naturally originates will be substantially free from its naturally-associated components.

Proteins may be purified to substantial homogeneity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

A2. Nucleic Acids

Nucleic acids, as used herein, may be DNA or RNA. When referring to nucleic acids, the term "substantial identity" indicates that the sequences of two nucleic acids, or designated portions thereof, when optimally aligned and compared, are identical, with appropriate nucleotide insertions or deletions, in at least about 80% of the nucleotides, usually at least about 90% to 95%, and more preferably at least about 98 to 99.5% of the nucleotides.

Alternatively, substantial nucleic acid sequence identity exists when a nucleic acid segment will hybridize under selective hybridization conditions, to a complement of another nucleic acid strand.

"Substantially complementary" similarly means that one nucleic acid is identical to, or hybridizes selectively to, another nucleic acid. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, M. Kanehisa Nucleic Acids Res. 12:203 (1984), incorporated herein by reference.

Stringent hybridization conditions will typically include salt concentrations of less than about 1M, more usually less than about 500 mM and preferably less than about 200 mM. Temperature conditions will typically be greater than 22° C., more typically greater than about 30° C. and preferably in excess of about 37° C. As other factors may dramatically affect the stringency of hybridization, including base composition and size of the complementary strands, presence of organic solvents and extent of base mismatching, the combination of parameters is more important than the absolute measure of any one alone.

"Isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology*, Greene Publishing and Wiley-Interscience, New York (1987), incorporated herein by reference.

"Oligonucleotides" may be synthetic DNA fragments prepared, for example, by the phosphoramidite method described by Beaucage and Carruthers, Tetra. Letts. 22:1859–1862 (1981), or by the triester method according to Matteucci, et al., J. Am. Chem. Soc., 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence.

An oligonucleotide is substantially complementary to a target nucleic acid when it will anneal only to a single desired position on that target nucleic acid under conditions determined as described below. Proper annealing conditions depend, for example, upon an oligonucleotide's length, base composition, and the number of mismatches and their position on an oligonucleotide, and must often be determined empirically. For discussions of oligonucleotide design and annealing conditions, see, for example, Sambrook et al., *Molecular Cloning: A Laboratory Manual* (2nd ed.),. Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

"Antisense" oligonucleotides are useful in modulating gene expression or for eliminating it altogether. Such oligonucleotides are complementary to the coding or "sense" strand of a DNA sequence encoding a protein. The specific sequences to which such antisense oligonucleotides are complementary may be typically found in the coding region of the DNA sequence itself or in such noncoding regions as introns, promoter sequences, or other sequences in the 5' or 3' flanking regions of the gene. The choice of appropriate sequences, the length of antisense oligonucleotides, and other relevant information is well known in the art and described, for example, in Sherman, M. I. Annals of the New York Academy of Science, 616:201–4 (1990), incorporated herein by reference).

A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example in Sambrook et al. (1989) op. cit., or Ausubel et al., ed. (1987) op. cit., both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

A useful, but not necessary element of an expression or other vector is one or more selectable or screenable markers. A selectable marker may be a gene that codes for a protein necessary for the survival or growth of a host cell transformed with the vector. The presence of this gene ensures the growth of only those host cells that contain the vector. Typical selection genes encode proteins that (a) confer resistance to antibiotics or other toxic substances, e.g., ampicillin, neomycin, methotrexate, etc.; (b) complement auxotrophic deficiencies, or (c) supply critical nutrients not available from complex media, e.g., the gene encoding D-alanine racemase for Bacilli. The choice of the proper selectable marker will depend on the host cell, and appropriate markers for different hosts are well known in the art.

A screenable marker is a gene that codes for a protein whose activity is easily detected, allowing cells expressing such a marker to be readily identified. Such markers include, for example, β-galactosidase, β-glucuronidase, and luciferase.

Expression vectors contain, in addition to those elements described above, sequences for controlling expression of a gene operably linked to these control sequences. Such an expression "cassette" may contain a promoter, an enhancer and necessary processing information sites, such as ribosome-binding sites, RNA splice sites, polyadenylation sites, transcriptional terminator sequences and mRNA stabilizing sequences. Control sequences will be chosen so that the sequences are functional in the desired host cell. For expression in mammalian or other eukaryotic cells, the enhancers or promoters may be those naturally associated with feline immunodeficiency virus (FIV) genes, although it will be understood that in many cases others will be equally or more appropriate. Other preferred expression control sequences for eukaryotes include enhancers and promoters derived from viruses, such as SV40, adenovirus, bovine papilloma virus, mouse mammary tumor virus, avian sarcoma viruses, adenovirus II, or polyoma virus, and the like. Promoters of genes that code for naturally occurring FIV polypeptides may also be used where appropriate. See, *Enhancers and Eukaryotic Gene Expression*, Cold Spring Harbor Press, N.Y. (1983), incorporated herein by reference.

For expression in prokaryotes, bacterial promoters such as the trp and lac promoters, tRNA gene promoters, promoters of genes encoding glycolytic enzyme, and bacteriophage promoters, are known and commonly used. See, Sambrook et al. (1989) op. cit., incorporated herein by reference.

Useful yeast promoters include the promoter regions for the genes coding for metallothionein, 3-phosphoglycerate kinase or other glycolytic enzymes such as enolase and glyceraldehyde-3-phosphate dehydrogenase, enzymes responsible for maltose and galactose utilization, and others. Suitable vectors and promoters for use in yeast expression are further described in R. Hitzeman et al., EP 73,657A, incorporated herein by reference.

For expression in other systems, such as insect cell culture, one may use conveniently available expression vectors which include a replication system and expression control sequences to which the nucleic acid that codes for the polypeptide to be expressed may be operably linked. For example, the baculovirus vector system is commonly used in insect cell culture expression. Examples of workable combinations of cell lines and expression vectors are described in Sambrook et al. (1989) op. cit.; see also, Metzger et al. *Nature* 334:31 (1989), incorporated herein by reference.

Expression vectors may also include secretion signals, which allow the protein to cross the cell membrane and either pass completely out of the cell permitting more convenient purification, or else lodge in cell membranes, and thus attain its functional topology.

A3. Host Cells

Mammalian cell lines are often used for the expression of polypeptides derived from eukaryotes. Propagation of mammalian cells in culture is per se well known. See, *Tissue Culture*, Academic Press, Kruse and Patterson, ed. (1973), incorporated herein by reference. Examples of useful mammalian host cell lines are Crandall feline kidney cells (CRFK), G355 feline brain-derived cells, FC74 cells, feline tongue cells (Fc3Tg), and continuous lines derived from cat peripheral blood lymphocytes such as those described in Yamamoto, et al. (1989) op. cit.). Other hosts may include such organisms as bacteria (e.g., *E. coli* or *B. subtilis*), yeast, filamentous fungi, plant cells, or insect cells, among others.

"Transformation" refers to the introduction of vectors containing the nucleic acids of interest directly into host cells by well known methods. Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods. See generally, Sambrook et al., (1989) op. cit. and Ausubel et al. (ed.), (1987) op. cit., both incorporated herein by reference. The cells into which have been introduced nucleic acids described above are meant to also include the progeny of such cells.

A4. Immunoglobulins

As used herein, "immunoglobulin" refers to molecules which have specific immunoreactive activity. Antibodies are typically tetramers of immunoglobulin molecules. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (e.g., Huston, et al., Proc. Nat. Acad. Sci. U.S.A., 85:5879–5883 (1988) and Bird, et al., *Science* 242:423–426 (1988), which are incorporated herein by reference). (See, generally, Hood, et al., "Immunology", Benjamin, N.Y., 2nd ed. (1984), and Hunkapiller and Hood, *Nature*, 323:15–16 (1986), which are incorporated herein by reference). Single-chain antibodies, in which genes for a heavy chain and a light chain are combined into a single coding sequence, may also be used.

"Monoclonal antibodies" may be obtained by various techniques familiar to those skilled in the art. Briefly, spleen cells from an animal immunized with a desired antigen are immortalized, commonly by fusion with a myeloma cell (see, Kohler and Milstein, Eur. J. Immunol. 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Monospecific immunoglobulins may also be produced by recombinant techniques in prokaryotic or eukaryotic host cells.

"Chimeric" antibodies are encoded by immunoglobulin genes that have been genetically engineered so that the light and heavy chain genes are composed of immunoglobulin gene segments belonging to different species. For example, the variable (V) segments of the genes from a mouse monoclonal antibody may be joined to feline constant (C) segments. Such a chimeric antibody is likely to be less antigenic to a cat than antibodies with mouse constant regions.

As used herein, the term chimeric antibody also refers to an antibody that includes an immunoglobulin having a feline-like framework and in which any constant region present is at least about 85–90%, preferably about 95% polypeptide sequence identity to a feline immunoglobulin constant region, analogous to so-called "humanized" immunoglobulins. Hence, all parts of such a "felinized" immunoglobulin, except possibly the CDR's, are substantially identical to corresponding parts of one or more native feline immunoglobulin sequences.

The term "framework region", as used herein, refers to those portions of immunoglobulin light and heavy chain variable regions that are relatively conserved (i.e., other than the CDR's) among different immunoglobulins in a single species, as defined by Kabat, et al., op. cit. As used herein, a "feline-like framework region" is a framework region that in each existing chain comprises at least about 70 or more amino acid residues, typically 75 to 85 or more residues, identical to those in a feline immunoglobulin.

"Anti-idiotypic" antibodies are produced by using a specific immunoglobulin as an immunogen. For example, infection or immunization with a virus induces a neutralizing immunoglobulin, which has on its Fab variable region combining site an image of a virion protein that is unique to that particular immunoglobulin, i.e., an idiotype. Immunization with such an antiviral immunoglobulin induces an anti-idiotype antibody, which has a conformation at its combining site that mimics the structure of the original viral antigen. These anti-idiotype antibodies may therefore be used instead of the viral antigen to elicit an immune response to the viral protein.

Immunoglobulin genes, in whole or in part, may also be combined with functional regions from other genes (e.g., enzymes), or with other molecules such as toxins or labels to produce fusion proteins (e.g., "immunotoxins") having novel properties. In these cases of gene fusion, the two components are present within the same polypeptide chain. Alternatively, the immunoglobulin or fragment thereof may be chemically bonded to the toxin or label by any of a variety of well-known chemical procedures. For example, when the label or cytotoxic agent is a protein and the second component is an intact immunoglobulin, the linkage may be by way of heterobifunctional cross-linkers, e.g., SPDP, carbodiimide, glutaraldehyde, or the like.

Suitable labels include, for example, radionuclides, enzymes, substrates, cofactors, inhibitors, fluorescers, chemiluminescers, magnetic particles. See, for examples of patents teaching the use of such labels, U.S. Pat. Nos. 3,817,837; 3,850,752; 3,939,350; 3,996,345; 4,277,437; 4,275,149; and 4,366,241, all of which are incorporated by reference.

Immunotoxins, including single chain molecules, may also be produced by recombinant means. Production of various immunotoxins is well-known with the art, and methods can be found, for example in "Monoclonal Antibody-Toxin Conjugates: Aiming the Magic Bullet," Thorpe et al, *Monoclonal Antibodies in Clinical Medicine*, Academic Press, pp. 168–190 (1982); E. Vitetta, *Science* (1987) 238:1098–1104; and G. Winter and C. Milstein, *Nature* (1991) 349:293–299; all incorporated herein by reference.

A variety of cytotoxic agents are suitable for use in immunotoxins. Cytotoxic agents can include radionuclides, such as Iodine-131, Yttrium-90, Rhenium-188, and Bismuth-212; a number of chemotherapeutic drugs, such as vindesine, methotrexate, adriamycin, and cisplatinum; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). (See, generally, commonly assigned U.S. Ser. No. 07/290,968 filed Dec. 28, 1988), "Chimeric Toxins," Olsnes and Pihl, *Pharmac. Ther.*, 15:355–381 (1981), and "Monoclonal Antibodies for Cancer Detection and Therapy," eds. Baldwin and Byers, pp. 159–179, 224–266, Academic Press (1985), all of which are incorporated herein by reference).

B. Description of the Invention

One aspect of the present invention involves the identification of conserved and variable regions in the envelope protein of feline immunodeficiency virus (FIV). A further aspect of the invention is the identification of a novel strain of FIV, the PPR clone.

B1. The PPR Clone of FIV

Different FIV isolates, although related, may display such significant differences as host cell range, and immunological characteristics, among others. Differences in host cell range can affect whole vital production in vitro, an important factor, for example, in economic production of whole virus vaccines. Immunological differences may influence the effectiveness of various vaccines developed from whole virus or subunits of the virus.

The PPR clone of a San Diego isolate of FIV disclosed herein differs significantly from Petaluma and other isolates, in its nucleic acid sequence. Variability in the sequence of the env gene has been used to determine the genetic similarity of human immunodeficiency virus isolates, with the most distantly related isolates having an env variability of greater than 12% at the nucleotide level. By these standards the PPR and 34TF10 (a Petaluma strain) clones, which have an env diversity of 14%, as shown below, are considered to be distantly related isolates. Furthermore, these two isolates vary in host cell range, as demonstrated below.

Figure 5:
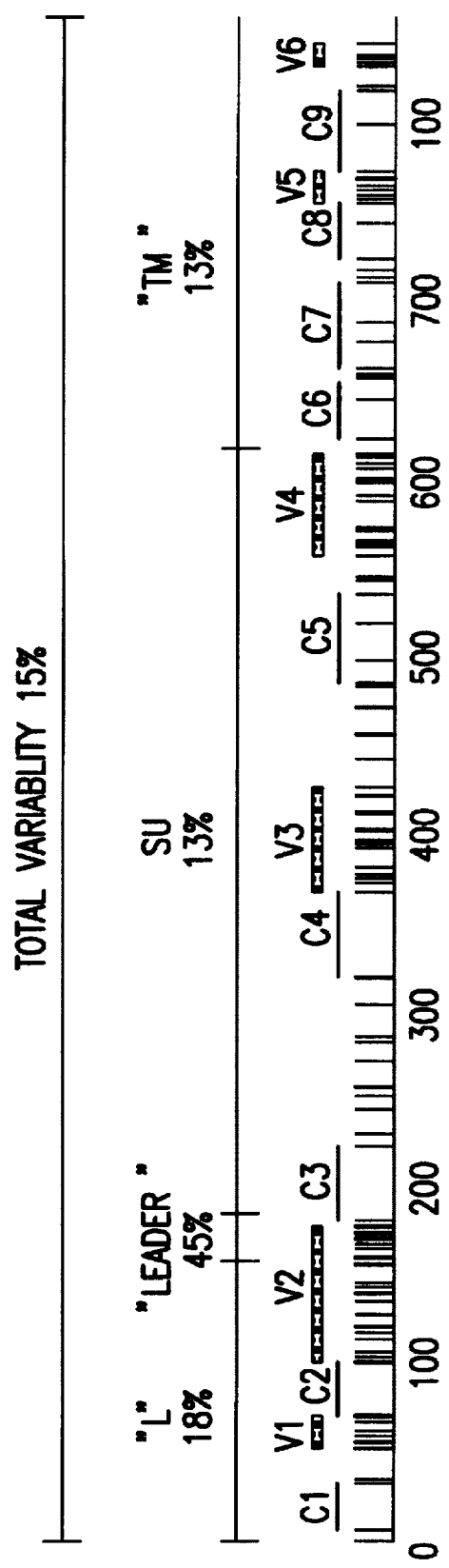
FIG. 5. Variability of the predicted env gene products. The percent amino acid differences for each region of the env gene (L region, leader, SU [surface protein], and TM [transmembrane protein] are listed under the appropriate identifying symbols. The vertical lines represent the locations of the predicted amino acid differences. The six variable and nine conserved regions are indicated by V and C, respectively.

Importantly for the development of diagnostic, therapeutic, and prophylactic methods for feline immunodeficiency virus, the characterization of the PPR clone, as described herein, has revealed that the envelope proteins of FIV viruses have variable regions (regions within which the amino acid sequences change relatively quickly) interspersed with constant regions (regions within which the amino aid sequences do not change significantly over time) (FIG. 5). The discovery of these constant and variable regions, as disclosed herein, facilitates the development of reagents that detect, treat, or prevent infection by a wide range of FIV and related viruses. For example, immunoglobulins raised against a constant region of a particular FIV envelope protein are likely to recognize viruses that, based upon the overall similarity of their envelope proteins, are not closely related. Conversely, immunoglobulins raised against a variable region of a particular FIV envelope protein are likely to be specific for that particular FIV isolate, providing a means to study strain distribution in a population, for example.

B2. Polypeptides of the PPR Isolate of FIV, and Conserved and Variable Regions of FIV Envelope Proteins One aspect of the present invention includes substantially purified polypeptides that have antigenic determinants specifically recognized by immunoglobulins raised against the PPR isolate of FIV. Substantially purified polypeptides that have amino acid sequences substantially identical to polypeptide fragments of conserved regions C1–C9 or variable regions V1–V6 of any FIV isolate (FIG. 5) are also included. These polypeptides include those that are either derived from a naturally occurring FIV polypeptide, or which share significant structural and functional characteristics peculiar to a naturally occurring FIV polypeptide of the present invention. Typically, the polypeptides will include at least five amino acids, usually at least nine amino acids, and more usually twelve or more amino acids found contiguously within one of the natural FIV proteins.

The polypeptides may include antigenic determinants, also referred to herein as haptens or epitopic sites, that are characteristic of the naturally occurring FIV polypeptides. By characteristic, it is meant that the antigenic determinant will allow immunologic detection of the virus or polypeptide in a physiological sample with reasonable assurance. Usually, although not in all cases, it will be desirable that the epitopic site be immunologically distinct from (i.e., not cross-reactive with immunoglobulins which recognize) viruses other than FIV. It is desirable to have an epitopic site that is common to viruses related to FIV, such as human immunodeficiency virus (HIV), when the present invention is used to treat, detect, or vaccinate against such related viruses.

The present invention includes polypeptides that are substantially identical in sequence to the claimed naturally occurring FIV polypeptides or fragments thereof, as well as allelic variants, naturally or synthetically produced mutants, including point, deletion, and insertion mutants. Also included are alternatively expressed variants, proteins encoded by nucleic acids that hybridize under high or low stringency conditions to nucleic acids that encode naturally occurring FIV polypeptides, proteins retrieved from naturally occurring materials, and closely related proteins retrieved by antisera directed against FIV polypeptide proteins.

Polypeptides having amino acid sequence changes from those claimed, due to, for example, genetic variation, both natural and induced, are also included. Induced mutants may be derived from nucleic acids encoding these proteins by using irradiation or exposure to chemical mutagens such as EMS, or may take the form of engineered changes by site-specific mutagenesis or other techniques of modern molecular biology. See, e.g., Sambrook, Fritsch and Maniatis (1989), *Molecular Cloning: A Laboratory Manual* (2nd ed.), CSH Press, incorporated herein by reference.

The polypeptides of the present invention may be recovered from cells infected with FIV virus or be produced by chemical synthesis or by recombinant DNA methods.

The natural polypeptides may be isolated from the whole virus by conventional techniques, such as affinity chromatography. Conveniently, polyclonal or monoclonal immunoglobulins obtained according to the present invention may be used to prepare a suitable affinity column by well known techniques (see, for example, Hudson and May, *Practical Immunology*, Blackwell Scientific Publications, Oxford, United Kingdom, 1980, incorporated herein by reference).

The polypeptides of the present invention may also be produced by chemical or enzymatic synthesis. Techniques for solid phase chemical synthesis of polypeptides are described, for example, in Merrifield, J. Amer. Chem. Soc. 85:2149–2156 (1963), incorporated herein by reference. Such chemical synthesis is generally employed for the production of polypeptides of fewer than about 100 amino acids, more usually fewer than about 80 amino acids, and typically fewer than about 50 amino acids.

A preferred method for producing such polypeptides involves the expression in host cells of recombinant DNA molecules encoding a desired portion, whether synthetic or natural, of the FIV genome, as described in more detail below.

Polypeptides of the invention may be purified using techniques discussed above, or other protein purification techniques known to those skilled in the art. The polypeptides of the present invention will typically be from about 50% W/W or more pure, preferably at least 80% pure, and more preferably, at least about 95% pure. Using conventional techniques of protein purification, homogenous polypeptide compositions of at least about 99% W/W can be obtained.

A "substantially glycosylated" polypeptide has attached to it about 50% of the carbohydrate groups attached to the same polypeptide when isolated from an FIV infected cat, preferably about 80%, and most preferably about 90% or more.

B3. Nucleic Acids

The nucleic acids of the present invention include substantially purified nucleic acids of the PPR isolate of FIV (GenBank Accession No. M36968, incorporated herein by reference), nucleic acids substantially identical to those that code for polypeptides having at least one antigenic determinant recognized by immunoglobulins specific for the PPR clone of FIV, and nucleic acids complementary to these sequences. Additional nucleic acids claimed are substantially purified nucleic acids that are substantially identical to, or substantially complementary to, nucleic acid sequences that code for all or part of one or more conserved regions C1–C9 of any FIV envelope protein, or for all or part of one or more variable regions (V1–V6) of an FIV envelope protein. The nucleic acid compositions of this invention, whether RNA, cDNA or genomic DNA, or may be a hybrid of the various combinations, and may be isolated from natural sources or may be synthesized in vitro. The nucleic acids claimed may be present in transformed or transfected whole cells, in a transformed or transfected cell lysate, or in a partially purified or substantially pure form.

Oligonucleotides are also included in the claimed invention. Such oligonucleotides are useful for use as probes for the presence of FIV nucleic acids in physiological samples, and as primers for gene amplification. The oligonucleotide sequences will usually be at least about 10 nucleotides in length, and more usually at least about 16 nucleotides.

Nucleic acid sequences that correspond to the entire viral genome or portions thereof, that are able to cause FIV infection when transformed or transfected into susceptible host cells, or that code for the claimed polypeptides or portions thereof, will normally be from hundreds to thousands of nucleotides in length. One or more introns may be present in protein-coding nucleic acid sequences. The length of nucleic acid sequences employed will depend on the use.

Through the use of recombinant DNA techniques one may express viral proteins in yeast, filamentous fungal, insect (especially employing baculoviral vectors), and mammalian cells, as well as bacterial systems. For this purpose, the natural or synthetic nucleic acids included in the invention will typically be operably linked to a promoter, and may be incorporated into an expression vector. Of course, viral proteins are expressed in prokaryotic cells in a nonglycosylated form, while eukaryotic systems are capable of glycosylating expressed foreign polypeptides. Mammalian or insect cell expression systems are preferred, since protein folding, transport and processing (including glycosylation) closely approximate that which occurs in the infected host. Viral proteins may be purified from lysed cells or, preferably, from culture medium into which viral proteins are secreted. Cell lines that have been transformed or transfected with the claimed nucleic acids, or that have been infected by the PPR isolate of FIV, are also included in the present invention.

The claimed nucleic acids may be modified in ways that increase their usefulness for producing viral particles or polypeptides. For example, the portion of a nucleic acid sequence that codes for a domain that serves to anchor a polypeptide to a cell membrane may be deleted, causing the polypeptide to be secreted into the medium. This may greatly facilitate purification of the polypeptide.

In addition to being useful for the production of virus particles or polypeptides, the nucleic acids of the present invention are useful for diagnostic purposes. For example, the nucleic acids or oligonucleotides may be used as probes to detect the presence of FIV or related viruses in physiological samples. Nucleic acid probes may also be useful for obtaining or constructing nucleic acids encoding FIV proteins, for obtaining sequences coding for naturally occurring FIV virus or fragments thereof, or viral transcripts or their corresponding cDNAs from cDNA or genomic libraries. The sequence of such probes need not have perfect complementarity with the FIV genome, as long as substantial complementarity is maintained. The nucleic acids of the invention may also be used for other purposes, as will be readily apparent to those skilled in the art.

Probes may include an isolated nucleic acid that includes or is attached to a label or reporter molecule. Probes may be prepared by nick translation, filling in of staggered double stranded DNA ends using the Klenow fragment of E. coli DNA polymerase, random hexamer priming, transcription of FIV sequences operably linked to phage or other promoters, or by using other methods known in the art. Guidance in making probes and choosing appropriate label or reporter molecules, are discussed, for example, in, Sambrook et al., (1989) op. cit., or Ausubel et al., (1987) op. cit., which are incorporated herein by reference.

Diagnostic assays for the presence of the FIV genome or transcripts of FIV genes may be conducted using DNA or RNA probes or oligonucleotide primers by conventional methods. Nucleic acid probes corresponding to the claimed nucleic acids may be useful, for example, in such diagnostic tests. Probes based upon the regions of the FIV envelope protein that are highly conserved among various isolates will be useful in detecting the presence of more than one isolate of FIV, or for detecting viruses related to FIV, such as human immunodeficiency virus (HIV). Probes based on the variable regions of the envelope protein will be useful in distinguishing among these isolates, i.e., for determining the identity of a particular FIV virus infecting an individual. Such information is useful, for example, in tracking the spread of disease in a population. Methods for the preparation and use of nucleic acid probes for diagnostic testing is described in U.S. Pat. No. 4,358,535, the disclosure of which is incorporated herein by reference.

The polymerase chain reaction (PCR) or other in vitro amplification methods may also be useful for detecting the presence of FIV in physiological samples. The sequence of PCR primers, as for probes, may be based on either conserved or variable regions of the FIV genome, for purposes discussed above, or may be based upon any other claimed nucleic acid. Exact complementarity to the nucleic acids being tested for is not required, but rather substantial complementarity is sufficient.

The polymerase chain reaction (PCR) or other in vitro amplification methods may also be useful, for example, to amplify gene sequences using primers derived from the DNA sequences disclosed herein, to clone nucleic acid sequences that code for proteins to be expressed, to make nucleic acids to use as probes for detecting the presence of FIV in physiological samples, for nucleic acid sequencing, or for other purposes. See, e.g., *PCR Protocols: A Guide to Methods and Applications*. (Innis, M. Gelfand, D., Sninsky, J. and White, T., eds.), Academic Press, San Diego (1990), incorporated herein by reference.

The claimed nucleic acids may also be used as antisense reagents for treating viral infection. Antisense nucleic acids are useful in arresting transcription or translation of viral genes or transcripts, or may be useful in arresting viral reproduction. For examples of the use of antisense nucleic acids as antiviral agents, see Sherman, M. I. (1990) op. cit., Rittner, K. and Sczakiel, G., *Nucl. Acids. Res.*, 19:1421-6 (1991), Rhodes, A., and James, W., *AIDS*, 5: 145–51 (1991), Vickers, T., et. al., *Nucl. Acids Res.*, 19: 3359–68 (1991), Sczakiel, G and Pawlita, M., *J. Virol.*, 65: 468–72 (1991), and Rhodes, A. and James, W., *J. Gen. Virol.*, 71:1965–74 (1990), all of which are incorporated herein by reference.

B4. Immunoglobulins

Polypeptides or virus particles of the present invention, described in subsections B1 and B2 above, may be used to produce polyclonal or monoclonal immunoglobulins by in vitro or in vivo techniques well known in the art. The resulting immunoglobulins that specifically recognize the claimed polypeptides or the virus particles of the PPR isolate of FIV are a further aspect of the present invention.

Some of these immunoglobulins are directed against specific FIV antigenic determinants, e.g., those characteristic of the PPR strain of FIV. An antigenic determinant is considered to be characteristic of the PPR strain of FIV if it is not present in other FIV strains; i.e., immunoglobulins specific for such an antigenic determinant will not bind to other FIV strains. The specificity resides especially in the complementarity determining regions (CDRs) of the immunoglobulins.

Immunoglobulins that recognize antigenic determinants characteristic of a polypeptide fragment from a conserved region (C1–C9) or variable region (V1–V6) of an FIV envelope protein (FIG. 5) are also part of the present invention. Immunoglobulins specific for conserved regions are likely to recognize viruses that are only distantly related to the PPR clone of FIV, perhaps even viruses as distantly related as human immunodeficiency virus (HIV). Immunoglobulins specific for variable regions, on the other hand, are likely to recognize only the isolate of virus from which the immunogen was derived, or very closely related viruses. Such immunoglobulins are useful for tracking the prevalence of a particular viral isolate in a population, for example.

Polypeptides useful for the purpose of stimulating production of specific immunoglobulins will, if serving directly as the immunogen, generally have more than about thirty amino acids, usually more than about fifty amino acids, although smaller peptide antigens may effectively stimulate production of specific neutralizing immunoglobulins. polypeptides smaller than about 10 kD, particularly those smaller than about 6 kD may be joined to a larger molecule in order to more effectively stimulate such an immune response. An adjuvant, such as incomplete Freund's adjuvant, may also be administered along with the immunogen. Less preferably, whole virus may also be employed as an immunogen.

In an in vitro approach for producing the immunoglobulins of the present invention, lymphocytes may be exposed to the claimed antigenic polypeptides, for example. In vivo techniques for immunoglobulin production require injection of these polypeptides into an appropriate host, generally mice or rats, rabbits, sheep, goats, or others. Immunogens are injected into the host according to a predetermined schedule, then bled periodically with successive bleeds generally having improved titer and specificity.

Immunoglobulins of the present invention may also be prepared by means of recombinant DNA methods once a nucleic acid encoding such an immunoglobulin has been cloned. The nucleic acid segments that code for these immunoglobulins are a further part of the present invention. These segments will typically be operably linked to an expression control sequence, such as promoter regions naturally associated with the immunoglobulin genes, or promoters from heterologous genes. Expression control sequences and vectors are described above.

The immunoglobulins may then be produced by introducing the expression vector containing the appropriate immunoglobulin gene into an appropriate host cell. The host cell line is then maintained under conditions suitable for high level expression of the immunoglobulin nucleotide sequences, and, as desired, the collection and purification of the light chains, heavy chains, light/heavy chain dimers or intact antibodies, binding fragments or other immunoglobulin forms may follow.

Suitable host cells include microorganisms, but mammalian or insect tissue cell culture may be preferable for producing the immunoglobulins of the present invention (see, E. Winnacker, "From Genes to Clones," VCH Publishers, N.Y., N.Y. (1987), which is incorporated herein by reference). A number of suitable host cell lines capable of secreting intact immunoglobulins have been developed in the art, and include the Chinese hamster ovary (CHO) cell line, but preferably transformed B-cells or hybridomas will be used.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, R. Scopes, *Protein Purification*, Springer-Verlag, New York (1982), incorporated herein by reference). Substantially pure immunoglobulins of at least about 90 to 95% homogeneity are preferred, and those of 98 to 99% or greater homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods*, Vols. I and II, Lefkovits and Pernis, eds., Academic Press, New York, N.Y. (1979 and 1981)).

These nucleic acid sequences that are capable of ultimately expressing the desired immunoglobulins can be formed from a variety of different polynucleotides (genomic or cDNA, RNA, synthetic oligonucleotides, etc.) and components (e.g., V, J, D, and C regions), as well as by a variety of different techniques. Joining appropriate genomic sequences is presently the most common method of production, but cDNA sequences may also be utilized (see, European Patent Publication No. 0239400 and L. Reichmann et al., Nature 332:323-327 (1988), both of which are incorporated herein by reference).

Chimeric antibodies or immunoglobulins that recognize antigenic determinants characteristic of the claimed polypeptides or of virus particles of the FIV isolate PPR are also within the scope of the present invention. A typical therapeutic chimeric antibody would be a hybrid protein consisting of the variable (V) or antigen-binding domain from a mouse immunoglobulin specific for these antigenic determinants, and the constant (C) or effector domain from a feline immunoglobulin, although domains from other mammalian species may be used for both variable and constant domains. As used herein, the term "chimeric antibody" also refers to antibodies coded for by immunoglobulin genes in which only the complementarity determining regions (CDR's) are transferred from the immunoglobulin that specifically recognizes the antigenic determinants, the remainder of the immunoglobulin gene being derived from a feline (or other mammalian, as desired) immunoglobulin gene. This type of chimeric antibody is referred to as a "felinized" antibody.

Feline constant region DNA sequences can be isolated in accordance with well known procedures from a variety of feline cells, but preferably from immortalized B-cells. The variable regions or CDRs for producing the chimeric immunoglobulins of the present invention will be similarly derived from monoclonal antibodies capable of binding to the desired antigen and produced in any convenient mammalian source, including, mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to the chimeric and "felinized" immunoglobulins specifically described herein, other substantially identical modified immunoglobulins can be readily designed and manufactured utilizing various recombinant DNA techniques well known to those skilled in the art. In general, modifications of the genes may be readily accomplished by a variety of well-known techniques, such as site-directed mutagenesis (see, Gillman and Smith, Gene 8:81–97 (1979) and S. Roberts et al., Nature 328:731–734 (1987), both of which are incorporated herein by reference).

Alternatively, polypeptide fragments comprising only a portion of the primary immunoglobulin structure may be produced. For example, it may be desirable to produce immunoglobulin fragments that possess one or more immunoglobulin activities in addition to, or other than, antigen recognition (e.g., complement fixation).

B5. Diagnostic Applications

The immunoglobulins of the present invention will find use in therapeutics as well as in diagnostics and other uses. Various techniques useful in these arts are discussed, for example, in Harlow and Lane, *Antibodies: A Laboratory Manual*, Cold Spring Harbor, New York (1988) (incorporated herein by reference for all purposes), including: immunization of animals to produce immunoglobulins; production of monoclonal antibodies; labeling immunoglobulins for use as probes; immunoaffinity purification; and immunoassays.

For diagnostic purposes, the immunoglobulins may either be labeled or unlabeled. A label is a substance that provides a detectable signal by any of a variety of techniques well known and reported in the art. The immunoglobulins of the invention themselves may be directly labeled. Alternatively, unlabeled immunoglobulins included in the invention may be used in combination with other antibodies (second antibodies) that are labelled and that recognize the immunoglobulins of the present invention. For example, labelled antibodies specific for feline immunoglobulin constant regions may be used to detect a "felinized" chimeric antibody.

A wide variety of labels may be employed, such as radionuclides, fluors, enzymes, enzyme substrates, enzyme co-factors, enzyme inhibitors, ligands (particularly haptens), etc. Numerous types of immunoassays are available and are well known to those skilled in the art.

The immunoglobulins and peptides of the present invention may be used in various immunoassays for detecting FIV and anti-FIV antibodies in physiological specimens, including such body fluid samples as blood, plasma, serum, urine, and cell samples, such as lymphocytes. Such immunoassay methods may include liquid phase immunoassays and Western blot analysis, competitive and noncompetitive protein binding assays, enzyme-linked immunosorbant assays (ELISA), an others commonly used and widely described in scientific and patent literature, and many employed commercially.

Such immunoglobulins and peptides may likewise be employed in immunohistochemical staining techniques by methods well known in the art.

Diagnostic uses of the nucleic acids of the present invention are discussed above.

B6. Therapeutic Applications

In addition to their use as diagnostics, compositions containing the polypeptides, nucleic acids, or immunoglobulins of the present invention, or a cocktail thereof can be administered for prophylactic and/or therapeutic treatments. In therapeutic application, compositions are administered to a subject already suffering from a disease, in an amount sufficient to cure or at least partially arrest the disease and its complications. An amount adequate to accomplish this is defined as a "(therapeutically) effective dose." Amounts effective for this use will depend upon the severity of the infection and the general state of the patient's own immune system, but generally range from about 1 to about 200 mg of antibody per dose, with dosages of from 5 to 25 mg per subject being more commonly used. It must be kept in mind that the materials of this invention may generally be employed in serious disease states, that is life-threatening or potentially life-threatening situations.

Methods by which the therapeutic effectiveness of immunoglobulins may be enhanced are well known to those skilled in the art. One such method is to utilize the immunoglobulins in combination with other immunoglobulins, or alternatively the immunoglobulins may be used as separately administered compositions well-known to those skilled in the art.

Another embodiment of the present invention embraces two-component immunoglobulins in which immunoglobulin polypeptides directed against FIV antigenic determinants are joined to other polypeptides or to non-peptide moieties. Immunotoxins are one such embodiment. Immunotoxins are particularly useful for killing selected cells, either in vitro or in vivo. An immunotoxin is made up of at least two components, the first of which is a cytotoxic agent that is usually fatal to a cell when the agent is absorbed into the cell is brought into close proximity to the cell. The second component of an immunotoxin, known as the "delivery" or "targeting" vehicle, provides a means for delivering the toxic agent to a particular cell type, for example, to carcinoma cells.

The immunoglobulins of the present invention are useful as delivery component of an immunotoxin. Intact immunoglobulins or their binding fragments, such as Fab, are preferably used. Typically, the immunoglobulins in the immunotoxins will be of the IgM or IgG isotype, but other constant regions may be utilized as desired.

The immunoglobulins and related pharmaceutical compositions of this invention are particularly useful for parenteral administration, i.e., subcutaneously, intramuscularly or intravenously. The compositions for parenteral administration will commonly comprise a solution of the immunoglobulin or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc.

The concentration of immunoglobulin in these formulations can vary widely, i.e., from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and 5 mg of immunoglobulin. A typical composition for intravenous infusion could be made up to contain 25 ml of sterile Ringer's solution, and 15 mg of immunoglobulin. Actual methods for preparing parenterally administrable compositions will be known or apparent to those skilled in the art and are described in more detail in, for example, Remington's Pharmaceutical Science, 15th ed., Mack Publishing Company, Easton, Pa. (1980), which is incorporated herein by reference.

The immunoglobulins of this invention can be lyophilized for storage and reconstituted in a suitable carrier prior to use. This technique has been shown to be effective with conventional immunoglobulins and art-known lyophilization and reconstitution techniques can be employed. It will be appreciated by those skilled in the art that lyophilization and reconstitution can lead to varying degrees of immunoglobulin activity loss (e.g., with conventional immunoglobulins, IgM antibodies tend to have greater activity loss than IgG antibodies) and that use levels may have to be adjusted to compensate.

Therapeutic uses of the nucleic acids of the present invention include the use of the nucleic acids as antisense reagents as discussed above. By introducing an appropriate antisense nucleic acid into an infected cell, viral reproduction can be slowed or stopped.

B7. Prophylactic Applications

The immunoglobulins, nucleic acids, and polypeptides of the present invention are also useful as prophylactics, or vaccines, for increasing resistance of a susceptible host to infection by FIV or related viruses. Compositions containing the immunoglobulins, polypeptides, or a cocktail thereof are administered to a subject not already in a disease state to enhance the subject's resistance to infection by FIV or a related virus. Administration to a cat or other mammals of an anti-FIV vaccine of the present invention gives rise to an anti-FIV immune response in the mammal entailing the production of anti-FIV immunoglobulins. The FIV-specific immunoglobulins then provide protection against infection by FIV or related viruses, such as HIV. An amount of prophylactic composition sufficient to result in increased resistance is defined to be a "(prophylactically) effective dose" or a "therapeutically effective dose."

Vaccines of the present invention include subunit vaccines, which are natural or synthetic peptides capable of acting as immunogens. These peptides may be isolated or synthesized and then may be conjugated to a synthetic or natural carrier molecule. The selection of antigenic sites that are likely to be important in triggering an immune response is facilitated, for example, by comparison of the amino acid sequence of vital antigens that have undergone antigenic change in nature, and also by identification of highly hydrophilic or mobile regions that should occupy an external and accessible location on the viral protein. These matters are facilitated by the sequence data provided herein.

Subunit vaccines provide a way to increase purity and decrease toxicity when compared to vaccines using whole virus particles, and may be prepared by known techniques. Such vaccines are prepared by selecting an antigen or antigens, purified from tissues or fluids of infected individuals or from cell culture, or prepared using recombinant DNA technology to express cloned antigens, and incorporating it in an appropriate carrier. Alternatively, such an antigenic protein or proteins or portions thereof may be incorporated into a larger fusion protein. The preparation of subunit vaccines, including those in which naturally derived or synthetic vital proteins or portions thereof are incorporated into vaccine compositions, are described, for example, in Lerner et al., Proc. Natl. Acad. Sci. USA 78:3403 (1981); Bhatanagar et al., Proc. Natl. Acad. Sci. USA 79:4400 (1982); and U.S. Pat. Nos. 4,565,697; 4,528,217; 4,575,495, 4,552,757; 4,552,758; and 4,593,002; relevant portions of which are incorporated herein by reference.

Immunoaffinity chromatography or lectin chromatography may be used to purify viral antigens from infected cells. Recombinant DNA techniques may also be employed to express viral proteins or their fragments or synthetic polypeptides representing immunologically important domains of viral surface antigens in prokaryotic or eukaryotic cells.

Although peptides representing the major antigenic sites of viruses may, in some cases, stimulate little if any neutralizing antibody, animals inoculated with these peptides may be primed to respond to subsequent inoculation of subimmunizing amounts of whole virus by developing a high level of neutralizing antibodies. This priming effect may be important in immunoprophylaxis.

In some instances, a major proportion of the immune response to an intact vital protein is directed to an immunodominant antigenic site that is highly variable among related strains of virus. Thus, a virus that differs only in these variable regions from a virus against which specific antibodies are present may escape recognition and neutralization by these antibodies. It may be possible to circumvent this form of strain-specific immune response by using synthetic peptides corresponding to normally immunosilent, highly conserved antigenic sites as immunogens. This is facilitated by the findings disclosed herein that FIV envelope proteins have both highly variable and highly conserved regions. Vaccines comprising single peptide vaccines and combinations of peptides and fragments thereof are comprehended by the vaccines of the present invention. These peptides and fragments may be chosen from one or more variable regions of an FIV envelope protein, or from one or more constant regions of an envelope protein. Alternatively, peptides or fragments having antigenic determinants characteristic of the PPR isolate of FIV may be chosen.

Two strategies are helpful in stimulating an immune response to linear peptides. In some cases, class II antigens of the host do not interact effectively with a given peptide due to polymorphism of class II histocompatibility antigens that control responses to synthetic peptide antigens at the T helper cell level. This may preclude the desired immune response. The need for T cell help can be met by addition of foreign or homologous helper T cell epitopes to B-cell epitopes of protective antigens. Another approach is to incorporate the peptide into a self-assembling particle, e.g., as an immunogenic protein resulting from the fusion of the peptide to a viral outer coat protein in a self-assembled viral particle by chemical or recombinant means. In these situations, presentation of peptides in a more favorable conformation and/or the presence of helper T cell epitopes on the carrier molecules may result in increased immunogenicity.

Numerous suitable carrier proteins and are known in the immunological arts, and any of these may be used as a part of the vaccines of the present invention. Among the carrier proteins are Keyhole limpet hemocyanin (KLH), ovalbumin, serum albumin from any mammalian species, globulins such as beta-lactoglobulin, oxygen-transporting proteins such as hemoglobins, or subunits thereof, myoglobins, hemocyanins and the like, and any of the various synthetic polypeptides which have been utilized as immunogenic carriers for small, haptenic molecules. As has been mentioned, the function of the carrier protein in a mammal immunized with it is stimulation of the mammal's immune system, presumably through activation of T-helper cells, to produce antibody, including antibody against the synthetic peptide conjugated to the carrier. In this regard, it is preferred to use, with a mammal of a given species, a carrier protein from a mammal of a different species, or from a non-mammal. The preferred carrier proteins for use in the synthetic proteins of the present invention are KLH or lipid carriers.

Any of the means of conjugating a synthetic peptide hapten or antigen to an immunogenic carrier protein commonly used in the art may be employed to make the vaccines of the present invention. These means include coupling via cysteines, using MBS; via primary amines using glutaraldehyde; or through hydrophobic interaction with lipid-based carriers.

Some viruses have evolved mechanisms that decrease the efficiency with which they can be neutralized by antibody. These mechanisms include the display of carbohydrate side chains in proximity to antigenic sites, as described for retroviruses. For this reason, glycosylated and nonglycosylated proteins may both play an important role in vaccine development efforts.

It is generally believed that an immune response to the carbohydrate moiety of FIV glycoproteins will be an important component of an FIV vaccine. The extent to which FIV-encoded proteins are glycosylated depends to some degree on the type of infected cells in which the viral proteins are produced. Preferred cell lines for viral protein production are peripheral blood leukocytes (PBLs) and the PPR-FET cell line, which, when infected with FIV, produce virus having substantially glycosylated proteins.

A further aspect of the prophylactic use of the present invention is the use, as an immunogen, of immunoglobulins recognizing FIV antigenic determinants. The resulting antibodies against the administered immunoglobulins are known as anti-idiotypic antibodies. As explained above, these antibodies are likely to recognize the same FIV antigenic determinants as the administered immunoglobulins. An amount of immunoglobulin composition sufficient to result in increased resistance is defined to be a "(prophylactically) effective dose." In this prophylactic use of the immunoglobulins, the precise amounts again depend upon the subject's state of health and general level of immunity, but generally range from 0.1 to 25 mg per dose, especially 0.5 to 2.5 mg per subject. Single or multiple administrations of the anti-idiotype antibody compositions can be carried out with dose levels and pattern being selected by the treating veterinarian. In any event, the pharmaceutical formulations should provide a quantity of the immunoglobulin(s) of this invention sufficient to effectively treat the subject.

The present invention further embodies vaccines against FIV or related viruses that are made up of complete or partial virus particles of the PPR clone of FIV, including inactivated or subunit vaccines, live (attenuated) virus vaccines, and the like. Various types of vaccines, their advantages and disadvantages, and principles governing their production, use, and the protection they afford are discussed, generally, in *Virology*, B. Fields et al., ed., Raven Press, New York, 1990, and *Vaccine Biotechnology*, J. Bittle and F. Murphy, eds. (*Advances in Veterinary Science and Comparative Medicine*, Vol. 33), Academic Press, San Diego, 1989, both incorporated herein by reference. Such vaccines are useful, for example, in eliciting or priming a humoral response in cats and immunizing cats against FIV infection.

An immune response to nonsurface antigens of the virus may play a cooperative role in the development of effective resistance by augmenting the antibody response to one or more major protective antigen. For this reason, inclusion of such helper nonsurface antigens in viral particle-derived vaccines may contribute in some cases to maximal immunogenicity.

Inactivated virus vaccines are generally prepared from virus particles that have been inactivated with formalin, for example. Other techniques commonly used to wholly or partially inactivate virus include passaging the virus at elevated temperatures, contacting the viral particles with such agents as ultraviolet (UV) light, ethylmethanesulfonate, phenol, α-lactopropionate, psoralens, platinum complexes, and ozone. Such inactivated vaccines may be highly effective in preventing disease.

New techniques for constructing viruses that contain defined mutations or gene constellations are increasingly applied to development of live virus vaccines. Viruses bearing stable, defined, identifiable attenuating mutations or gene constellations represent the vaccine strains of the future, because the genetic basis for attenuation is known and can be monitored directly during all phases of vaccine development, manufacture, and utilization in the subject.

Such defined mutations can include missense mutations, produced by base substitution in the viral genome and reflected in an amino acid substitution in the corresponding region of the encoded viral protein. Missense mutations include conditional lethal, temperature-sensitive mutants, cold-adapted mutants that replicate efficiently only at subnormal temperature, protease-activation mutants, which result from mutations at or near the cleavage site of a fusion glycoprotein that alters the cleavability of the protein by host-cell proteases, and monoclonal antibody escape mutants that have sustained a single amino acid substitution in a virus surface protein resulting in altered tissue tropism and altered pathogenesis of infection. The nucleotide sequence analysis disclosed herein allows one to identify and target favorable sites for directed mutagenesis efforts.

The vaccines of the present invention include FIV viruses of the PPR strain having point, deletion, or insertion mutations of nonstructural regions or structural genes, including nucleotide substitutions, partial deletions or insertions within a gene, deletion of an entire gene, synergistic interaction between two deleted genes, or deletions within noncoding regions.

A further type of vaccine embodied in the present invention are those of the Jennerian approach. This approach has involved, for example, the use of a virus strain of mammalian or avian origin to immunize humans against a human virus that is related antigenically to the animal strain. The mammalian and avian viruses are well adapted to their natural host, but often do not replicate efficiently in humans and hence are attenuated in humans. Thus, the vaccines of the present invention may be useful as human vaccines, e.g., to confer protection against HIV, as well as in the development of feline vaccines.

The present invention further embodies multivalent vaccines, which offer protection against multiple disease agents. These may be compositions that include components of the present invention, such as a killed or attenuated FIV virus of the PPR strain, or a claimed FIV peptide or other claimed immunogen. The multivalent vaccine compositions further include immunogens whose administration raises a protective immune response to viral or bacterial pathogens other than FIV. Such multivalent vaccines may include not only mixtures of such immunogens but also recombinant immunogens, such as recombinant polypeptides.

Recombinant virus genomes that include the PPR isolate of FIV are also embodied in the present invention. Viable intertype chimeras (hybrids) may be constructed using the PPR genome along with all or part of the genome of a different virus, the resulting chimeric virus displaying dual antigenic specificity and stimulating antibodies capable of neutralizing both viral types.

The use of the genome of the PPR isolate of FIV to construct viable recombinants that express the protective antigens of other viruses is also included in the invention. Stable attenuated vaccine viruses, as described above, are useful for this purpose.

Other uses included are the delivery of gene products to various cellular or tissue targets (e.g., nervous tissue) by the use of viral promoters or whole viral genomes to act as delivery systems. Adaptation of attenuated FIV virus of the PPR strain for such purposes may include the manipulation of the FIV genome by such steps as: deleting non-essential regions of the viral genome; removing restriction sites by well-known mutagenesis strategies, such as site-directed mutagenesis using oligonucleotides; inserting polylinker sequences for cloning foreign DNA sequences; inserting sequences encoding a suitable screenable or selectable marker; inserting promoter sequences adjacent to cloning sites, so that the promoter is operably linked to fragments cloned into the sites; and other steps well known in the art for creating such vectors.

The vaccines of the present invention may be employed prophylactically by immunization of a cat prior to its exposure to the FIV virus. Such vaccines may also be used to treat cats after they have been exposed to the virus. The vaccines of the present invention may be administered by any of several methods well known and practiced in the art, including oranasally (except, generally with partially inactivated virus vaccine), subcutaneously, or intramuscularly.

The vaccine preparation will typically include other components known to those skilled in the art. Among these components will be a diluent and an adjuvant that are pharmaceutically acceptable. The adjuvant, where used, promotes stimulation of the immune system to mount an effective immune response against the peptide conjugated to the carrier protein. An example of a physiologically acceptable diluent is physiological saline, such as phosphate-buffered saline (PBS). Examples of acceptable adjuvants include complete Freund's adjuvant, incomplete Freund's adjuvant, aluminum oxide, and alum.

The present invention also contemplates methods of administering to a cat an immunogenic amount of a vaccine of the invention. Immunization can be by administration of a single dose of vaccine. However, more typically, it will involve administration of a number of doses, typically at least two. Each dose will have an immunogenic amount of vaccine.

In prophylactic, pre-exposure immunization of cats, typically 3 doses, on days 0, 14, and 28, will be administered, by intramuscular, intraperitoneal, or intravenous injection. A booster dose may be administered. Post-exposure immunization may be required, and post-exposure administration of anti-FIV immunoglobulin may be employed for subjects immunized prior to exposure.

In treating a cat that has been exposed to FIV, the method of immunization will involve the same immunization schedule as in the previous paragraph. The purpose of the dosage regime is to induce a massive, active immune assault against FIV that has been introduced into the cat's system. Those of skill in the art will understand how to determine a dosage regimen that is appropriate of cats of a particular age, weight and medical condition. The progress of the treatment may be followed by any of numerous FIV assay methods described herein, as will be appreciated by the skilled practitioner.

B8. Kits

Another aspect of the present invention is kits for use in diagnosing the presence of FIV in a physiological sample. It will be readily appreciated that the presence of FIV could be ascertained using kits providing means for detecting either the FIV genome, FIV-specific immunoglobulins, or FIV antigenic determinants.

A first type of kit is supplied for use with the subject nucleic acids, whether double stranded or single stranded. The nucleic acids are employed as probes for detection, by hybridization, of the FIV genome or transcripts present in a physiological sample (e.g., blood or saliva). Such kits will comprise the nucleic acid probes, which may be conjugated to a label or unconjugated, buffers, such as Tris, phosphate, carbonate, etc., and instructions for use. Such kits may also comprise positive control samples containing FIV nucleic acids and/or negative control samples lacking such nucleic acids.

Kits are also supplied in which the subject nucleic acids, preferably single stranded synthetic oligonucleotides, are used as primers for enzymatic amplification of the FIV genome or transcripts present in a physiological sample (e.g., blood or saliva), for example, by PCR. Such kits may further include a polymerase, such as DNA polymerase I or the Klenow fragment of DNA polymerase I, T4 or T7 polymerase, thermostable DNA polymerases (e.g., Taq polymerase). Such kits may include the oligonucleotides, which may be conjugated to a label or unconjugated, buffers capable of providing suitable conditions for enzymatic amplification, and instructions for use. Such kits may also include positive control samples containing FIV nucleic acids and/or negative control samples lacking such nucleic acids. Additional types of kits are supplied for use with the subject immunoglobulins in the protection against or detection of FIV in a physiological sample (e.g., blood or saliva). Thus, one or more of the immunoglobulins of the present invention may be provided, usually in a lyophilized form in a container, either alone or in conjunction with additional immunoglobulins specific for the desired cell type, and instructions for use. Such kits may also comprise positive control samples containing FIV antigens and/or negative control samples lacking such antigens. The immunoglobulins, which may be conjugated to a label or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active immunoglobulin, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the anti-FIV immunoglobulin is employed in an assay, this will usually be present in a separate vial. The second antibody is typically conjugated to a label and formulated in an analogous manner with the antibody formulations described above.

Alternatively, kits may be supplied in which the polypeptides of the present invention are affixed to a solid support and are contacted by immunoglobulins present in a physiological sample (e.g., blood). Such kits may also contain appropriate buffers, instructions for use, positive control samples containing FIV antigens and/or negative control samples lacking such antigens, and may also include such components as a labelled immunoglobulin for binding to the peptide-immunoglobulin complex. If the labelled immunoglobulin is labelled with an enzyme, components such as a substrate that reacts with the enzyme-labelled immunoglobulin to form a colored product and a second buffer solution for stopping the development of the colored product may also be included.

The following examples are offered by way of illustration, not by way of limitation.

C. Examples

The nucleotide sequences of two closely related variants of the Petaluma isolate of FIV have been reported (R. Olmsted et al., 1989 Proc. Natl. Acad. Sci. USA 86:8088–8092; R. Talbott et al., 1989 Proc. Natl. Acad. Sci. USA 86:5743–5747; both incorporated herein by reference). Herein is reported an analysis of the complete nucleotide sequence of a new molecular clone of FIV (termed PPR), which originated from a cat from the San Diego, Calif. area. The PPR clone of the San Diego isolate differs substantially from two clones of the Petaluma isolate, not only in its nucleic acid sequence but also in its in vitro host cell range.

MATERIALS AND METHODS

Cells and virus. The Petaluma isolate of FIV was originally obtained from a Petaluma, Calif. cat (N. Pedersen et al., 1987 Science 235:790–793, incorporated herein by reference). Prior to death, this cat demonstrated signs of severe immunodeficiency. This isolate was adapted to and propagated in an adherent cell line, Crandall feline kidney (CRFK) cells. The adherent feline cell line G355-5 used in the transfection studies was established from a cat fetal brain culture (D. Haapala et al., 1985 J. Virol. 53:827–833, incorporated herein by reference).

The PPR clone of the San Diego isolate was obtained from a cat suffering from a chronic debilitating illness. This cat originated from Cold Spring Harbor, N.Y. However, six years prior to viral isolation, the cat moved to the San Diego, Calif. area. Signs of FIV infection did not appear until approximately three years after relocation. Exactly when or where this cat contracted FIV was not known. The cat had a long and protracted illness characterized by lethargy, gingival ulceration, and tooth loss. The cat was FIV positive and feline leukemia virus negative. Symptomatic treatment was initiated and continued until the cat's condition deteriorated so much as to require humane euthanasia.

On necropsy examination of the cat, it was noted that the gastrointestinal tract was virtually devoid of ingesta, suggesting that the cat had not eaten in the last 24 hours. Detailed histological and hematological evaluations were not performed. The San Diego isolate was obtained by culturing the cat's peripheral blood leukocytes (PBLs) in RPMI-1040 in the presence of 10% fetal bovine serum and recombinant human interleukin-2 (kindly provided by Hoffman-La Roche). PBLs from FIV-negative, specific-pathogen-free cats were added to the culture to maintain a 40% viability. The culture was monitored weekly for the development of $Mg^{2+}$-dependent reverse transcriptase activity (N. Pedersen et al., 1987, incorporated herein by reference).

Transfections. Full-length plasmid clones of 34TF10 and PPR were separately transfected into the G355-5 cells by the calcium phosphate precipitation method (B. Parker and G. Stark, 1979 J. Virol. 31:360–369, incorporated herein by reference). The next day, noninfected feline PBLs were cocultivated with the transfected G355-5 cells for 24 hours. After the cocultivation, the G355-5 cells and the cocultivated PBLs were maintained separately and monitored for the appearance of $Mg^{2+}$-dependent reverse transcriptase activity (N. Pedersen et al., 1987, incorporated herein by reference).

PCR amplification of cDNA. The polymerase chain reaction (PCR) was used to characterize the splice donor and splice acceptor sites of clone 34TF10. RNA was prepared from CRFK cells that were chronically infected with Petaluma strain of FIV (Sambrook et al., (1989), incorporated herein by reference). The cDNA was made by conventional methods (G. Sarkar and S. Sommer, Nucleic Acids Res. 16: 5197 (1988), incorporated herein by reference). Amplification of the cDNA was accomplished by selecting 5' and 3' PCR primers that had been altered to produce EcoRI sites to facilitate cloning into M13. The upstream primer correspond to the 5' end of the viral mRNA (bases 229 to 252 [R. Talbott et al., Proc. Natl. Acad. Sci. USA 86:5743–5747 (1989), incorporated herein by reference]). The downstream primer was from the 5' region of the env gene (bases 6463 to 6489 [Talbot et al. (1989), incorporated herein by reference). The PCR products were cloned into M13 and sequenced.

Genomic libraries. DNA was prepared from FIV-infected CRFK cells (Petaluma strain) or PBLs (San Diego strain) as described previously (N. Blin and D. Stafford, 1976 Nucleic Acids. Res. 3:2303–2308; M. Vogt et al., 1985 J. Virol 55:184–192; both incorporated herein by reference). The DNA was then partially digested with the restriction enzyme Sau3A to yield fragments with an average size of 20 kilobases (kb). Fragments were ligated into the BamHI site of the bacteriophage lambda vector EMBL-4 (Stratagene), and six genomic equivalents of DNA were packaged. The library was then plated for subsequent screening with virus-specific $^{32}$P-labeled probes derived from the pol gene of the 34TF10 clone of FIV (Talbot et al., 1989, incorporated herein by reference). Positive clones were selected and taken through several cycles of purification prior to further analysis.

Nucleotide sequencing. Nucleotide sequencing was performed as described before (F. Sanger et al., 1977 Proc. Natl. Acad. Sci. USA 74:5463–5467, incorporated herein by reference). Specific proviral oligonucleotide primers were prepared to sequence the entire viral genome in both directions.

Computer analysis. The nucleotide and protein alignments as well as the percent identity and percent similarity were done with the University of Wisconsin Genetics Computer Group Sequence Analysis Software Package version 6.1.

Nucleotide sequence accession number. The complete PPR sequence has been deposited in the GenBank data base (accession no. M36968, incorporated herein by reference).

RESULTS

Figure 1B:
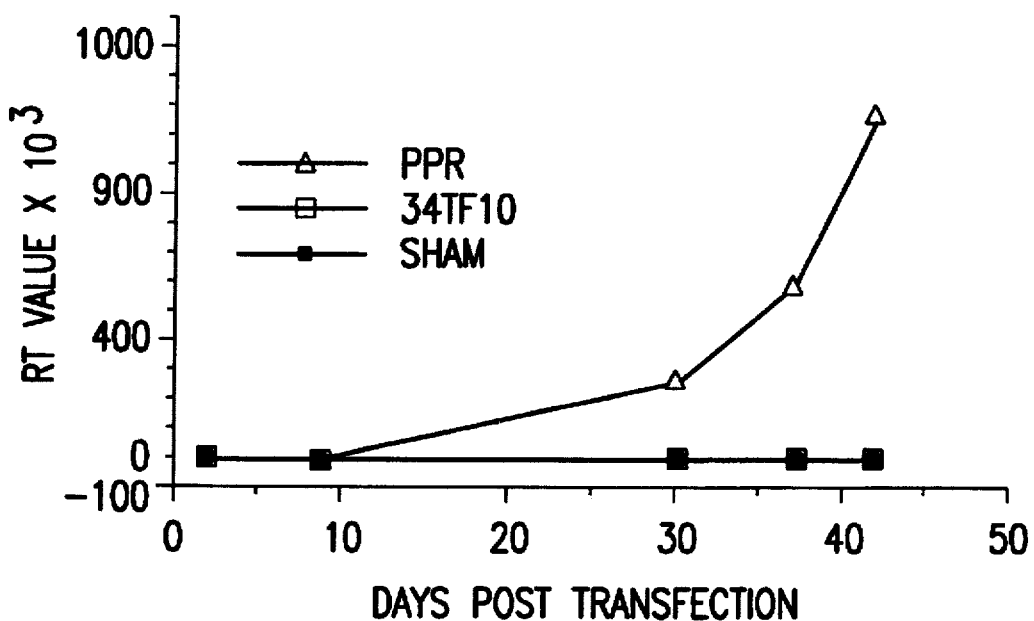
FIG. 1D is a ×200 magnification of the 34TF10-transfected cells. The arrows indicate the location of small syncytia observed in conjunction with productive infection by the 34TF10 clone. Note, in addition, that the productively infected cells (FIGS. 1B and D) took on a more elongated, spindle-shaped appearance with loss of refractivity, as well as a more organized growth pattern, relative to nonproductively infected cells (panels A and C). Bars, 20 μm.
Figure 2A:
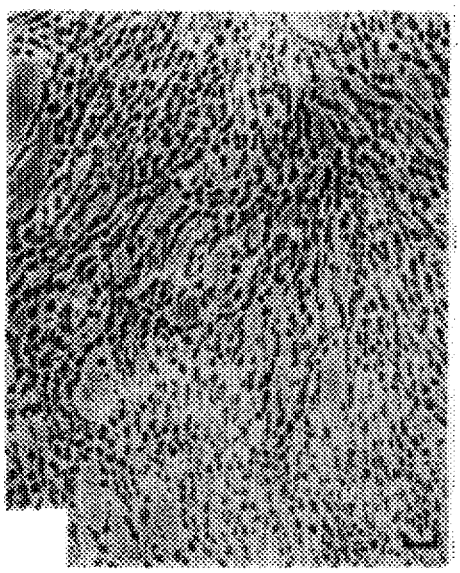
FIGS. 2A–D. Morphological changes of G355-5 cells associated with a productive FIV infection. PPR, 34TF10, and sham-transfected G355-5 cells are shown in FIG. 1A A, B, and C, respectively, at low magnification (×100).
Figure 2B:
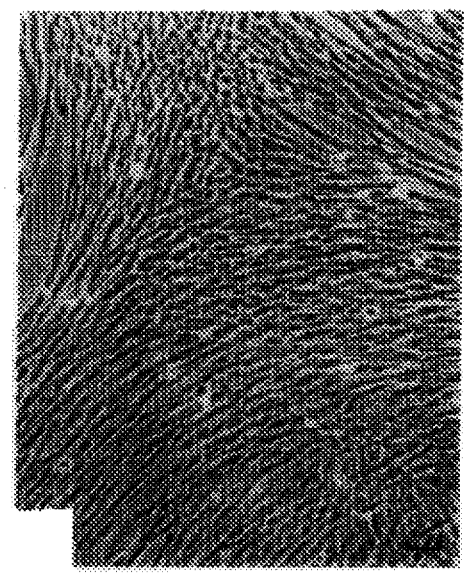
Figure 2C:
Figure 2D:
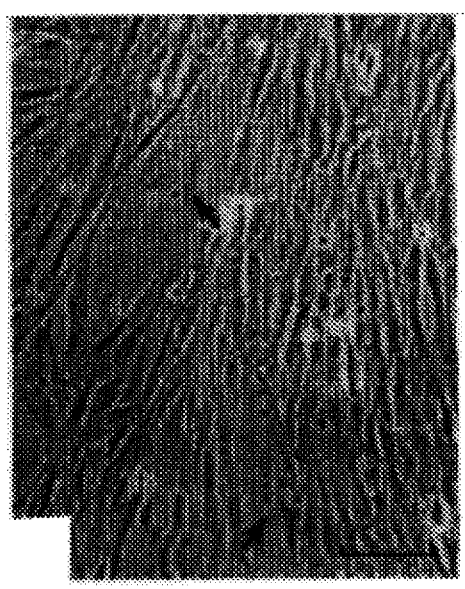

Transfection studies. Both of the FIV clones were infectious, as demonstrated by the rise in reverse transcriptase activity following transfection (FIG. 1). However, the clones differed in their in vitro host cell range. Substantial reverse transcriptase activity was only found in G355-5 cells after transfection with the 34TF10 clone. In contrast, reverse transcriptase activity was found only in PBLs transiently cocultivated with the PPR-transfected G355-5 cells. Long-term cultures of the G355-5 cells either transfected or infected with the PPR isolate remained negative for reverse transcriptase activity. However, infections of PBLs by the 34TF10 clone could be established when higher multiplicities of infection were used. The G355-5 cells transfected with the 34TF10 clone developed a directional growth pattern and became more elongated and spindle shaped relative to PPR-transfected and sham-transfected control cells FIGS. 2A–D. Small syncytia were also apparent in the 34TF10-infected cultures (FIG. 2D). These cultures eventually died if not replenished with noninfected cells.

Nucleotide sequence analyses. The complete nucleotide sequence of the 34TF10 clone of the Petaluma isolate of FIV has been reported previously (R. Talbott et al., 1989, incorporated herein by reference). The complete PPR sequence has been deposited in the GenBank data base (Accession No. M36968, incorporated herein by reference), and regions of interest are presented here.

Figure 3A:
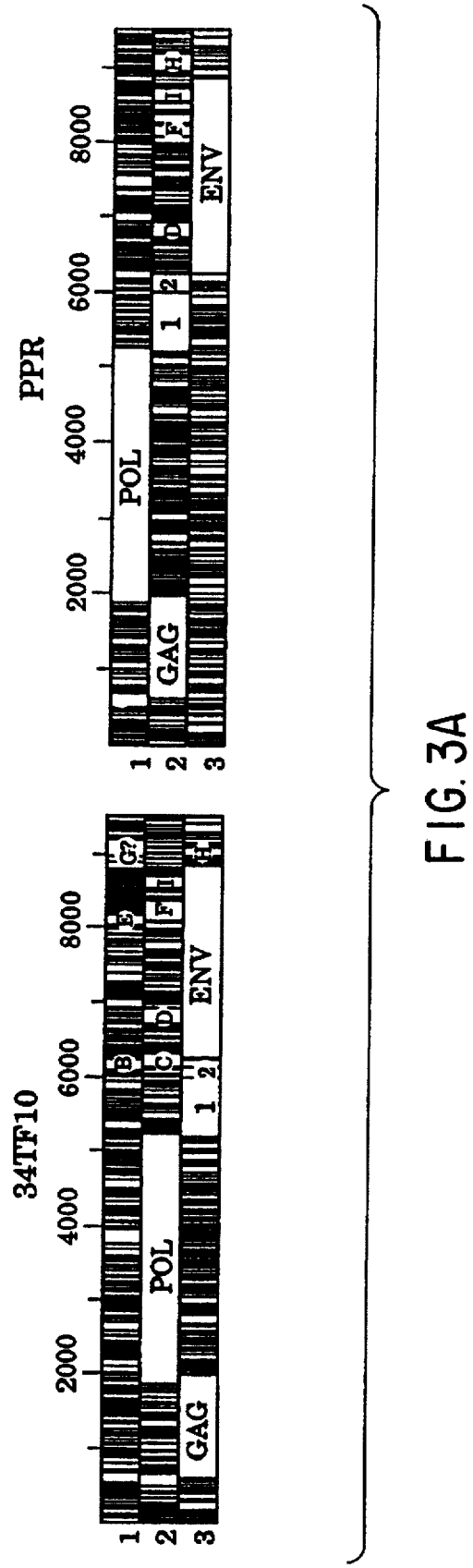
FIG. 3(A). Comparison of the ORFs of the PPR and 34TF10 clones.
Figure 3B:
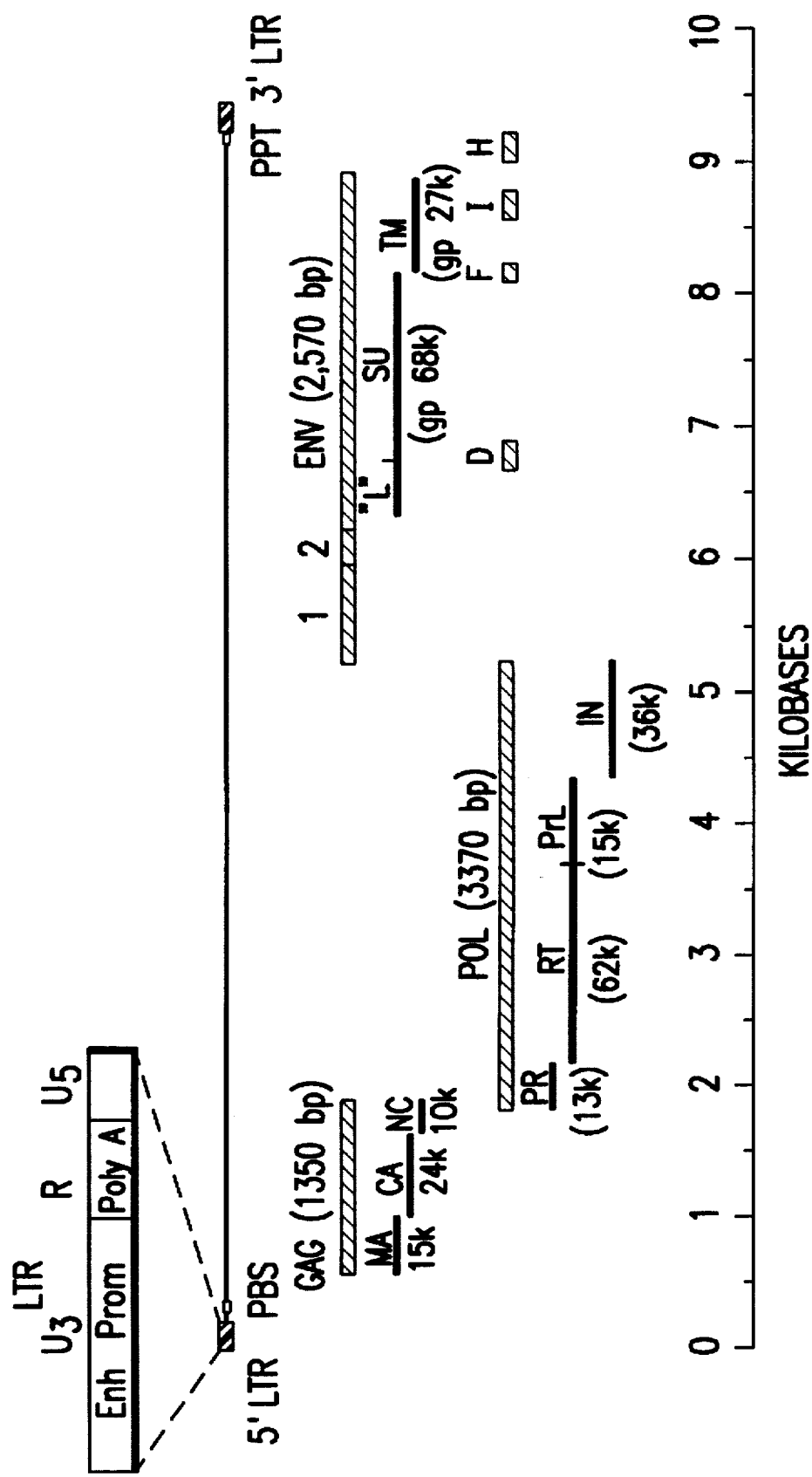
FIG. 3(B). Consensus genomic organization of FIV. Features of both LTRs are shown in the 5' LTR. gag region encodes the matrix (MA), capsid (CA), and nucleocapsid (NC) proteins. pol region encodes protease (PR), reverse transcriptase (RT), proteaselike protein (PrL), and integrase (IN). env region encodes the putative L protein (9, 45) as well as major (SU) and minor (TM) glycoproteins of the viral envelope. PPT, Polypurine tract; PBS, primer-binding site. In addition to the above gene segments, six short ORFs, 1, 2, D, F, I, and H, were evident and conserved in both FIV clones. k, Kilodaltons.

The PPR clone had a genome length of 9,468 base pairs (bp). Comparisons of the sequences of the 34TF10 and PPR clones revealed an overall nucleic acid sequence identity of 91%. The basic genomic organization of PPR and 34TF10 was similar. The only differences occurred in the small open reading frames (ORFs). Some of these small ORFs, previously noted in the 34TF10 strain, were not conserved in PPR. A comparison of the ORFs between 34TF10 and PPR clones and a summary diagram of the consensus genomic organization are shown in FIGS. 3A and 3B.

Figure 4:
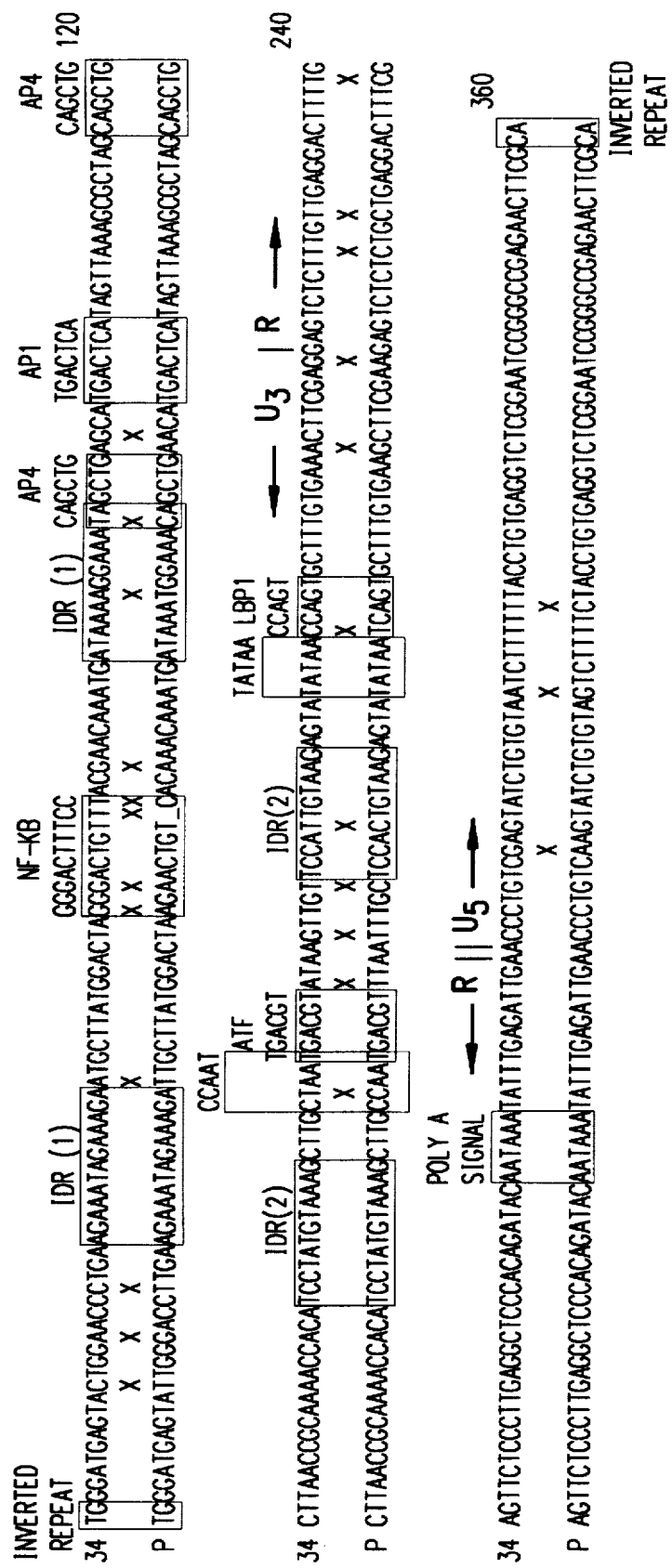
FIG. 4. Nucleotide sequence comparison of the LTR from the PPR and 34TF10 clones of FIV. Important structural features are boxed: the inverted repeats at the 5' and 3' ends of the LTR, two sets of imperfect direct repeats (IDR 1 and 2), CCAAT site, TATAA site, LBP-1 site, polyadenylation (Poly A) signal, and the recognition sequences of the enhancer proteins NF-KB, AP-1, AP-4, and ATF. The consensus sequences, for the enhancer-binding sites, are indicated above the appropriate box. Arrows indicate the boundaries of the U3, R, and U5 regions of the LTR. X's indicate nucleotide changes between the two clones. The underlined space indicates a relative deletion/insertion.

LTRs. The long terminal repeats (LTRs) of the PPR and 34TF10 clones had 93% nucleic acid identity (FIG. 4). The TATA box of the promoter and the two base inverted repeats at the 5' and 3' ends of the LTR were perfectly conserved. The location of the polyadenylation site and, thus, the boundary between the R and the U5 regions of the LTR was confined to either base 287 or base 288 of the 34TF10 clone (FIG. 4). Since both of these bases were adenine residues, the exact location of the polyadenylation site was not determined. The 20-base region of the LTR from the start of the polyadenylation signal to the polyadenylation site was perfectly conserved between the two clones. In the U3 region of the LTR, several known upstream enhancer-promoter elements were common to both clones: AP-4 (28), AP-1 (28), and ATF (24) binding sites, as well as the TATA element (FIG. 4). However, the consensus sequence for a second AP-4 site and a CCAAT promoter element were present in the PPR clone but not conserved in the 34TF10 clone (FIG. 4). A putative LBP-1 (22) binding site and partial nucleotide match (8 of 10) for the consensus sequence of the NF-KB binding site (J. Hiscott et al., 1989 J. Virol. 63:2557–2566, incorporated herein by reference) were found in the 34TF10 clone but not in the PPR clone (FIG. 4). Enhancers frequently take on the form of imperfect direct repeats. Two sets of imperfect direct repeats are shown in FIG. 4. Both sets of these imperfect direct repeats were conserved in the PPR and 34TF10 clones.

gag gene. The gag gene of FIV is predicted to encode a polyprotein of 450 amino acids, and the gene spans from nucleotide 628 to 1977. Posttranslational cleavage of this polyprotein should yield the predicted matrix (MA), capsid (CA), and nucleocapsid (NC) proteins (45). This gene and its predicted protein products were highly conserved between the 34TF10 and PPR clones (Table 1).

pol gene. The poi gene of FIV is most likely transcribed as a gag-pol polyprotein by ribosomal frameshifting (R.

Talbott, 1989, incorporated herein by reference). The frameshift likely occurs at nucleotide 1869 of the viral genome, and the gene extends through nucleotide 5240. It has been suggested that through autodigestion, the following proteins result: protease (PR), reverse transcriptase (RT), protease-like protein (PrL) (M. McClure, et al., 1987a Proc. Natl. Acad. Sci. USA 84:2693–2697; M. McClure et al., 1987b Proc. Natl. Acad. Sci. USA 85:2469–2473; R. Olmsted et al., 1989 Proc. Natl. Acad. Sci. USA 86:8088–8092; Talbott et al., 1989; all incorporated herein by reference), and integrase (IN). The predicted protein products of the pol gene were highly conserved (Table 1).

env gene. In addition to coding for the surface (SU) and the transmembrane (TM) proteins, the env gene of FIV (nucleotide 6265 to 8833) has the potential to encode a third protein, of unknown function (R. Talbott et al., 1989, incorporated herein by reference), similar to the L protein of visna virus (J. Davis and J. Clements, 1989 Proc. Natl. Acad. Sci. USA 86:414–418, incorporated herein by reference). Of the large ORFs, the one with greatest nucleotide sequence variability was the env gene (Table 1). The predicted amino acid differences of the env gene products were not distributed randomly (FIG. 5). They clustered in six areas, which were called variable regions, 1 through 6 (V1 to V6). Nine areas of the predicted env gene product were well conserved, with few or no amino acid changes. These regions were designated conserved areas 1 through 9 (C1 to C9).

Figure 6A:
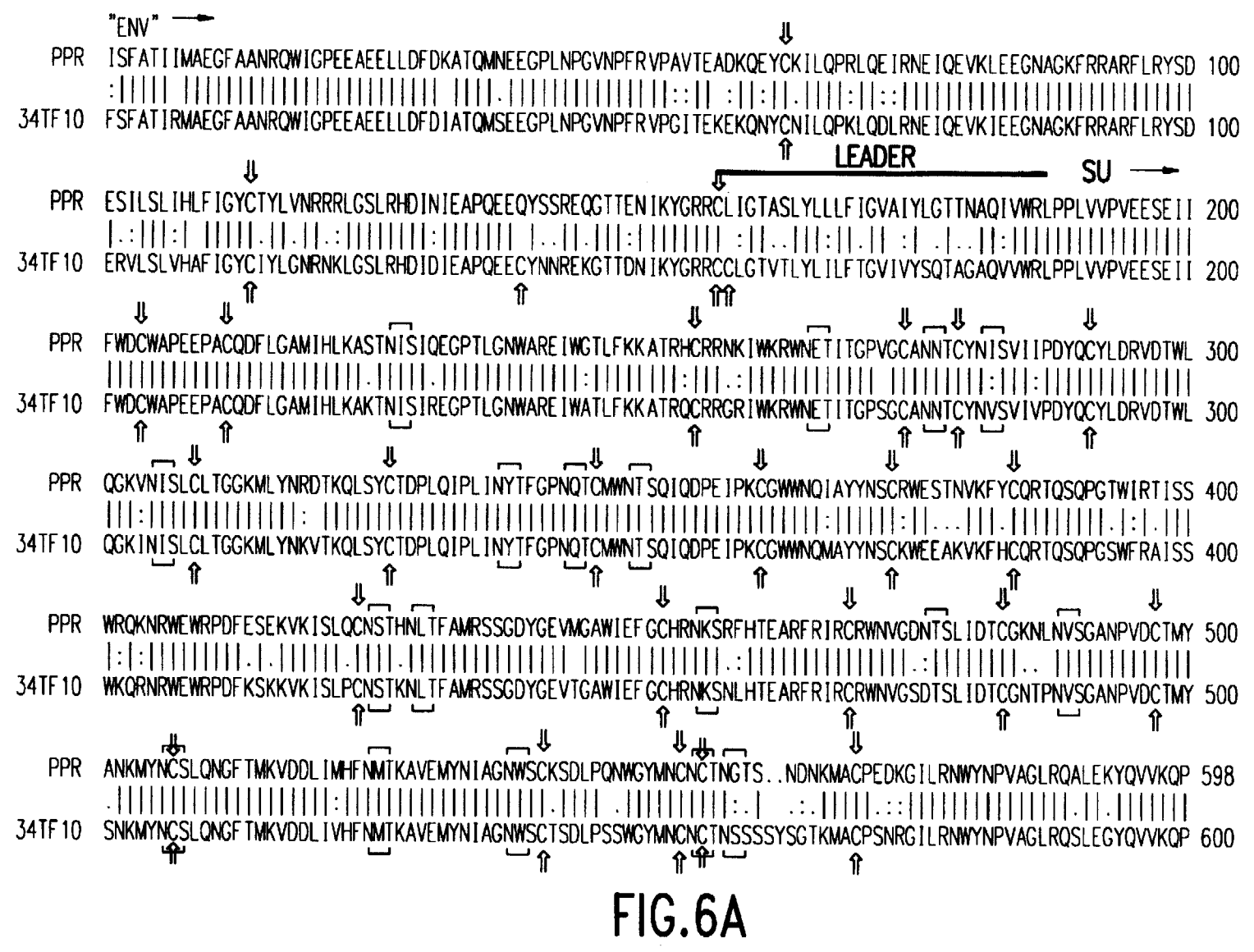

Although hydrophobic in both clones, the presumed leader sequence was contained within variable region 2. Two short variable regions, V5 and V6, were found within hydrophilic regions of the FIV TM protein. V5 was contained within a hydrophilic area that spanned the two hydrophobic regions of this protein, while V6 was located at the presumed cytoplasmic tail. Although there was considerable variability in the predicted amino acid sequence of the env gene, the glycosylation sites and cysteine residues were highly conserved, with 31 of 33 cysteines and 21 of 22 glycosylation sites being maintained FIGS. 6A–6B. For all env regions, the percentage of amino acid similarity was substantially higher than the percentage of amino acid identity, particularly for the presumed L and TM proteins (Table 1).

Small ORFs. A number of small ORFs were present in both clones. Six ORFs (1, 2, D, F, I, and H) were greater than 120 bp in length and were conserved in both FIV clones (FIG. 3B, Table 1). ORF 1 was similar to size and location to the vif gene of the primate lentiviruses. However, no nucleotide sequence homology was evident. ORF 1 was conserved between the two clones to nearly the same degree as were the gag and pol genes (Table 1). ORF 2 resembled the first exon of tat by its size and location in the FIV genome (L. Chakrabarti et al., 1987 Nature (Lond.) 328:543–547; M. Fukasawa, et al., 1988 Nature (Lond.) 333:457–461; M. Guyader et al., 1987 Nature (Lond.) 326:662–669; I. Ratner et al., 1985 Nature (Lond.) 313:277–284; R. Sanchez-Pescador et al., 1985 Science 227:484–492; R. Talbott et al., 1989; S. Wain-Hobson et al., 1985 Cell 40:9–17; all incorporated herein by reference). Again, no nucleotide sequence homology was evident between ORF 2 and the primate Tat proteins. ORF 2 prematurely terminated in the 34TF10 clone due to a transition of a G to an A residue, resulting in the generation of a stop codon (R. Talbott et al., 1989, incorporated herein by reference) (FIG. 7). Thus, this ORF of the PPR clone coded for a polypeptide that was approximately twice the size of that encoded by the 34TF10 clone. However, the premature stop codon of the 34TF10 clone does not appear to have a role in determining host cell range. This is because another clone of the Petaluma isolate (Olmsted et al., 1989, incorporated herein by reference) has been reported to have a host cell range similar to the 34TF10 clone but, like the PPR clone, codes for a full-length ORF 2.

Splice donor and acceptor sites. PCR amplification of cDNA was used to identify the splice donor and acceptor sites from two subgenomic mRNA species of clone 34TF10 (FIG. 8). Immediately upstream from the gag coding sequence, a 5' splice donor site, common to both mRNA species, was found at base 604 of the 34TF10 sequence (R. Talbott et al., 1989, incorporated herein by reference). The first mRNA species was spliced at least once, with a splice acceptor at base 5921, 70 bases 5' to the start codon of the putative tat product. The second mRNA species was spliced at least twice, using the common 5' splice donor site at base 604 and an acceptor site at base 5188. This acceptor site was located 68 nucleotides prior to the putative start of Vif. Seventy bases downstream, another classic splice donor site at base 5255 was used in this species. The message was then resumed at the previously described ORF 2 acceptor site, using base 5921. In neither of the mRNA species were ORFs maintained across the splice junctions. These 34TF10 splice acceptor sites were conserved in PPR.

Two distinct FIV isolates are compared herein. These two isolates originated from different cats at distinct geographic locations and varied in their in vitro host cell range and their envelope proteins. Env variability has been used to determine the genetic similarity of HIV isolates (G. Myers et al., eds. 1989 *Human Retroviruses and Aids*. Theoretical Biology and Biophysics, Los Alamos, N. Mex., incorporated herein by reference), with the most distantly related isolates having an env variability of greater than 12% at the nucleic acid level. Thus, by the standards set for HIV, the two FIV clones, with an env diversity of 14%, would be considered instantly related isolates (Myers et al., eds., 1989, incorporated herein by reference).

It is important to note that both FIV clones were infectious. Infectious clones have constraints on their sequence variability, as critical viral functions must be maintained for the virus to remain viable. Thus, essential functional domains of the FIV should be conserved between these two clones. However, the FIV clones 34TF10 and PPR differed in an important biological property, their in vitro host cell range. In other retroviruses, host cell alterations have resulted from changes in the LTR and/or env regions of the virus (P. Chatis et al., 1983 Proc. Natl. Acad. Sci. USA 80:4408–4411; P. Chatis et al., 1984 J. Virol. 52:248–254; C. Holland et al., 1985 J. Virol. 53:158–165; C. Holland et al., 1985 J. Virol. 53:152–157; A. Ishimoto, et al., 1985 Virology 141:30–42; M. Lung et al., 1983 J. Virol. 45:275–290; J. Overbaugh et al., 1988 Nature (Lond.) 332:731–734; N. Riedel et al., 1988 Proc. Natl. Acad. Sci. USA 85:2758–2762; M. Vogt et al., 1985 J. Virol. 55:184–192; all incorporated herein by reference). It is likely that one or both of these regions are also responsible for the host cell range of FIV.

Similar to other lentiviruses, the gag and pol regions of FIV were highly conserved, up to 98% at the amino acid level. The pol gene of FIV, like that of visna virus and equine infectious anemia virus, had the potential of coding for an extra proteaselike gene product, termed PrL. Since this putative gene product is conserved to the same degree as the other gag-pol products of FIV and occurs in a group of viruses known for their efficient utilization of genetic material, it is likely that this putative gene product does have a function and is not being carried as a pseudogene.

The LTRs of retroviruses determine, in part, the rate of viral transcription. Not surprisingly, with a 93% nucleic acid identity, many of the structural elements of the LTR were conserved between the two FIV clones. The identification of conserved enhancer-promoter binding sites does not ensure that they function in FIV transcription. However, these sites are located in the U3 region just upstream from the TATA site and are in an ideal location to exert enhancer function. Of particular interest is the presence of both AP-1 and AP-4 sites n the FIV clones, since they have been shown, in other systems, to synergistically enhance transcription (N. Mermod et al., 1988 Nature (Lond.) 332:557–561, incorporated herein by reference). An ATF-binding site, which is also known as the cyclic AMP response element, was conserved in both clones. The ATF protein has been shown to establish a preinitiation complex through interactions with its DNA-binding site and the mammalian TATA factor TFID (T. Hai et al., 1988 Cell 54:1043–1051; M. Horikoshi et al., 1988 Cell 54:1033–1042, both incorporated herein by reference). The virally encoded trans-activating protein p38$^{tax}$ of bovine leukemia virus may enhance transcription by binding to an ATF-binding site in its LTR (I. Hatoh et al., 1989 EMBO J. 8:497–503, incorporated herein by reference). Thus, it is possible that an FIV-encoded protein may interact with the ATF-binding site in a manner similar to p38$^{tax}$.

A classic CCAAT promoter element was found in the PPR clone but not in the 34TF10 clone. Nucleotide substitutions anywhere within this element dramatically decrease transcription (R. Myers et al., Science 232:613–618, incorporated herein by reference). Thus, this may be an important difference between these two clones.

The 34TF10 clone has an 8 of 10 match with the consensus sequence of the NF-KB binding site sequence in two functionally critical bases, the two 3' C residues (E. Bohnlein et al., 1988 Cell 53:827–836; J. Hiscott et al., 1989 J. Virol. 63:2557–2566; R. Sen and D. Baltimore, 1986 Cell 46:705–716, all incorporated herein by reference). This change may be interpreted in three ways: (i) the putative NF-KB binding site is not really an enhancer binding site; (ii) the feline NF-KB protein recognizes a slightly different nucleic acid sequence; or (iii) an unknown enhancer protein, which is related to NF-KB, binds to this site. To complicate things further, the greatest LTR diversity between these two clones also occurred at the putative NF-KB binding site. The LBP-1 site, also called UBP-1, was found in the 34TF10 clone but was not maintained in the PPR clone. Similar to the HIV LTR, the putative LBP-1 binding site of FIV was in close approximation to the TATA box. In HIV, the binding of the LBP-1 protein greatly increases transcription (K. Jones et al., 1988 Genes Dev. 2:1101–1114, incorporated herein by reference).

Although the LTR nucleic acid sequence of these two clones was highly conserved, some changes occurred in potentially critical areas. In particular, changes in the putative NF-KB binding site, one of the AP-4 binding sites, the LBP-1 site, and the CCAAT promoter element may be of functional importance. It is possible that one or several of these changes are responsible for the different host cell ranges of these two FIV clones.

Of the large ORFs, the greatest predicted amino acid diversity was found in the env gene. There appeared to be certain constraints on this sequence variability, as both the cysteines and glycosylation sites were highly conserved. Additionally, many of the amino acid changes were of a conservative nature, as reflected in the high degree of amino acid similarity between the Env proteins.

The predicted amino acid changes of the env gene clustered in certain protein regions, allowing the identification of variable and conserved sites. This clustering of Env amino acid diversity appears to be a property of lentiviruses (M. Alizon et al., 1986 Cell 46:63–74; M. Braun et al., 1987 J. Virol. 61:4046–4054; C. Gurgo et al., 1988 Virology 164:531–536; D. Ho et al., 1988 Science 239:1021–1023; S. Modrow et al., 1987 J. Virol. 61:570–578; S. Payne et al., 1987 Virol 161:321–331; all incorporated herein by reference). The variable regions of lentiviruses tend to occur at immunodominant sites. These regions may serve to divert immunologic recognition away from the conserved areas, which are more likely to encode important viral functions. The diversion of the immune system from the conserved regions may allow the virus to escape immune surveillance or to delay its neutralization. Through the use of recombinant DNA technology, it may be possible to produce an efficacious and broadly reactive lentivirus vaccine. The identification of the conserved regions of env is important for the development of such a vaccine for FIV.

The second small ORF, ORF 2, is in the same location and is similar in size to the first exon of tat in the primate lentivirus. In the 34TF10 clone of the Petaluma isolate, this ORF terminated prematurely. This shortened ORF 2 appears to be unique to the 34TF10 clone, since this ORF was nearly twice as long in two other FIC clones (the PPR clone of this study and a second infectious clone of the Petaluma isolate [R. Olmsted et al., 1989]). Obviously, the full-length product of the putative tat gene is not needed for viral infectivity, since both the PPR and the 34TF10 clones were infectious.

As further evidence that these products are actually produced, we have identified two mRNA species that utilize splice acceptor sites just 5' to the initiation codons of ORF 1 and ORF 2 of the 34TF10 clone. These sites are also conserved in the PPR clone.

Four other small ORFs were conserved between the two FIV clones (D, F, I, and H). Since they were found in both of these diverse FIV clones, it is possible that they have an important FIV function.

The invention now being fully described, it will be apparent to one of ordinary skill in the art that many changes and modifications can be made thereto without departing from the spirit or scope of the appended claims.

TABLE 1

FIV sequence comparison[a]

| Gene and proteins | % Nucleic acid identity | % Amino acid identity | % Amino acid similarity |
|---|---|---|---|
| gag | 95 | 96 | 98 |
| Matrix | 95 | 97 | 97 |
| Capsid | 95 | 96 | 99 |
| Nucleocapsid | 94 | 92 | 96 |
| pol | 95 | 95 | 97 |
| Protease | 95 | 98 | 98 |
| Reverse transcriptase | 94 | 95 | 97 |
| Proteaselike protein | 94 | 92 | 95 |
| Integrase | 95 | 95 | 98 |
| env | 86 | 85 | 92 |
| L | 87 | 82 | 91 |
| Leader | 67 | 55 | 69 |
| Surface | 88 | 87 | 92 |
| Transmembrane | 84 | 87 | 95 |
| Small ORFs | | | |
| 1 | 92 | 90 | 94 |
| 2 | 78 | 73 | 86 |
| D | 85 | 72 | 77 |
| F | 80 | 46 | 71 |
| H | 85 | 66 | 78 |
| I | 83 | 58 | 75 |

[a]Comparison of the nucleic acid identity, deduced amino acid identity, and predicted amino acid similarity from various protein coding regions of the PPR and 34TF10 clones of FIV.

SUMMARY OF SEQUENCES

Sequence ID No. 1 is the nucleotide sequence for Clone 34, found in FIG. 4, lines 1, 3, and 5.

Sequence ID No. 2 is the nucleotide sequence for Clone P, as found in FIG. 4, lines 2, 4, and 6.

5,736,378

Sequence ID No. 3 is the amino acid sequence of Clone PPR found in FIG. 6, lines 1, 3, 5, 7, 9, 11, 13, 15, and 17.
Sequence ID No. 4 is the amino acid sequence of Clone 34TF10 found in FIG. 6, lines 2, 4, 6, 8, 10, 12, 14, 16, and 18.
Sequence ID No. 5 is the nucleotide and deduced amino acid sequence of Clone 34TF, found in FIG. 7, lines 1, 2, 5, 6, 9, 10, 13, and 14.
Sequence ID No. 6 is the deduced amino acid sequence of Clone 34TF found in FIG. 7, lines 1, 5, and 9.
Sequence ID No. 7 is the nucleotide and deduced amino acid sequence of Clone PPR, found in FIG. 7, lines 3, 4, 7, 8, 11, 12, 15, and 16.
Sequence ID No. 8 is the deduced amino acid sequence of Clone PPR, found in FIG. 7, lines 4, 8, 12, and 16.
Sequence ID No. 9 is the nucleotide sequence of Clone 34, found in FIG. 9. The locations indicated under Section (ix) (B) Location indicate the nucleotides which encode the gene products seen in FIG. 9 as amino acid sequences.
Sequence ID No. 10 is the nucleotide sequence of Clone P, found in FIG. 10.

What is claimed is:

1. An isolated and purified nucleic acid encoding the feline immunodeficiency virus designated $FIV_{PPR}$, wherein said nucleic acid consists of the sequence of SEQ ID NO.: 10.

2. A host cell transfected or transformed with the nucleic acid of claim 1.

3. The host cell transfected or transformed in claim 2 wherein the cell is mammalian.

4. An isolated and purified feline immunodeficiency virus designated $FIV_{PPR}$ containing the nucleotide sequence of SEQ ID NO.: 10.

5. An infected cell line producing the virus of claim 4.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 355 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: 34

( i x ) FEATURE:
        ( A ) NAME/KEY: 5'UTR
        ( B ) LOCATION: 1..355

( x i ) SEQUENCE DESCRIPTION: SEQ ID NO:1:

```
TGGGATGAGT ACTGGAACCC TGAAGAAATA GAAAGAATGC TTATGGACTA GGGACTGTTT      60

ACGAACAAAT GATAAAAGGA AATAGCTGAG CATGACTCAT AGTTAAAGCG CTAGCAGCTG     120

CTTAACCGCA AAACCACATC CTATGTAAAG CTTGCTAATG ACGTATAAGT TGTTCCATTG     180

TAAGAGTATA TAACCAGTGC TTTGTGAAAC TTCGAGGAGT CTCTTTGTTG AGGACTTTTG     240

AGTTCTCCCT TGAGGCTCCC ACAGATACAA TAAATATTTG AGATTGAACC CTGTCGAGTA     300

TCTGTGTAAT CTTTTTTACC TGTGAGGTCT CGGAATCCGG GCCGAGAACT TCGCA          355
```

( 2 ) INFORMATION FOR SEQ ID NO:2:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: P ( i x ) FEATURE:
        ( A ) NAME/KEY: 5'UTR
        ( B ) LOCATION: 1..354

( x i ) SEQUENCE DESCRIPTION: SEQ ID NO:2:

```
TGGGATGAGT ATTGGGACCT TGAAGAAATA GAAAGATTGC TTATGGACTA AGAACTGTCA      60

CAAACAAATG ATAAATGGAA ACAGCTGAAC ATGACTCATA GTTAAAGCGC TAGCAGCTGC     120

TTAACCGCAA AACCACATCC TATGTAAAGC TTGCCAATGA CGTTTAATTT GCTCCACTGT     180

AAGAGTATAT AATCAGTGCT TTGTGAAGCT TCGAAGAGTC TCTCTGCTGA GGACTTTCGA     240
```

```
GTTCTCCCTT GAGGCTCCCA CAGATACAAT AAATATTTGA GATTGAACCC TGTCAAGTAT      300

CTGTGTAGTC TTTTCTACCT GTGAGGTCTC GGAATCCGGG CCGAGAACTT CGCA            354
```

( 2 ) INFORMATION FOR SEQ ID NO:3:

( i ) SEQUENCE CHARACTERISTICS:
        ( A ) LENGTH: 1724 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: PPR ( i x ) FEATURE:
        ( A ) NAME/KEY: Protein
        ( B ) LOCATION: 1..861

( x i ) SEQUENCE DESCRIPTION: SEQ ID NO:3:

```
Ile Ser Phe Ala Thr Ile Ile Met Ala Glu Gly Phe Ala Ala Asn Arg
 1           5                  10                  15

Gln Trp Ile Gly Pro Glu Glu Ala Glu Leu Leu Asp Phe Asp Lys
            20                  25                  30

Ala Thr Gln Met Asn Glu Glu Gly Pro Leu Asn Pro Gly Val Asn Pro
            35                  40                  45

Phe Arg Val Pro Ala Val Thr Glu Ala Asp Lys Gln Glu Tyr Cys Lys
            50                  55                  60

Ile Leu Gln Pro Arg Leu Gln Glu Ile Arg Asn Glu Ile Gln Glu Val
 65                 70                  75                  80

Lys Leu Glu Glu Gly Asn Ala Gly Lys Phe Arg Arg Ala Arg Phe Leu
                85                  90                  95

Arg Tyr Ser Asp Phe Ser Phe Ala Thr Ile Arg Met Ala Glu Gly Phe
                100                 105                 110

Ala Ala Asn Arg Gln Trp Ile Gly Pro Glu Glu Ala Glu Leu Leu
            115                 120                 125

Asp Phe Asp Ile Ala Thr Gln Met Ser Glu Glu Gly Pro Leu Asn Pro
    130                 135                 140

Gly Val Asn Pro Phe Arg Val Pro Gly Ile Thr Glu Lys Glu Lys Gln
145                 150                 155                 160

Asn Tyr Cys Asn Ile Leu Gln Pro Lys Leu Gln Asp Leu Arg Asn Glu
                165                 170                 175

Ile Gln Glu Val Lys Leu Glu Glu Gly Asn Ala Gly Lys Phe Arg Arg
                180                 185                 190

Ala Arg Phe Leu Arg Tyr Ser Asp Glu Ser Ile Leu Ser Leu Ile His
        195                 200                 205

Leu Phe Ile Gly Tyr Cys Thr Tyr Leu Val Asn Arg Arg Leu Gly
    210                 215                 220

Ser Leu Arg His Asp Ile Asn Ile Glu Ala Pro Gln Glu Glu Gln Tyr
225                 230                 235                 240

Ser Ser Arg Glu Gln Gly Thr Thr Glu Asn Ile Lys Tyr Gly Arg Arg
                245                 250                 255

Cys Leu Ile Gly Thr Ala Ser Leu Tyr Leu Leu Phe Ile Gly Val
                260                 265                 270

Ala Ile Tyr Leu Gly Thr Thr Asn Ala Gln Ile Val Trp Arg Leu Pro
        275                 280                 285

Pro Leu Val Val Pro Val Glu Glu Ser Glu Ile Ile Glu Arg Val Leu
    290                 295                 300
```

```
Ser  Leu  Val  His  Ala  Phe  Ile  Gly  Tyr  Cys  Ile  Tyr  Leu  Gly  Asn  Arg
305                 310                 315                           320

Asn  Lys  Leu  Gly  Ser  Leu  Arg  His  Asp  Ile  Asp  Ile  Glu  Ala  Pro  Gln
                    325                 330                      335

Glu  Glu  Cys  Tyr  Asn  Asn  Arg  Glu  Lys  Gly  Thr  Thr  Asp  Asn  Ile  Lys
               340                      345                      350

Tyr  Gly  Arg  Arg  Cys  Cys  Leu  Gly  Thr  Val  Thr  Leu  Tyr  Leu  Ile  Leu
          355                      360                      365

Phe  Thr  Gly  Val  Ile  Val  Tyr  Ser  Gln  Thr  Ala  Gly  Ala  Gln  Val  Val
          370                 375                      380

Trp  Arg  Leu  Pro  Pro  Leu  Val  Val  Pro  Val  Glu  Glu  Ser  Glu  Ile  Ile
385                      390                      395                      400

Phe  Trp  Asp  Cys  Trp  Ala  Pro  Glu  Glu  Pro  Ala  Cys  Gln  Asp  Phe  Leu
               405                      410                           415

Gly  Ala  Met  Ile  His  Leu  Lys  Ala  Ser  Thr  Asn  Ile  Ser  Ile  Gln  Glu
               420                 425                      430

Gly  Pro  Thr  Leu  Gly  Asn  Trp  Ala  Arg  Glu  Ile  Trp  Gly  Thr  Leu  Phe
          435                 440                      445

Lys  Lys  Ala  Thr  Arg  His  Cys  Arg  Arg  Asn  Lys  Ile  Trp  Lys  Arg  Trp
450                      455                 460

Asn  Glu  Thr  Ile  Thr  Gly  Pro  Val  Gly  Cys  Ala  Asn  Asn  Thr  Cys  Tyr
465                      470                 475                           480

Asn  Ile  Ser  Val  Ile  Ile  Pro  Asp  Tyr  Gln  Cys  Tyr  Leu  Asp  Arg  Val
                    485                 490                           495

Asp  Thr  Trp  Leu  Phe  Trp  Asp  Cys  Trp  Ala  Pro  Glu  Glu  Pro  Ala  Cys
               500                 505                           510

Gln  Asp  Phe  Leu  Gly  Ala  Met  Ile  His  Leu  Lys  Ala  Lys  Thr  Asn  Ile
          515                 520                      525

Ser  Ile  Arg  Glu  Gly  Pro  Thr  Leu  Gly  Asn  Trp  Ala  Arg  Glu  Ile  Trp
530                      535                      540

Ala  Thr  Leu  Phe  Lys  Lys  Ala  Thr  Arg  Gln  Cys  Arg  Arg  Gly  Arg  Ile
545                 550                      555                           560

Trp  Lys  Arg  Trp  Asn  Glu  Thr  Ile  Thr  Gly  Pro  Ser  Gly  Cys  Ala  Asn
               565                      570                           575

Asn  Thr  Cys  Tyr  Asn  Val  Ser  Val  Ile  Val  Pro  Asp  Tyr  Gln  Cys  Tyr
               580                 585                      590

Leu  Asp  Arg  Val  Asp  Thr  Trp  Leu  Gln  Gly  Lys  Val  Asn  Ile  Ser  Leu
          595                      600                 605

Cys  Leu  Thr  Gly  Gly  Lys  Met  Leu  Tyr  Asn  Arg  Asp  Thr  Lys  Gln  Leu
     610                 615                      620

Ser  Tyr  Cys  Thr  Asp  Pro  Leu  Gln  Ile  Pro  Leu  Ile  Asn  Tyr  Thr  Phe
625                      630                      635                      640

Gly  Pro  Asn  Gln  Thr  Cys  Met  Trp  Asn  Thr  Ser  Gln  Ile  Gln  Asp  Pro
                    645                      650                      655

Glu  Ile  Pro  Lys  Cys  Gly  Trp  Trp  Asn  Gln  Ile  Ala  Tyr  Tyr  Asn  Ser
               660                      665                      670

Cys  Arg  Trp  Glu  Ser  Thr  Asn  Val  Lys  Phe  Tyr  Cys  Gln  Arg  Thr  Gln
          675                      680                 685

Ser  Gln  Pro  Gly  Thr  Trp  Ile  Arg  Thr  Ile  Ser  Ser  Gln  Gly  Lys  Ile
     690                      695                      700

Asn  Ile  Ser  Leu  Cys  Leu  Thr  Gly  Gly  Lys  Met  Leu  Tyr  Asn  Lys  Val
705                 710                      715                           720

Thr  Lys  Gln  Leu  Ser  Tyr  Cys  Thr  Asp  Pro  Leu  Gln  Ile  Pro  Leu  Ile
```

-continued

|  |  |  |  |  | 725 |  |  |  |  | 730 |  |  |  |  | 735 |  |
|---|---|---|---|---|---|---|---|---|---|---|---|---|---|---|---|---|
| Asn | Tyr | Thr | Phe 740 | Gly | Pro | Asn | Gln 745 | Thr | Cys | Met | Trp | Asn | Thr 750 | Ser | Gln |
| Ile | Gln | Asp 755 | Pro | Glu | Ile | Pro 760 | Lys | Cys | Gly | Trp | Trp 765 | Asn | Gln | Met | Ala |
| Tyr | Tyr 770 | Asn | Ser | Cys | Lys | Trp 775 | Glu | Glu | Ala | Lys | Val 780 | Lys | Phe | His | Cys |
| Gln 785 | Arg | Thr | Gln | Ser | Gln 790 | Pro | Gly | Ser | Trp | Phe 795 | Arg | Ala | Ile | Ser | Ser 800 |
| Trp | Arg | Gln | Lys | Asn 805 | Arg | Trp | Glu | Trp | Arg 810 | Pro | Asp | Phe | Glu | Ser 815 | Glu |
| Lys | Val | Lys | Ile 820 | Ser | Leu | Gln | Cys | Asn 825 | Ser | Thr | His | Asn | Leu 830 | Thr | Phe |
| Ala | Met | Arg 835 | Ser | Ser | Gly | Asp | Tyr 840 | Gly | Glu | Val | Met | Gly 845 | Ala | Trp | Ile |
| Glu | Phe 850 | Gly | Cys | His | Arg | Asn 855 | Lys | Ser | Arg | Phe | His 860 | Thr | Glu | Ala | Arg |
| Phe 865 | Arg | Ile | Arg | Cys | Arg 870 | Trp | Asn | Val | Gly | Asp 875 | Asn | Thr | Ser | Leu | Ile 880 |
| Asp | Thr | Cys | Gly | Lys 885 | Asn | Leu | Asn | Val | Ser 890 | Gly | Ala | Asn | Pro | Val 895 | Asp |
| Cys | Thr | Met | Tyr 900 | Trp | Lys | Gln | Arg | Asn 905 | Arg | Trp | Glu | Trp | Arg 910 | Pro | Asp |
| Phe | Lys | Ser 915 | Lys | Lys | Val | Lys | Ile 920 | Ser | Leu | Pro | Cys | Asn 925 | Ser | Thr | Lys |
| Asn | Leu 930 | Thr | Phe | Ala | Met | Arg 935 | Ser | Ser | Gly | Asp | Tyr 940 | Gly | Glu | Val | Thr |
| Gly 945 | Ala | Trp | Ile | Glu | Phe 950 | Gly | Cys | His | Arg | Asn 955 | Lys | Ser | Asn | Leu | His 960 |
| Thr | Glu | Ala | Arg | Phe 965 | Arg | Ile | Arg | Cys | Arg 970 | Trp | Asn | Val | Gly | Ser 975 | Asp |
| Thr | Ser | Leu | Ile 980 | Asp | Thr | Cys | Gly | Asn 985 | Thr | Pro | Asn | Val | Ser 990 | Gly | Ala |
| Asn | Pro | Val 995 | Asp | Cys | Thr | Met | Tyr 1000 | Ala | Asn | Lys | Met | Tyr 1005 | Asn | Cys | Ser |
| Leu | Gln | Asn 1010 | Gly | Phe | Thr | Met | Lys 1015 | Val | Asp | Asp | Leu | Ile 1020 | Met | His | Phe |
| Asn 1025 | Met | Thr | Lys | Ala | Val 1030 | Glu | Met | Tyr | Asn | Ile 1035 | Ala | Gly | Asn | Trp | Ser 1040 |
| Cys | Lys | Ser | Asp | Leu 1045 | Pro | Gln | Asn | Trp | Gly 1050 | Tyr | Met | Asn | Cys 1055 | Asn | Cys |
| Thr | Asn | Gly | Thr 1060 | Ser | Asn | Asp | Asn | Lys 1065 | Met | Ala | Cys | Pro | Glu 1070 | Asp | Lys |
| Gly | Ile | Leu | Arg 1075 | Asn | Trp | Tyr | Asn | Pro 1080 | Val | Ala | Gly | Leu | Arg 1085 | Gln | Ala |
| Leu | Glu | Lys | Tyr 1090 | Gln | Val | Val | Lys 1095 | Gln | Pro | Ser | Asn | Lys 1100 | Met | Tyr | Asn |
| Cys 1105 | Ser | Leu | Gln | Asn | Gly 1110 | Phe | Thr | Met | Lys | Val 1115 | Asp | Asp | Leu | Ile | Val 1120 |
| His | Phe | Asn | Met | Thr 1125 | Lys | Ala | Val | Glu | Met 1130 | Tyr | Asn | Ile | Ala | Gly 1135 | Asn |
| Trp | Ser | Cys | Thr 1140 | Ser | Asp | Leu | Pro | Ser 1145 | Trp | Gly | Tyr | Met | Asn 1150 | Cys |  |

```
Asn Cys Thr Asn Ser Ser Ser Ser Tyr Ser Gly Thr Lys Met Ala Cys
         1155                1160                1165
Pro Ser Asn Arg Gly Ile Leu Arg Asn Trp Tyr Asn Pro Val Ala Gly
   1170                1175                1180
Leu Arg Gln Ser Leu Glu Gln Tyr Gln Val Val Lys Gln Pro Glu Tyr
1185                1190                1195                1200
Ile Val Val Pro Thr Glu Val Met Thr Tyr Lys Tyr Lys Gln Lys Arg
              1205                1210                1215
Ala Ala Ile His Ile Met Leu Ala Leu Ala Thr Val Leu Ser Ile Ala
            1220                1225                1230
Gly Ala Gly Thr Gly Ala Thr Ala Ile Gly Met Val Thr Gln Tyr Gln
         1235                1240                1245
Gln Val Leu Ala Thr His Gln Glu Ala Leu Asp Lys Ile Thr Glu Ala
         1250                1255                1260
Leu Lys Ile Asn Asn Leu Arg Leu Val Thr Leu Glu His Gln Met Leu
1265                1270                1275                1280
Val Ile Gly Leu Lys Val Glu Ala Ile Glu Lys Phe Leu Tyr Thr Ala
              1285                1290                1295
Phe Ala Asp Tyr Leu Leu Val Pro Glu Glu Val Met Glu Tyr Lys Pro
         1300                1305                1310
Arg Arg Lys Arg Ala Ala Ile His Val Met Leu Ala Leu Ala Thr Val
         1315                1320                1325
Leu Ser Ile Ala Gly Ala Gly Thr Gly Ala Thr Ala Ile Gly Met Val
         1330                1335                1340
Thr Gln Tyr His Gln Val Leu Ala Thr His Gln Glu Ala Ile Glu Lys
1345                1350                1355                1360
Val Thr Gly Ala Leu Lys Ile Asn Asn Leu Arg Leu Val Thr Leu Glu
              1365                1370                1375
His Gln Val Leu Val Ile Gly Leu Lys Val Glu Ala Met Glu Lys Phe
         1380                1385                1390
Leu Tyr Thr Ala Phe Ala Met Gln Glu Leu Gly Cys Asn Gln Asn Gln
         1395                1400                1405
Phe Phe Cys Glu Ile Pro Lys Glu Leu Trp Leu Arg Tyr Asn Met Thr
   1410                1415                1420
Leu Asn Gln Thr Ile Trp Asn His Gly Asn Ile Thr Leu Gly Glu Trp
1425                1430                1435                1440
Tyr Asn Gln Thr Lys Tyr Leu Gln Gln Lys Phe Tyr Glu Ile Ile Met
              1445                1450                1455
Asp Ile Glu Gln Asn Asn Val Gln Gly Lys Gln Gly Leu Gln Lys Leu
         1460                1465                1470
Gln Asn Trp Gln Asp Trp Met Gly Trp Ile Gly Lys Ile Pro Gln Tyr
         1475                1480                1485
Leu Lys Gly Leu Leu Gly Gly Ile Leu Gly Met Gln Glu Leu Gly Cys
   1490                1495                1500
Asn Gln Asn Gln Phe Phe Cys Lys Ile Pro Leu Glu Leu Trp Thr Arg
1505                1510                1515                1520
Tyr Asn Met Thr Ile Asn Gln Thr Ile Trp Asn His Gly Asn Ile Thr
              1525                1530                1535
Leu Gly Glu Trp Tyr Asn Gln Thr Lys Asp Leu Gln Gln Lys Phe Tyr
         1540                1545                1550
Glu Ile Ile Met Asp Ile Glu Gln Asn Asn Val Gln Gly Lys Thr Gly
            1555                1560                1565
Ile Gln Gln Leu Gln Lys Trp Glu Asp Trp Val Arg Trp Ile Gly Asn
         1570                1575                1580
```

| Ile | Pro | Gln | Tyr | Leu | Lys | Gly | Leu | Leu | Gly | Ile | Leu | Gly | Ile | Gly |
| 1585 | | | | 1590 | | | | | 1595 | | | | | 1600 |

Leu Gly Ile Leu Leu Leu Ile Leu Cys Leu Pro Thr Leu Val Asp Cys
            1605                1610                1615

Ile Arg Asn Cys Ile Ser Lys Val Leu Gly Tyr Thr Val Ile Ala Met
            1620            1625            1630

Pro Glu Ile Asp Asp Glu Glu Thr Val Gln Met Glu Leu Arg Lys
        1635            1640            1645

Asn Gly Arg Gln Cys Gly Met Ser Glu Lys Glu Glu Ile Gly Leu
        1650            1655            1660

Gly Val Leu Leu Leu Ile Leu Cys Leu Pro Thr Leu Val Asp Cys Ile
1665            1670            1675            1680

Arg Asn Cys Ile His Lys Ile Leu Gly Tyr Thr Val Ile Ala Met Pro
            1685            1690            1695

Glu Val Glu Gly Glu Glu Ile Gln Pro Gln Met Glu Leu Arg Arg Asn
            1700            1705            1710

Gly Arg Gln Cys Gly Met Ser Glu Lys Glu Glu Glu
            1715            1720

( 2 ) INFORMATION FOR SEQ ID NO:4:

( i ) SEQUENCE CHARACTERISTICS:
        ( A ) LENGTH: 863 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: 34TF10

( i x ) FEATURE:
        ( A ) NAME/KEY: Protein
        ( B ) LOCATION: 1..863

( x i ) SEQUENCE DESCRIPTION: SEQ ID NO:4:

Phe Ser Phe Ala Thr Ile Arg Met Ala Glu Gly Phe Ala Ala Asn Arg
1           5               10              15

Gln Trp Ile Gly Pro Glu Glu Ala Glu Glu Leu Leu Asp Phe Asp Ile
            20              25              30

Ala Thr Gln Met Ser Glu Glu Gly Pro Leu Asn Pro Gly Val Asn Pro
            35              40              45

Phe Arg Val Pro Gly Ile Thr Glu Lys Glu Lys Gln Asn Tyr Cys Asn
    50              55              60

Ile Leu Gln Pro Lys Leu Gln Asp Leu Arg Asn Glu Ile Gln Glu Val
65              70              75              80

Lys Leu Glu Glu Gly Asn Ala Gly Lys Phe Arg Arg Ala Arg Phe Leu
            85              90              95

Arg Tyr Ser Asp Glu Arg Val Leu Ser Leu Val His Ala Phe Ile Gly
            100             105             110

Tyr Cys Ile Tyr Leu Gly Asn Arg Asn Lys Leu Gly Ser Leu Arg His
        115             120             125

Asp Ile Asp Ile Glu Ala Pro Gln Glu Glu Cys Tyr Asn Asn Arg Glu
    130             135             140

Lys Gly Thr Thr Asp Asn Ile Lys Tyr Gly Arg Arg Cys Cys Leu Gly
145             150             155             160

Thr Val Thr Leu Tyr Leu Ile Leu Phe Thr Gly Val Ile Val Tyr Ser
            165             170             175

```
Gln Thr Ala Gly Ala Gln Val Val Trp Arg Leu Pro Pro Leu Val Val
            180                 185                 190

Pro Val Glu Glu Ser Glu Ile Ile Phe Trp Asp Cys Trp Ala Pro Glu
            195                 200                 205

Glu Pro Ala Cys Gln Asp Phe Leu Gly Ala Met Ile His Leu Lys Ala
        210                 215                 220

Lys Thr Asn Ile Ser Ile Arg Glu Gly Pro Thr Leu Gly Asn Trp Ala
225                 230                 235                 240

Arg Glu Ile Trp Ala Thr Leu Phe Lys Lys Ala Thr Arg Gln Cys Arg
                245                 250                 255

Arg Gly Arg Ile Trp Lys Arg Trp Asn Glu Thr Ile Thr Gly Pro Ser
            260                 265                 270

Gly Cys Ala Asn Asn Thr Cys Tyr Asn Val Ser Val Ile Val Pro Asp
        275                 280                 285

Tyr Gln Cys Tyr Leu Asp Arg Val Asp Thr Trp Leu Gln Gly Lys Ile
    290                 295                 300

Asn Ile Ser Leu Cys Leu Thr Gly Gly Lys Met Leu Tyr Asn Lys Val
305                 310                 315                 320

Thr Lys Gln Leu Ser Tyr Cys Thr Asp Pro Leu Gln Ile Pro Leu Ile
                325                 330                 335

Asn Tyr Thr Phe Gly Pro Asn Gln Thr Cys Met Trp Asn Thr Ser Gln
            340                 345                 350

Ile Gln Asp Pro Glu Ile Pro Lys Cys Gly Trp Trp Asn Gln Met Ala
        355                 360                 365

Tyr Tyr Asn Ser Cys Lys Trp Glu Glu Ala Lys Val Lys Phe His Cys
    370                 375                 380

Gln Arg Thr Gln Ser Gln Pro Gly Ser Trp Phe Arg Ala Ile Ser Ser
385                 390                 395                 400

Trp Lys Gln Arg Asn Arg Trp Glu Trp Arg Pro Asp Phe Lys Ser Lys
                405                 410                 415

Lys Val Lys Ile Ser Leu Pro Cys Asn Ser Thr Lys Asn Leu Thr Phe
            420                 425                 430

Ala Met Arg Ser Ser Gly Asp Tyr Gly Glu Val Thr Gly Ala Trp Ile
        435                 440                 445

Glu Phe Gly Cys His Arg Asn Lys Ser Asn Leu His Thr Glu Ala Arg
    450                 455                 460

Phe Arg Ile Arg Cys Arg Trp Asn Val Gly Ser Asp Thr Ser Leu Ile
465                 470                 475                 480

Asp Thr Cys Gly Asn Thr Pro Asn Val Ser Gly Ala Asn Pro Val Asp
                485                 490                 495

Cys Thr Met Tyr Ser Asn Lys Met Tyr Asn Cys Ser Leu Gln Asn Gly
            500                 505                 510

Phe Thr Met Lys Val Asp Asp Leu Ile Val His Phe Asn Met Thr Lys
        515                 520                 525

Ala Val Glu Met Tyr Asn Ile Ala Gly Asn Trp Ser Cys Thr Ser Asp
    530                 535                 540

Leu Pro Ser Ser Trp Gly Tyr Met Asn Cys Asn Cys Thr Asn Ser Ser
545                 550                 555                 560

Ser Ser Tyr Ser Gly Thr Lys Met Ala Cys Pro Ser Asn Arg Gly Ile
                565                 570                 575

Leu Arg Asn Trp Tyr Asn Pro Val Ala Gly Leu Arg Gln Ser Leu Glu
            580                 585                 590

Gln Tyr Gln Val Val Lys Gln Pro Asp Tyr Leu Leu Val Pro Glu Glu
```

|     |     |     |     |     |     | 595 |     |     |     |     |     | 600 |     |     |     |     |     | 605 |     |
|---|---|---|---|---|---|---|---|---|---|---|---|---|---|---|---|---|---|---|---|

Val Met Glu Tyr Lys Pro Arg Arg Lys Arg Ala Ala Ile His Val Met
        610             615             620

Leu Ala Leu Ala Thr Val Leu Ser Ile Ala Gly Ala Gly Thr Gly Ala
625             630             635             640

Thr Ala Ile Gly Met Val Thr Gln Tyr His Gln Val Leu Ala Thr His
            645             650             655

Gln Glu Ala Ile Glu Lys Val Thr Gly Ala Leu Lys Ile Asn Asn Leu
        660             665             670

Arg Leu Val Thr Leu Glu His Gln Val Leu Val Ile Gly Leu Lys Val
        675             680             685

Glu Ala Met Glu Lys Phe Leu Tyr Thr Ala Phe Ala Met Gln Glu Leu
        690             695             700

Gly Cys Asn Gln Asn Gln Phe Phe Cys Lys Ile Pro Leu Glu Leu Trp
705             710             715             720

Thr Arg Tyr Asn Met Thr Ile Asn Gln Thr Ile Trp Asn His Gly Asn
            725             730             735

Ile Thr Leu Gly Glu Trp Tyr Asn Gln Thr Lys Asp Leu Gln Gln Lys
        740             745             750

Phe Tyr Glu Ile Ile Met Asp Ile Glu Gln Asn Asn Val Gln Gly Lys
        755             760             765

Thr Gly Ile Gln Gln Leu Gln Lys Trp Glu Asp Trp Val Arg Trp Ile
        770             775             780

Gly Asn Ile Pro Gln Tyr Leu Lys Gly Leu Leu Gly Gly Ile Leu Gly
785             790             795             800

Ile Gly Leu Gly Val Leu Leu Leu Ile Leu Cys Leu Pro Thr Leu Val
            805             810             815

Asp Cys Ile Arg Asn Cys Ile His Lys Ile Leu Gly Tyr Thr Val Ile
        820             825             830

Ala Met Pro Glu Val Glu Gly Glu Glu Ile Gln Pro Gln Met Glu Leu
        835             840             845

Arg Arg Asn Gly Arg Gln Cys Gly Met Ser Glu Lys Glu Glu Glu
850             855             860

( 2 ) INFORMATION FOR SEQ ID NO:5:

( i ) SEQUENCE CHARACTERISTICS:
        ( A ) LENGTH: 237 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: 34TF ( i x ) FEATURE:
        ( A ) NAME/KEY: CDS
        ( B ) LOCATION: 1..129

( x i ) SEQUENCE DESCRIPTION: SEQ ID NO:5:

```
ATG GAA GAA ATA ATA GTA TTA TTC AAT AGG GTC ACT GAG AAA CTA GAA        48
Met Glu Glu Ile Ile Val Leu Phe Asn Arg Val Thr Glu Lys Leu Glu
 1               5                  10                  15

AAA GAA TTA GCT ATC AGA ATA TTT GTA TTA GCA CAT CAA TTA GAA AGG        96
Lys Glu Leu Ala Ile Arg Ile Phe Val Leu Ala His Gln Leu Glu Arg
             20                  25                  30

GAC AAA GCT ATT AGA TTA CTA CAA GGA TTA TTT TGAAGATATA GATTTAAGAA      149
Asp Lys Ala Ile Arg Leu Leu Gln Gly Leu Phe
```

```
                    35              40
ACCCCGAGCA GATTATTGTT TATGTTGGTG GTGTTGCAGA TTCTATTATT GGCAGTTGCA                209

ATCTACATTA TCAATAACTA CTGCTTAG                                                   237
```

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Glu Glu Ile Ile Val Leu Phe Asn Arg Val Thr Glu Lys Leu Glu
 1               5                   10                  15

Lys Glu Leu Ala Ile Arg Ile Phe Val Leu Ala His Gln Leu Glu Arg
             20                  25                  30

Asp Lys Ala Ile Arg Leu Leu Gln Gly Leu Phe
             35                  40
```

( 2 ) INFORMATION FOR SEQ ID NO:7:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: PPR ( i x ) FEATURE:
        ( A ) NAME/KEY: CDS
        ( B ) LOCATION: 1..231

( x i ) SEQUENCE DESCRIPTION: SEQ ID NO:7:

```
ATG GAA GTA ATA CGG ATA TTT AAT AAG GTC GCT GAA AGA TTA GAC AAG          48
Met Glu Val Ile Arg Ile Phe Asn Lys Val Ala Glu Arg Leu Asp Lys
 1               5                   10                  15

GAA GCA GCC ATC AGG ATA TTT GTA TTA GCA CAT CAA TTA GAG AGG GAT          96
Glu Ala Ala Ile Arg Ile Phe Val Leu Ala His Gln Leu Glu Arg Asp
             20                  25                  30

AAA TTG ATT AGA CTT CTG CAA GGA CTA CTT TGG AGA CTG AGA TTT AGA         144
Lys Leu Ile Arg Leu Leu Gln Gly Leu Leu Trp Arg Leu Arg Phe Arg
             35                  40                  45

AAA CCT AAA TCA AAA GAT TGT TTA TGT TGG TTT TGC TGC AGA TTA TAT         192
Lys Pro Lys Ser Lys Asp Cys Leu Cys Trp Phe Cys Cys Arg Leu Tyr
         50                  55                  60

TAT TGG CAG TTG CAG TCT ACA TTA TCC ATA GAT ACT GCT TAG                 234
Tyr Trp Gln Leu Gln Ser Thr Leu Ser Ile Asp Thr Ala
 65                  70                  75
```

( 2 ) INFORMATION FOR SEQ ID NO:8:

( i ) SEQUENCE CHARACTERISTICS:
        ( A ) LENGTH: 77 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Glu Val Ile Arg Ile Phe Asn Lys Val Ala Glu Arg Leu Asp Lys
```

|   | 1 |   |   | 5 |   |   |   | 10 |   |   |   | 15 |   |
|---|---|---|---|---|---|---|---|---|---|---|---|---|---|
| Glu | Ala | Ala | Ile | Arg | Ile | Phe | Val | Leu | Ala | His | Gln | Leu | Glu | Arg | Asp |
|  |  |  | 20 |  |  |  |  | 25 |  |  |  | 30 |  |  |  |
| Lys | Leu | Ile | Arg | Leu | Leu | Gln | Gly | Leu | Leu | Trp | Arg | Leu | Arg | Phe | Arg |
|  |  |  | 35 |  |  |  | 40 |  |  |  |  | 45 |  |  |  |
| Lys | Pro | Lys | Ser | Lys | Asp | Cys | Leu | Cys | Trp | Phe | Cys | Cys | Arg | Leu | Tyr |
|  |  | 50 |  |  |  |  | 55 |  |  |  |  | 60 |  |  |  |
| Tyr | Trp | Gln | Leu | Gln | Ser | Thr | Leu | Ser | Ile | Asp | Thr | Ala |
| 65 |  |  |  |  | 70 |  |  |  |  | 75 |  |  |

( 2 ) INFORMATION FOR SEQ ID NO:9:

( i ) SEQUENCE CHARACTERISTICS:
        ( A ) LENGTH: 9472 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: 34

( i x ) FEATURE:
        ( A ) NAME/KEY: CDS
        ( B ) LOCATION: join(627..1976, 1868..5239, 5235..5987, 5991
          . . 6224, 6264..8831, 6710..6913)

( x i ) SEQUENCE DESCRIPTION: SEQ ID NO:9:

| TGGGATGAGT | ACTGGAACCC | TGAAGAAATA | GAAAGAATGC | TTATGGACTA | GGGACTGTTT | 60 |
| ACGAACAAAT | GATAAAAGGA | AATAGCTGAG | CATGACTCAT | AGTTAAAGCG | CTAGCAGCTG | 120 |
| CTTAACCGCA | AAACCACATC | CTATGTAAAG | CTTGCTAATG | ACGTATAAGT | TGTTCCATTG | 180 |
| TAAGAGTATA | TAACCAGTGC | TTTGTGAAAC | TTCGAGGAGT | CTCTTTGTTG | AGGACTTTTG | 240 |
| AGTTCTCCCT | TGAGGCTCCC | ACAGATACAA | TAAATATTTG | AGATTGAACC | CTGTCGAGTA | 300 |
| TCTGTGTAAT | CTTTTTTACC | TGTGAGGTCT | CGGAATCCGG | GCCGAGAACT | TCGCAGTTGG | 360 |
| CGCCCGAACA | GGACTTGATT | GAGAGTGATT | GAGGAAGTGA | AGCTAGAGCA | ATAGAAAGCT | 420 |
| GTTAAGCAGA | ACTCCTGCTG | ACCTAAATAG | GGAAGCAGTA | GCAGACGCTG | CTAACAGTGA | 480 |
| GTATCTCTAG | TGAAGCAGCA | TCGAGCTCAT | AATCAAGTCA | TTGTTTAAAG | GCCCAGATAA | 540 |
| ATTACATCTG | GTGACTCTTC | GCGGACCTTC | AAGCCAGGAG | ATTCGCCGAG | GGACAGTCAA | 600 |
| CAAGGTAGGA | GAGATTCTAC | AGCAACATGG | GGAATGGACA | GGGGCGAGAT | TGGAAAATGG | 660 |
| CCATTAAGAG | ATGTAGTAAT | GTTGCTGTAG | GAGTAGGGGG | GAAGAGTAAA | AAATTTGGAG | 720 |
| AAGGGAATTT | CAGATGGGCC | ATTAGAATGG | CTAATGTATC | TACAGGACGA | GAACCTGGTG | 780 |
| ATATACCAGA | GACTTTAGAT | CAACTAAGGT | TGGTTATTTG | CGATTTACAA | GAAAGAAGAG | 840 |
| AAAAATTTGG | ATCTAGCAAA | GAAATTGATA | TGGCAATTGT | GACATTAAAA | GTCTTTGCGG | 900 |
| TAGCAGGACT | TTTAAATATG | ACGGTGTCTA | CTGCTGCTGC | AGCTGAAAAT | ATGTATTCTC | 960 |
| AAATGGGATT | AGACACTAGG | CCATCTATGA | AGAAGCAGG | TGAAAAGAG | GAAGGCCCTC | 1020 |
| CACAGGCATA | TCCTATTCAA | ACAGTAAATG | GAGTACCACA | ATATGTAGCA | CTTGACCCAA | 1080 |
| AAATGGTGTC | CATTTTTATG | GAAAAGGCAA | GAGAAGGACT | AGGAGGTGAG | GAAGTTCAAC | 1140 |
| TATGGTTTAC | TGCCTTCTCT | GCAAATTTAA | CACCTACTGA | CATGGCCACA | TTAATAATGG | 1200 |
| CCGCACCAGG | GTGCGCTGCA | GATAAAGAAA | TATTGGATGA | AAGCTTAAAG | CAACTGACAG | 1260 |
| CAGAATATGA | TCGCACACAT | CCCCCTGATG | CTCCCAGACC | ATTACCCTAT | TTTACTGCAG | 1320 |
| CAGAAATTAT | GGGTATAGGA | TTAACTCAAG | AACAACAAGC | AGAAGCAAGA | TTTGCACCAG | 1380 |

```
CTAGGATGCA GTGTAGAGCA TGGTATCTCG AGGCATTAGG AAAATTGGCT GCCATAAAAG    1440
CTAAGTCTCC TCGAGCTGTG CAGTTAAGAC AAGGAGCTAA GGAAGATTAT TCATCCTTTA    1500
TAGACAGATT GTTTGCCCAA ATAGATCAAG AACAAAATAC AGCTGAAGTT AAGTTATATT    1560
TAAAACAGTC ATTAAGCATA GCTAATGCTA ATGCAGACTG TAAAAAGGCA ATGAGCCACC    1620
TTAAGCCAGA AAGTACCCTA GAAGAAAAGT TGAGAGCTTG TCAAGAAATA GGCTCACCAG    1680
GATATAAAAT GCAACTCTTG GCAGAAGCTC TTACAAAAGT TCAAGTAGTG CAATCAAAAG    1740
GATCAGGACC AGTGTGTTTT AATTGTAAAA AACCAGGACA TCTAGCAAGA CAATGTAGAG    1800
AAGTGAAAAA ATGTAATAAA TGTGGAAAAC CTGGTCATCT AGCTGCCAAA TGTTGGCAAG    1860
GAAATAGAAA GAATTCGGGA AACTGGAAGG CGGGGCGAGC TGCAGCCCCA GTGAATCAAA    1920
TGCAGCAAGC AGTAATGCCA TCTGCACCTC AATGGAGGA GAAACTATTG GATTTGTAAA     1980
TTATAATAAA GTAGGTACTA CTACAACATT AGAAAAAGG CCAGAAATAC TTATATTTGT     2040
AAATGGATAT CCTATAAAAT TTTTATTAGA CACAGGAGCA GATATAACAA TTTTAAATAG    2100
GAGAGATTTT CAAGTAAAAA ATTCTATAGA AATGGAAGG CAAAATATGA TTGGAGTAGG     2160
AGGAGGAAAG AGAGGAACAA ATTATATTAA TGTACATTTA GAGATTAGAG ATGAAAATTA    2220
TAAGACACAA TGTATATTTG GTAATGTTTG TGTCTTAGAA GATAACTCAT TAATACAACC    2280
ATTATTGGGG AGAGATAATA TGATTAAATT CAATATTAGG TTAGTAATGG CTCAAATTTC    2340
TGATAAGATT CCAGTAGTAA AAGTAAAAAT GAAGGATCCT AATAAAGGAC CTCAAATAAA    2400
ACAATGGCCA TTAACAAATG AAAAAATTGA AGCCTTAACA GAAATAGTAG AAAGACTAGA    2460
AAAAGAAGGG AAAGTAAAAA GAGCAGATTC AAATAATCCA TGGAATACAC CAGTATTTGC    2520
TATAAAAAAG AAAAGTGGAA AATGGAGAAT GCTCATAGAT TTTAGAGAAT TAAACAAATT    2580
AACTGAGAAA GGAGCAGAGG TCCAGTTGGG ACTACCTCAT CCTGCTGGTC TACAAATAAA    2640
AAAACAAGTA ACAGTATTAG ATATAGGGGA TGCATATTTC ACCATTCCTC TTGATCCAGA    2700
TTATGCTCCT TATACAGCAT TTACTTTACC TAGGAAAAAT AATGCGGGAC CAGGAAGGAG    2760
ATTTGTGTGG TGTAGTCTAC CACAAGGCTG GATTTAAGT CCATTGATAT ATCAAAGTAC     2820
ATTAGATAAT ATAATACAAC CTTTTATTAG ACAAAATCCT CAATTAGATA TTTACCAATA    2880
TATGGATGAC ATTTATATAG GATCAAATTT AAGTAAAAAG GAGCATAAAG AAAAGGTAGA    2940
AGAATTAAGA AAATTACTAT TATGGTGGGG ATTTGAAACT CCAGAAGATA AATTACAGGA    3000
AGAACCCCCA TATACATGGA TGGGTTATGA ATTACATCCA TTAACATGGA CAATACAACA    3060
GAAACAGTTA GACATTCCAG AACAGCCCAC TCTAAATGAG TTGCAAAAAT TAGCAGGAAA    3120
AATTAATTGG GCTAGCCAAG CTATTCCAGA CTTGAGTATA AAAGCATTAA CTAACATGAT    3180
GAGAGGAAAT CAAAACCTAA ATTCAACAAG ACAATGGACT AAAGAAGCTC GACTGGAAGT    3240
ACAAAAGGCA AAAAAGGCTA TAGAAGAACA AGTACAACTA GGATACTATG ACCCCAGTAA    3300
GGAGTTATAT GCTAAATTAA GTTGGTGGG ACCACATCAA ATAAGTTATC AAGTATATCA     3360
GAAGGATCCA GAAAAGATAC TATGGTATGG AAAAATGAGT AGACAAAAGA AAAGGCAGA    3420
AAATACATGT GATATAGCCT TAAGAGCATG CTATAAGATA AGAGAAGAGT CTATTATAAG    3480
AATAGGAAAA GAACCAAGAT ATGAAATACC TACTTCTAGA GAAGCCTGGG AATCAAATTT    3540
AATTAATTCA CCATATCTTA AGGCCCCACC TCCTGAGGTA GAATATATCC ATGCTGCTTT    3600
GAATATAAAG AGAGCGTTAA GTATGATAAA AGATGCTCCA ATACCAGGAG CAGAAACATG    3660
GTATATAGAT GGAGGTAGAA AGCTAGGAAA AGCAGCAAAA GCAGCCTATT GGACAGATAC    3720
AGGAAAGTGG CGAGTGATGG ATTTAGAAGG CAGTAATCAG AAGGCAGAAA TACAAGCATT    3780
```

```
ATTATTGGCA TTAAAAGCAG GATCAGAGGA AATGAATATT ATAACAGATT CACAATATGT    3840
TATAAATATT ATTCTTCAAC AACCAGATAT GATGGAGGGA ATCTGGCAAG AAGTTTTAGA    3900
AGAATTGGAG AAGAAAACAG CAATATTTAT AGATTGGGTC CCAGGACATA AAGGTATTCC    3960
AGGAAATGAG GAAGTAGATA AGCTTTGTCA ACAATGATG  ATAATAGAAG GGGATGGGAT    4020
ATTAGATAAA AGGTCAGAAG ATGCAGGATA TGATTTATTA GCTGCAAAAG AAATACATTT    4080
ATTGCCAGGA GAGGTAAAAG TAATACCAAC AGGGGTAAAG CTAATGTTGC CTAAAGGATA    4140
TTGGGGATTA ATAATAGGAA AAAGCTCGAT AGGGAGTAAA GGATTGGATG TATTAGGAGG    4200
AGTAATAGAT GAAGGATATC GAGGTGAAAT TGGAGTAATA ATGATTAATG TATCAAGAAA    4260
ATCAATCACT TTAATGGAAC GACAAAAGAT AGCACAATTA ATAATATTGC CTTGTAAACA    4320
TGAAGTATTA GAACAAGGAA AAGTAGTAAT GGATTCAGAG AGAGGAGACA ATGGTTATGG    4380
GTCAACAGGA GTATTCTCCT CTTGGGTTGA CAGAATTGAG GAAGCAGAAA TAAATCATGA    4440
AAAATTTCAC TCAGATCCAC AGTACTTAAG GACTGAATTT AATTTACCTA AGATGGTAGC    4500
AGAAGAGATA AGACGAAAAT GCCCAGTATG CAGAATCATA GGAGAACAAG TGGGAGGACA    4560
ATTGAAAATA GGGCCTGGTA TCTGGCAAAT GGATTGCACA CACTTTGATG GCAAAATAAT    4620
TCTTGTGGGT ATACATGTGG AATCAGGATA TATATGGGCA CAAATAATTT CTCAAGAAAC    4680
TGCTGACTGT ACAGTTAAAG CTGTTTTACA ATTGTTGAGT GCTCATAATG TTACTGAATT    4740
ACAAACAGAT AATGGACCAA ATTTTAAAAA TCAAAGATG  GAAGGAGTAC TCAATTACAT    4800
GGGTGTGAAA CATAAGTTTG GTATCCCAGG GAACCCACAG TCACAAGCAT TAGTTGAAAA    4860
TGTAAATCAT ACATTAAAAG TTTGGATTCA GAAATTTTTG CCTGAAACAA CCTCCTTGGA    4920
TAATGCCTTA TCTCTCGCTG TACATAGTCT CAATTTTAAA AGAAGAGGTA GGATAGGAGG    4980
GATGGCCCCT TATGAATTAT TAGCACAACA AGAATCCTTA AGAATACAAG ATTATTTTC    5040
TGCAATACCA CAAAAATTGC AAGCACAGTG GATTTATTAT AAAGATCAAA AAGATAAGAA    5100
ATGGAAAGGA CCAATGAGAG TAGAATACTG GGGACAGGGA TCAGTATTAT TAAAGGATGA    5160
AGAGAAGGGA TATTTTCTTA TACCTAGGAG ACACATAAGG AGAGTTCCAG AACCCTGCGC    5220
TCTTCCTGAA GGGGATGAGT GAAGAAGATT GGCAGGTAAG TAGAAGACTC TTTGCAGTGC    5280
TCCAAGGAGG AGTAAATAGC GCTATGCTAT ACATATCTAG ACTACCTCCG GATGAAAGAG    5340
AAAAGTATAA AAAAGACTTC AAGAAAAGAC TTTTTGACAC AGAAACAGGA TTTATAAAGA    5400
GACTACGGAA AGCTGAAGGA ATAAATGGA  GCTTTCATAC TAGAGATTAT TACATAGGAT    5460
ATGTCAGAGA ATGGTGGCA  GGATCCACTA CATCACTAAG TCTAAGGATG TATATATATA    5520
TAAGTAACCC ACTATGGCAT TCTCAGTATC GTCCAGGCTT GAAAAATTTC AATAAGGAAT    5580
GGCCTTTTGT AAATATGTGG ATAAAAACAG GATTTATGTG GGATGATATT GAAAACAAA    5640
ATATTTGTAT AGGAGGAGAA GTTCACCAG  GATGGGACC   AGGATGGTA  GGTATAGCAA    5700
TAAAAGCTTT TAGTTGTGGC GAAAGAAAGA TTGAGGCTAC TCCTGTAATG ATTATAAGAG    5760
GAGAAATAGA TCCAAAAAAA TGGTGCGGAG ATTGTTGGAA TTTAATGTGT CTTAGAAACT    5820
CACCTCCAAA GACTTTACAA AGACTCGCTA TGTTGGCGTG TGGCGTGCCG GCTAAGAAGT    5880
GGCGAGGATG CTGTAATCAA CGCTTTGTTT CTCCTTACAG AACGCCTGCT GATTTAGAGG    5940
TCATTCAATC CAAGCCCAGC TGGAACCTGT TATGGTCGGG AGAACTATGA ATGGAAGAAA    6000
TAATAGTATT ATTCAATAGG GTCACTGAGA AACTAGAAAA AGAATTAGCT ATCAGAATAT    6060
TTGTATTAGC ACATCAATTA GAAAGGGACA AAGCTATTAG ATTACTACAA GGATTATTTT    6120
GAAGATATAG ATTTAAGAAA CCCCGAGCAG ATTATTGTTT ATGTTGGTGG TGTTGCAGAT    6180
```

```
TCTATTATTG GCAGTTGCAA TCTACATTAT CAATAACTAC TGCTTAGAAA TATTTATATT    6240
AATTTTCATT TGCAACAATA AGAATGGCAG AAGGATTTGC AGCCAATAGA CAATGGATAG    6300
GACCAGAAGA AGCTGAAGAG TTATTAGATT TTGATATAGC AACACAAATG AGTGAAGAAG    6360
GACCACTAAA TCCAGGAGTA AACCCATTTA GGGTACCTGG AATAACAGAA AAAGAAAAGC    6420
AAAACTATTG TAACATATTA CAACCTAAGT TACAAGATCT AAGGAACGAA ATTCAAGAGG    6480
TAAAACTGGA AGAAGGAAAT GCAGGTAAGT TTAGAAGAGC AAGATTTTTA AGGTATTCTG    6540
ATGAACGTGT ATTGTCCCTG GTTCATGCGT TCATAGGATA TTGTATATAT TTAGGTAATC    6600
GAAATAAGTT AGGATCTTTA AGACATGACA TTGATATAGA AGCACCCCAA GAAGAGTGTT    6660
ATAATAATAG AGAGAAGGGT ACAACTGACA ATATAAAATA TGGTAGACGA TGTTGCCTAG    6720
GAACGGTGAC TTTGTATCTG ATTTTATTTA CAGGAGTAAT AGTATATTCA CAGACAGCCG    6780
GCGCTCAGGT AGTATGGAGA CTTCCACCAT TAGTAGTCCC AGTAGAAGAA TCAGAAATAA    6840
TTTTTTGGGA TTGTTGGGCA CCAGAAGAAC CCGCCTGTCA GGACTTTCTT GGGGCAATGA    6900
TACATCTAAA AGCTAAGACA AATATAAGTA TACGAGAGGG ACCTACCTTG GGAATTGGG     6960
CTAGAGAAAT ATGGGCAACA TTATTCAAAA AGGCTACTAG ACAATGTAGA AGAGGCAGAA    7020
TATGGAAAAG ATGGAATGAG ACTATAACAG GACCATCAGG ATGTGCTAAT AACACATGTT    7080
ATAATGTTTC AGTAATAGTA CCTGATTATC AGTGTTATTT AGATAGAGTA GATACTTGGT    7140
TACAAGGGAA AATAAATATA TCATTATGTC TAACAGGAGG AAAAATGTTG TACAATAAAG    7200
TTACAAAACA ATTAAGCTAT TGTACAGACC CATTACAAAT CCCACTGATC AATTATACAT    7260
TTGGACCTAA TCAAACATGT ATGTGGAATA CTTCACAAAT TCAGGACCCT GAAATACCAA    7320
AATGTGGATG GTGGAATCAA ATGGCCTATT ATAACAGTTG TAAATGGGAA GAGGCAAAGG    7380
TAAAGTTTCA TTGTCAAAGA ACACAGAGTC AGCCTGGATC ATGGTTTAGA GCAATCTCGT    7440
CATGGAAACA AAGAAATAGA TGGAGTGGA GACCAGATTT TAAAAGTAAA AAGGTGAAAA     7500
TATCTCTACC ATGCAATAGC ACAAAAAACC TAACCTTTGC AATGAGAAGT TCAGGAGATT    7560
ATGGAGAAGT AACGGGAGCT TGGATAGAGT TTGGATGTCA TAGAAATAAA TCAAACCTTC    7620
ATACTGAAGC AAGGTTTAGA ATTAGATGTA GATGGAATGT AGGGAGTGAT ACCTCGCTCA    7680
TTGATACATG TGGAAACACT CCAAATGTTT CAGGTGCGAA TCCTGTAGAT TGTACCATGT    7740
ATTCAAACAA AATGTACAAT TGTTCTTTAC AAAACGGGTT TACTATGAAG GTAGATGACC    7800
TTATTGTACA TTTCAATATG ACAAAGCTG TAGAAATGTA TAATATTGCT GGAAATTGGT     7860
CTTGTACATC TGACTTGCCA TCGTCATGGG GGTATATGAA TTGTAATTGT ACAAATAGTA    7920
GTAGTAGTTA TAGTGGTACT AAAATGGCAT GTCCTAGCAA TCGAGGCATC TTAAGGAATT    7980
GGTATAACCC AGTAGCAGGA TTACGACAAT CCTTAGAACA GTATCAAGTT GTAAACAAC     8040
CAGATTACTT ACTGGTCCCA GAGGAAGTCA TGGAATATAA ACCTAGAAGG AAAAGGGCAG    8100
CTATTCATGT TATGTTGGCT CTTGCAACAG TATTATCTAT TGCCGGTGCA GGGACGGGG     8160
CTACTGCTAT AGGGATGGTA ACACAATACC ACCAAGTTCT GGCAACCCAT CAAGAAGCTA    8220
TAGAAAAGGT GACTGGAGCC TTAAAGATAA ACAACTTAAG ATTAGTTACA TTAGAGCATC    8280
AAGTACTAGT AATAGGATTA AAAGTAGAAG CTATGGAAAA ATTTTTATAT ACAGCTTCG     8340
CTATGCAAGA ATTAGGATGT AATCAAAATC AATTCTTCTG CAAAATCCCT CTTGAGTTGT    8400
GGACAAGGTA TAATATGACT ATAAATCAAA CAATATGGAA TCATGGAAAT ATAACTTTGG    8460
GGGAATGGTA TAACCAAACA AAAGATTTAC AACAAAAGTT TTATGAAATA ATAATGGACA    8520
TAGAACAAAA TAATGTACAA GGGAAAACAG GGATACAACA ATTACAAAAG TGGGAAGATT    8580
```

```
GGGTAAGATG GATAGGAAAT ATTCCACAAT ATTTAAAGGG ACTATTGGGA GGTATCTTGG      8640

GAATAGGATT AGGAGTGTTA TTATTGATTT TATGTTTACC TACATTGGTT GATTGTATAA      8700

GAAATTGTAT CCACAAGATA CTAGGATACA CAGTAATTGC AATGCCTGAA GTAGAAGGAG      8760

AAGAAATACA ACCACAAATG GAATTGAGGA GAAATGGTAG GCAATGTGGC ATGTCTGAAA      8820

AAGAGGAGGA ATGATGAAGT ATCTCAGACT TATTTTATAA GGGAGATACT GTGCTGAGTT      8880

CTTCCCTTTG AGGAAGGTAT GTCATATGAA TCCATTTCGA ATCAAATCAA ACTAATAAAG      8940

TATGTATTGT AAGGTAAAAG GAAAAGACAA AGAAGAAGAA GAAAGAAGAA AGCCTTCAAG      9000

AGGATGATGA CAGAGTTAGA AGATCGCTTC AGGAAGCTAT TTGGCACGAC TTCTACAACG      9060

GGAGACAGCA CAGTAGATTC TGAAGATGAA CCTCCTAAAA AAGAAAAAAG GGTGGACTGG      9120

GATGAGTACT GGAACCCTGA AGAAATAGAA AGAATGCTTA TGGACTAGGG ACTGTTTACG      9180

AACAAATGAT AAAAGGAAAT AGCTGAGCAT GACTCATAGT TAAAGCGCTA GCAGCTGCTT      9240

AACCGCAAAA CCACATCCTA TGTAAAGCTT GCTAATGACG TATAAGTTGT TCCATTGTAA      9300

GAGTATATAA CCAGTGCTTT GTGAAACTTC GAGGAGTCTC TTTGTTGAGG ACTTTTGAGT      9360

TCTCCCTTGA GGCTCCCACA GATACAATAA ATATTTGAGA TTGAACCCTG TCGAGTATCT      9420

GTGTAATCTT TTTTACCTGT GAGGTCTCGG AATCCGGGCC GAGAACTTCG CA             9472
```

( 2 ) INFORMATION FOR SEQ ID NO:10:

( i ) SEQUENCE CHARACTERISTICS:
        ( A ) LENGTH: 9468 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: P ( i x ) FEATURE:
        ( A ) NAME/KEY: CDS
        ( B ) LOCATION: join(628..1977, 1869..5240, 5236..5988, 5992
        . . 6222, 6262..8824, 6709..6912)

( x i ) SEQUENCE DESCRIPTION: SEQ ID NO:10:

```
TGGGATGAGT ATTGGGACCC TGAAGAAATA GAAAGAATGC TTATGGACTA AGAACTGTCA       60

CAAACAAATG ATAAATGGAA ACAGCTGAAC ATGACTCATA GTTAAAGCGC TAGCAGCTGC      120

TTAACCGCAA AACCACATCC TATGTAAAGC TTGCCAATGA CGTATAATTT GCTCCACTGT      180

AAGAGTATAT AATCAGTGCT TTGTGAAGCT TCGAAGAGTC TCTCTGCTGA GGACTTTCGA      240

GTTCTCCCTT GAGGCTCCCA CAGATACAAT AAATATTTGA GATTGAACCC TGTCAAGTAT      300

CTGTGTAGTC TTTTCTACCT GTGAGGTCTC GGAATCCGGG CCGAGAACTT CGCAGTTGGC      360

GCCCGAACAG GGACTTGAGA AAGAGTGATT GAGGAAGTGA AGCTAGAGCA GTAGAAAGCT      420

GTTAAGCAGA ACTCCTGTTG ACCTAAATAG GGAAGCAGTA GCAGACGCTG CTAAACAGTG      480

AGTATCTCTA GTGAAGCAGA CTCGAGCTCA TAATCAAGTC ACTGTTTAAA GGCCCAGATA      540

AATTACATTT GGTGACTCTT CGCGGACCTT CAAGCCAGGA GATTCGCCGA GGACAGCTA      600

ACAAGGTAGG AGAGACTCTA CAGCAACATG GGAATGGAC AGGGCGAGA TTGGAAAATG       660

GCCATTAAGA GATGTAGTAA TGTTGCTGTA GGAGTAGGGG GAAGAGTAA AAAATTTGGA      720

GAGGGAATT TTAGGTGGGC CATAAGAATG GCTAATGTAT CTACAGGACG AGAACCTGGT       780

GATATACCAG AGACTTTAGA TCAACTAAGG TTGGTTATTT GCGATTTACA AGAAAGAAGA      840
```

```
GAAAAATTTG GATCTAGCAA AGAAATTGAC ATGGCAATTA CAACATTAAA AGTCTTTGCA      900
GTAGTGGGAC TTTTAAATAT GACAGTGTCT ACTGCTGCTG CAGCTGAAAA TATGTATACT      960
CAGATGGGAT TAGACACTAG ACCGTCTACA AAAGAAGCGG GAGGAAAAGA GGAAGGCCCT     1020
CCACAGGCAT ATCCTATTCA AACAGTAAAT GGAGCACCAC AATATGTAGC ACTTGACCCA     1080
AAAATGGTGT CCATTTTTAT GGAAAAGGCA AGAGAGGGAT TAGGAGGTGA GGAAGTTCAA     1140
CTATGGTTTA CAGCCTTCTC TGCAAATTTA ACACCTACTG ACATGGCCAC ATTAATAATG     1200
GCCGCACCCG GGTGCGCTGC AGATAAAGAA ATATTGGATG AAAGCTTAAA GCAATTGACA     1260
GCAGAATATG ATCGGACAAA TCCCCCTGAT GGTCCTAGAC CATTACCCTA TTTTACTGCA     1320
GCAGAAATTA TGGGTATAGG ATTAACTCAA GAACAACAAG CAGAAGCAAG ATTTGCACCA     1380
GCTAGGATGC AATGTAGAGC ATGGTATCTT GAGGCATTAG GAAAATTAGC CGCCATAAAG     1440
GCTAAATCTC CTCGAGCTGT GCAGTTAAGA CAAGGAGCTA GGAAGATTA TTCATCCTTT      1500
ATAGACAGAT TGTTTGCCCA AATAGATCAA GAACAAAATA CAGCTGAAGT TAAGTTATAT     1560
CTAAAACAGT CATTAAGCAT AGCTAATGCT AATGCAGAAT GCAAAAAGGC AATGAGTCAT     1620
CTTAAGCCAG AAAGTACCCT AGAAGAAAAG TTGAGAGCTT GTCAAGAGAT AGGATCCCCA     1680
GGATATAAAA TGCAACTCTT GGCAGAAGCT CTTACAAAAG TTCAAGTAGT GCAATCAAAA     1740
GGATCAGGAC CAGTGTGTTT TAATTGTAAA AAACCAGGGC ATCTAGCAAG ACAGTGTAGA     1800
GATGTGAAAA AATGTAATAA ATGTGGAAAA CCTGGTCATT TAGCTGCCAA ATGTTGGCAA     1860
GGTGGTAAAA GAAATTCGGG AAACTGGAAG GCGGGGCGAG CTGCAGCCCC AGTGAATCAA     1920
GTGCAGCAAA CAGTAATGCC ATCTGCACCT CCAATGGAGG AAAAATTATT GGATTTATAA     1980
ATTACAATAA AGTAGGTACT ACTACATCAT TAGAAAAGAG GCCAGAAATA CTTATATTTG     2040
TGAATGGGTA CCCTATAAAA TTTTTATTAG ATACAGGAGC AGATATAACA ATTTTAAATA     2100
GGAGAGATTT TCAAGTAAAA AACTCTATAG AAAATGGAAG ACAAAATATG ATTGGAGTAG     2160
GGGGAGGAAA GAGAGGAACA AATTATATCA ATGTGCATTT AGAGATTAGA GATGAAAATT     2220
ACAAGACACA ATGTATATTT GGCAATGTTT GTGTCTTAGA AGATAACTCA TTAATACAAC     2280
CATTATTAGG GAGAGATAAT ATGATTAAAT TTAATATCAG GTTAGTAATG GCTCAAATTT     2340
CTGATAAGAT TCCAATAGTA AAAGTAAAGA TGAAGGATCC TAATAAAGGA CCTCAAATAA     2400
AACAATGGCC ATTATCAAAT GAAAAAATTG AAGCTTTAAC AGAAATAGTA GAAAGACTAG     2460
AAAGGGAAGG GAAAGTAAAA AGAGCAGATC CAAATAATCC ATGGAATACA CCAGTATTTG     2520
CTATAAAAAA GAAAAGTGGA AAATGGAGGA TGCTCATAGA TTTTAGAGAA TTGAACAAAT     2580
TAACTGAGAA AGGAGCAGAA GTCCAGTTGG GACTACCTCA CCCTGCTGGT TTACAAATGA     2640
AAAAACAAAT AACAGTATTA GATATAGGGG ATGCATATTT CACCAATCCC CTTGACCCAG     2700
ATTATGCTCC TTATACAGCA TTTACTTTAC CTAGGAAGAA TAATGCGGGA CCAGGAAGAA     2760
GATTTGTGTG GTGTAGTCTA CCACAAGGCT GGATTTTAAG TCCATTGATA TATCAAAGTA     2820
CATTAGATAA TATAATACAA CCTTTTATTA GACAAAATCC TCAATTAGAT ATTTATCAAT     2880
ATATGGATGA CATTTATATA GGATCAAACT TAAGTAAAAA GGAGCATAAA GAAAAAGTAG     2940
AAGAATTAAG AAAATTACTA TTATGGTGGG GATTTGAAAC TCCAGAGGAT AAATTACAGG     3000
AAGACCCCC ATATAAATGG ATGGGTTATG AATTACATCC ATTAACATGG ACAATACAAC      3060
AGAAACAGTT AGAAATTCCA GAAAAGCCTA CATTAAATGA ATTACAAAAA TTAGCAGGAA     3120
AAATTAATTG GGCTAGCCAA ACTATTCCAG AATTAAGTAT AAAATCATTA ACTAACATGA     3180
CGAGAGGAAA TCAAAACCTA AATTCAACAA GAGAGTGGAC TGAGGAAGCT AGACTAGAAG     3240
```

```
TACAGAAGGC CAAAAGGGCT ATTGAAGAAC AAGTACAACT AGGATATTAT GACCCTAGTA    3300
AAGAATTGTA TGCTAAATTA AGCTTAGTGG GACCACATCA AATAAGTTAT CAAGTATATC    3360
AGAAGTGTCC AGAAAAGATC TTATGGTATG GAAAAATGAG TAGGCAAAAG AAAAAGGCAG    3420
AAAATACGTG TGATATAGCG TTAAGAGCAT GCTACAAAAT AAGGGAAGAA TCCATTATAA    3480
GAATAGGAAA AGAACCAAGA TATGAAATAC CTACTTCTAG AGAAGCCTGG GAATCAAATT    3540
TAATTAATTC ACCATATCTT AAAGCCCCAC CTCCAGAAGT AGACTATATC CATGCTGCTT    3600
TAAACATAAA AAGAGCACTA AGTATGATAA AAGATCCTCC AATATCAGGA GCAGAAACGT    3660
GGTATATAGA TGGAGGTAGA AAGCTAGGAA AAGCAGCAAA AGCAGCCTAT GGACAGATA     3720
CAGGAAAGTG GCAAGTAATG GAATTAGAAG GTAGTAATCA GAAGGCGGAA ATACAAGCAT    3780
TATTATTGGC ATTAAAGGCA GGACCAGAGG AAATGAATAT TATAACAGAT CTCAGTATA     3840
TGATAAATAT TCTTAGTCAA CAACCAGATA AGATGGAAGG AATCTGGCAA GAAGTTTTAG    3900
AAGAATTGGA AAAGAAAACA GCAATATTTA TAGATTGGGT CCCAGGACAT AAAGGTATTC    3960
CAGGAAATGA GGAAGTAGAT AAGCTTTGTC AAACAATGAT GATAATAGAA GGGATGGGA     4020
TATTAGATAA AGAACAGAA GATGCAGGAT ATGATTTATT AGCTGCAAAA GAAATACATC     4080
TATTACCAGG AGAGGTAAAA GTAATACCAA CGGGAGTAAA ACTAATGTTG CCTAAAGGAC    4140
ATTGGGGATT AATAATGGGA AAAAGCTCGA TAGGGAGTAA AGGATTGGAT GTATTAGGAG    4200
GGGTAATAGA TGAAGGATAT CGAGGTGAAA TTGGAGTAAT AATGATTAAT TTATCAAAAA    4260
AATCAATCAC TTTGTTGGAA CAACAGAAGA TAGCACAATT AATAATATTG CCTCATAAAC    4320
ATGAAGCATT AGAACAGGGG AAAGTAGTAA TGGATTCAGA GAGAGGAGAA AAAGGTTATG    4380
GGTCAACAGG AGTATTCTCC TCTTGGGTTG ACAGAATTGA GGAAGCAGAA ACAAATCATG    4440
AAAAATTTCA CTCAGATCCG CAATACTTAA GGACTGAATT TAATTTACCC AAGATGGTGG    4500
CAGAAGAGAT AAGACGAAAA TGCCCTGTAT GTAGGATTAG AGGAGAACAA GTGGGAGGGC    4560
AATTGAAGAT AGGGCCTGGT ATCTGGCAAA TGGATTGCAC ACACTTTGAT GGCAAAATAA    4620
TTCTTGTGGC TATACATGTG GAATCAGGAT ATATATGGGC ACAAATAATC TCTCAAGAAA    4680
CTGCTGATTG TACAGTTAAA GCTGTCTTAC AATTATTGAG TGCTCATATT GTTACGGAGT    4740
TACAAACAGA TAATGGACCA AATTTTAAAA ATCAAAAGAT GGAAGGAGTA CTCAATTATA    4800
TGGGTGTGAA ACATAAGTTT GGTATCCCAG GAAACCCACA ATCACAAGCA TTAGTTGAAA    4860
ATGTAAATCA GACATTAAAA GTCTGGGTTC ACAAATTTTT GCCTGAAACA ACCTCCTTGG    4920
ATAATGCATT AGCTCTCGCT GTGCATTGTC TCAATTTTAA ACAAAGGGGT AGAATAGGAG    4980
GGATGGCCCC TTATGAATTA TTAGCACAAC AAGAATCCTT AAGAATACAA GATTATTTCT    5040
CTGCAATACC ACAAAAATTG CAAGCACAAT GGATTTATTA TAAAGATCAA AAAGATAAGA    5100
AATGGAAAGG GCCAATGAGA GTAGAATACT GGGGACAAGG ATCAGTGTTA TTAAAGGATG    5160
AAGAGAAGGG ATATTTCTT ATACCTAGGA GACACGTAAA GAGAGTCCCA GAACCCTGCG     5220
CTCTTCCTGA AGGGGATGAG TGACGAAGAT TGGCAGGTAA GTAGAAGACT CTTTGCAGTG    5280
CTCCAAGGAG GGGTATATAA CGCTATGCTA TATATATCTA GACTACCTCA GGACGAAAGA    5340
GAAAAATATA AAAGGATTT CAAGAAAGA CTTTAGATA CAGAAACAGG ATTTATAAAA       5400
AGACTAAGGA AAGCTGAAGG AATAAAATGG AGCTTTCATA CTAGAGATTA TCATGTAGGA    5460
TATGTTAGAG AAATGGTAGC AGGACCCACT ACACCACATA GTCTAAGGCT GTATGTGTAT    5520
ATAAGTAATC CACTATGGCA TTCTCAGTAT CGTCCAGGCT TGGTAAATTT TAATAAGGAA    5580
TGGCCTTTTG TAAATCTATG GATAAAAACA GGATTTATGT GGGATGATAT TGAAAACAA     5640
```

```
AATATTTGTA TAGGAGGAGA AGTTTCACCA GGATGGGGAC CTGGGATGAT AGGTATAGCG   5700
ATAAAAGCTT TTAGTTGTGG CGAAAGAAAG ATTGAGGCTA CTCCTGTAAT GATTATAAGA   5760
GGAGAAATAA ATCCAAAAAA ATGGTGTGGA GACTGTTGGA ATTTGATGTG TCTTAGAAAC   5820
TCACCTCCAG AGACTTTACA AAGGCTCGCT ATGTTGGCAT GTGGAGTACA GGCTAAGAGC   5880
TGGCGAGGAT GCTGTAATCA ACGTTTTGTT TCTCCTTACA GAACACCTGC TGATTTAGAG   5940
GTTATTCAAT CCAAACCCGG CTGGTGCATG TTATGGCGAG GAAAACTGTG AATGGAAGTA   6000
ATACGGATAT TTAATAAGGT CGCTGAAAGA TTAGACAAGG AAGCAGCCAT CAGGATATTT   6060
GTATTAGCAC ATCAATTAGA GAGGGATAAA TTGATTAGAC TTCTGCAAGG ACTACTTTGG   6120
AGACTGAGAT TTAGAAAACC TAAATCAAAA GATTGTTTAT GTTGGTTTTG CTGCAGATTA   6180
TATTATTGGC AGTTGCAGTC TACATTATCC ATAGATACTG CTTAGAAATA TTTATAATAA   6240
TATTTCATTT GCAACAATAA TTATGGCAGA AGGGTTTGCA GCCAATAGAC AATGGATAGG   6300
GCCAGAAGAA GCTGAAGAGC TATTAGATTT TGATAAAGCA ACACAAATGA ATGAAGAAGG   6360
GCCACTAAAT CCAGGAGTAA ACCCATTTAG AGTACCTGCA GTAACAGAAG CAGACAAGCA   6420
AGAATATTGT AAGATATTAC AACCCCGATT ACAAGAGATA AGGAATGAAA TTCAAGAAGT   6480
AAAACTAGAA GAAGGAAATG CAGGTAAGTT TAGAAGAGCA AGATTCTTGA GATATTCTGA   6540
TGAAAGTATA TTATCCTTAA TTCATTTGTT CATAGGGTAT TGTACATACT TAGTAAATAG   6600
AAGGAGGTTA GGATCTTTAA GGCATGACAT AAATATAGAA GCGCCTCAAG AAGAGCAGTA   6660
TAGCAGTAGA GAGCAGGGCA CAACTGAGAA TATAAAATAT GGTAGACGAT GCTTGATAGG   6720
AACAGCAAGT CTGTACTTGT TGCTTTTTAT AGGAGTGGCA ATATATTTAG GTACAACCAA   6780
TGCTCAGATA GTATGGAGAC TTCCACCATT AGTAGTCCCA GTAGAAGAAT CAGAAATAAT   6840
TTTTGGGAT TGTTGGGCAC CAGAGGAGCC CGCCTGTCAA GACTTTCTTG GGCAATGAT    6900
ACATCTAAAA GCTAGTACAA ATATAAGTAT ACAAGAAGGA CCTACCTTGG GGAATTGGGC   6960
TAGAGAAATA TGGGGAACAT TATTCAAAAA AGCTACTAGA CATTGTAGGA GAAATAAAAT   7020
ATGGAAAAGG TGGAATGAAA CTATAACAGG ACCAGTAGGA TGTGCTAATA ATACATGTTA   7080
TAATATCTCT GTAATAATAC CTGATTATCA ATGTTATCTA GATAGAGTAG ATACTTGGTT   7140
ACAAGGGAAA GTAAATATAT CATTATGCCT AACAGGAGGA AAAATGTTGT ATAATAGAGA   7200
TACAAAACAA TTAAGCTATT GTACAGACCC ATTACAAATC CCACTGATCA ATTATACATT   7260
TGGGCCTAAT CAAACATGTA TGTGGAACAC TTCACAGATT CAAGACCCGG AGATACCAAA   7320
ATGTGGATGG TGGAATCAAA TAGCCTATTA TAACAGTTGT AGATGGGAAA GCACAAATGT   7380
AAAGTTTTAT TGTCAAAGAA CACAGAGTCA GCCTGGAACA TGGATTAGAA CAATCTCATC   7440
ATGGAGACAA AAGAATAGAT GGGAATGGAG ACCAGACTTT GAAAGCGAAA AAGTTAAAAT   7500
ATCATTACAA TGTAATAGTA CACATAATTT AACTTTTGCA ATGAGAAGTT CAGGAGATTA   7560
TGGAGAAGTA ATGGGAGCTT GGATAGAATT TGGATGTCAT AGGAACAAAT CAAGATTCCA   7620
TACTGAAGCA AGGTTTAGAA TTAGATGTAG ATGGAATGTA GGGGATAATA CCTCACTCAT   7680
TGATACATGT GGAAAAAATC TAAATGTTTC AGGTGCCAAT CCTGTAGATT GTACCATGTA   7740
TGCAAATAAA ATGTATAACT GTTCCTTACA AAACGGGTTT ACTATGAAGG TAGATGACCT   7800
TATTATGCAT TTCAATATGA CAAAAGCAGT AGAAATGTAT AACATTGCTG GGAATTGGTC   7860
TTGTAAATCT GATTTACCAC AAAATTGGGG ATATATGAAT TGTAATTGTA CGAATGGTAC   7920
GAGTAATGAC AATAAAATGG CATGTCCTGA AGATAAGGGT ATCTTAAGAA ATTGGTATAA   7980
TCCAGTAGCA GGATTAAGAC AAGCATTAGA AAAATATCAA GTGGTAAAAC AGCCAGAATA   8040
```

-continued

```
TATAGTAGTA CCAACAGAAG TTATGACCTA TAAATACAAA CAGAAAAGAG CAGCAATTCA 8100
TATTATGTTA GCTCTTGCAA CAGTATTGTC TATAGCTGGG GCAGGAACAG GTGCTACAGC 8160
AATTGGGATG GTGACTCAAT ATCAGCAAGT TTTAGCTACT CATCAAGAAG CATTGGATAA 8220
AATAACTGAA GCATTGAAAA TAAATAATTT AAGGTTAGTT ACTTTAGAGC ATCAAATGTT 8280
AGTCATAGGA TTGAAAGTAG AAGCTATAGA AAAATTTTTA TATACTGCTT TTGCTATGCA 8340
AGAACTAGGA TGTAATCAAA ATCAATTCTT TTGTGAAATT CCCAAAGAGC TATGGCTAAG 8400
GTATAATATG ACATTAAATC AAACAATTTG GAATCATGGA AATATAACTT TAGGGGAATG 8460
GTACAATCAG ACAAAATATT TACAACAAAA ATTTTATGAA ATAATTATGG ATATAGAACA 8520
AAATAATGTA CAAGGAAAAC AAGGATTACA AAAATTACAA AATTGGCAAG ATTGGATGGG 8580
ATGGATAGGA AAAATACCTC AATACTTAAA GGGACTCTTG GGAGGCATTT TGGGAATAGG 8640
TTTGGGAATT CTATTATTGA TTTTATGTTT ACCCACTTTA GTTGATTGTA TTAGAAATTG 8700
TATTAGTAAA GTTCTAGGAT ATACAGTAAT CGCAATGCCT GAGATAGATG ATGAAGAAGA 8760
AACGGTACAA ATGGAATTGA GGAAAAATGG CAGGCAATGT GGCATGTCTG AAAAAGAGGA 8820
GGAATGATGG AGTGCCTCAG AACTGCTTAA TGCAGGAGAG GTGCTGAGCT GATTTCTTCC 8880
CTTTGAGGAA GATATGTCAT ATGAATCCAT TTTGAATCAA AATAATAAGT ATTTGTATTA 8940
TAAGGTAAAA TGAAAAAGAA AAGACAAAGA AGAAGAAGAA AGAAGAAGGC CTTTAAGAAA 9000
ATGATGACAG ATTTAGAAGA CCGCTTCAGA AAACTATTCG GCTCACCCTC TAAAGATGAA 9060
TACACAGAAA TTGAGATAGA AGAAGACCCT CCTAAAAAAG AAAAAAGGGT GGACTGGGAT 9120
GAGTATTGGG ACCCTGAAGA AATAGAAAGA ATGCTTATGG ACTAAGAACT GTCACAAACA 9180
AATGATAAAT GGAAACAGCT GAACATGACT CATAGTTAAA GCGCTAGCAG CTGCTTAACC 9240
GCAAAACCAC ATCCTATGTA AAGCTTGCCA ATGACGTATA ATTTGCTCCA CTGTAAGAGT 9300
ATATAATCAG TGCTTTGTGA AGCTTCGAAG AGTCTCTCTG CTGAGGACTT TCGAGTTCTC 9360
CCTTGAGGCT CCCACAGATA CAATAAATAT TTGAGATTGA ACCCTGTCAA GTATCTGTGT 9420
AGTCTTTTCT ACCTGTGAGG TCTCGGAATC CGGGCCGAGA ACTTCGCA 9468
```